US012655090B2

(12) United States Patent
Hunter et al.

(10) Patent No.: US 12,655,090 B2
(45) Date of Patent: Jun. 16, 2026

(54) CYCLOPROPYLAMIDE COMPOUNDS AGAINST PARASITES IN FISH

(71) Applicants: Intervet Inc., Rahway, NJ (US); Corteva Agriscience LLC, Indianapolis, IN (US)

(72) Inventors: James Edward Hunter, Indianapolis, IN (US); Lori Kay Lawler, Indianapolis, IN (US); Tony Kent Trullinger, Indianapolis, IN (US); Martin Joseph Walsh, Indianapolis, IN (US); Harald Schmitt, Mainz (DE); Anja Regina Heckeroth, Stadecken-Elsheim (DE); Jürgen Lutz, Wiesbaden (DE); Maria Daniela Fähsing, Stadecken-Elsheim (DE); Hartmut Zoller, Hochheim (DE)

(73) Assignee: Intervet Inc., Rahway, NJ (US)

( * ) Notice: Subject to any disclaimer, the term of this patent is extended or adjusted under 35 U.S.C. 154(b) by 398 days.

(21) Appl. No.: 18/263,203

(22) PCT Filed: Jan. 26, 2022

(86) PCT No.: PCT/EP2022/051751

§ 371 (c)(1),
(2) Date: Jul. 27, 2023

(87) PCT Pub. No.: WO2022/162001

PCT Pub. Date: Aug. 4, 2022

(65) Prior Publication Data

US 2024/0116854 A1 Apr. 11, 2024

(30) Foreign Application Priority Data

Jan. 27, 2021 (EP) .................................... 21153646
Dec. 6, 2021 (EP) .................................... 21212467

(51) Int. Cl.

| | |
|---|---|
| ***C07C 233/65*** | (2006.01) |
| ***A23K 20/111*** | (2016.01) |
| ***A23K 50/80*** | (2016.01) |
| ***A61P 33/14*** | (2006.01) |
| ***C07C 233/66*** | (2006.01) |
| ***C07C 233/79*** | (2006.01) |

(52) U.S. Cl.

CPC .......... *C07C 233/65* (2013.01); *A23K 20/111* (2016.05); *A23K 50/80* (2016.05); *A61P 33/14* (2018.01); *C07C 233/66* (2013.01); *C07C 233/79* (2013.01); *C07C 2601/02* (2017.05); *C07C 2601/04* (2017.05)

(58) Field of Classification Search

CPC .......................... C07C 233/65; C07D 207/452
See application file for complete search history.

(56) References Cited

U.S. PATENT DOCUMENTS

| | | | |
|---|---|---|---|
| 5,770,621 | A | 6/1998 | Braidwood |
| 2018/0098541 | A1 | 4/2018 | Heemstra et al. |

FOREIGN PATENT DOCUMENTS

| | | | | |
|---|---|---|---|---|
| WO | 1996008138 A2 | 3/1996 | | |
| WO | 2013167640 A1 | 11/2013 | | |
| WO | 2016168056 A1 | 10/2016 | | |
| WO | 2016168059 A1 | 10/2016 | | |
| WO | WO2016/168059 | * 10/2016 | | ......... C07D 207/452 |
| WO | 2018071327 A1 | 4/2018 | | |
| WO | WO2018/071327 | * 4/2018 | | ......... C07D 207/452 |
| WO | 2018224455 A1 | 12/2018 | | |
| WO | 2019194982 A1 | 10/2019 | | |
| WO | WO2019/194982 | * 10/2019 | | ........... C07C 317/44 |
| WO | 2022161972 A1 | 8/2022 | | |
| WO | 2022162001 A1 | 8/2022 | | |
| WO | 2022162016 A1 | 8/2022 | | |

OTHER PUBLICATIONS

Wolff, M.E., “Burger’s Medicinal Chemistry”, pp. 975-977 (1995).*
Banker et al., “Modern Pharmaceuticals”, p. 596 (1977).*
Aguiar, A.J. et al., Effect of Polymorphism on the Absorption of Chloramphenicol from Chloramphenicol Palmitate, J Pharm Sci, 56(7), 847-853, 1967.
Bastin, R.J.; et al., Salt Selection and Optimization Procedures for Pharmaceutical New Chemical Entities, Organic Process Research and Development, 4, pp. 427-435, 2000.
Belikov, V.G., Pharmaceutical Chemistry, Moscow MEDpress-inform, 4th Edition, 27-29, 2007.
Parajuli, Rishi Ram et al., Prodrug as a Novel Approach of Drug Delivery—A Review, Journal of Drug Delivery & Therapeutics, 5(3), 5-9, 2015.
Wojnarowska, Z. et al., On the kinetics of tautomerism in drugs: New application of broadband dielectric spectroscopy, J Chem Phys, 133, 094507, 1-9, 2010.
Zawilska, Jolanta B. et al., Prodrugs: A challenge for the drug development, Pharmaceutical Reports, 65(1), 1-14, 2013.

* cited by examiner

*Primary Examiner* — Paul V Ward
(74) *Attorney, Agent, or Firm* — David J. Kerwick

(57) ABSTRACT

The present invention relates to cyclopropylamide compounds that are useful in the treatment of parasitic infestations of fish. The compounds have the formula (I).

(I)

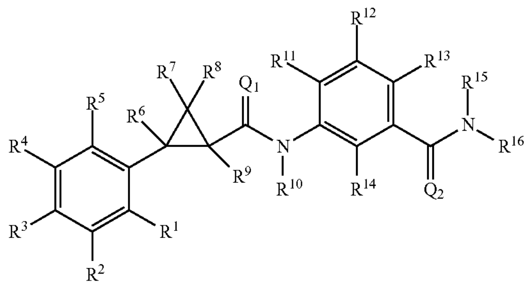

21 Claims, 26 Drawing Sheets

| # | |
|---|---|
| 1500 | 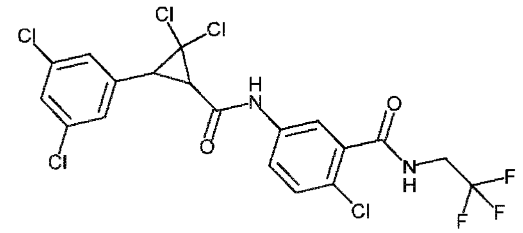 |
| 1501 | 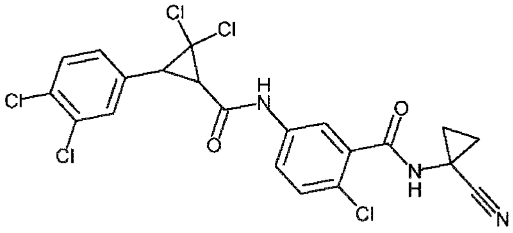 |
| 1502 | AND Enantiomer 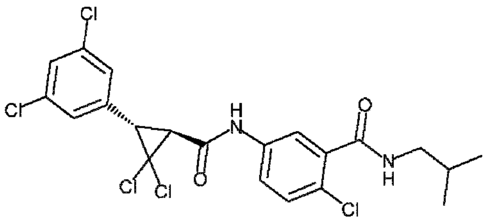 |
| 1503 | AND Enantiomer 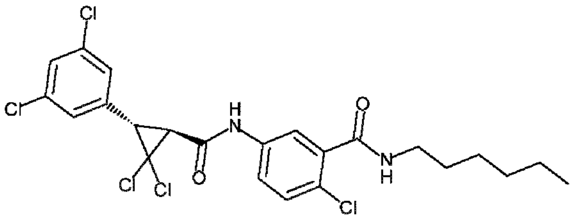 |
| 1504 | AND Enantiomer 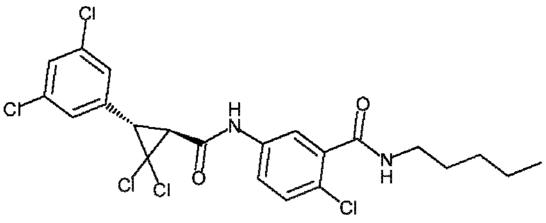 |

| | |
|---|---|
| 1505 | AND Enantiomer 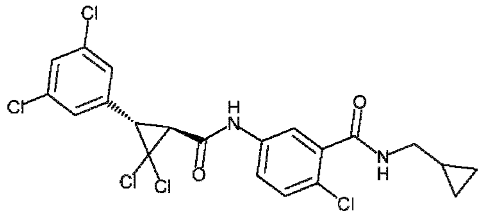 |
| 1506 | AND Enantiomer 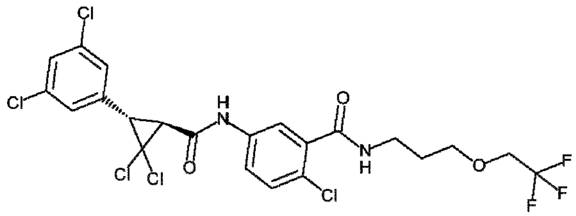 |
| 1507 | AND Enantiomer 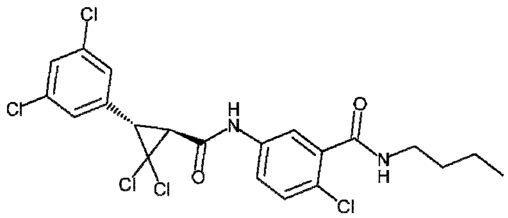 |
| 1508 | 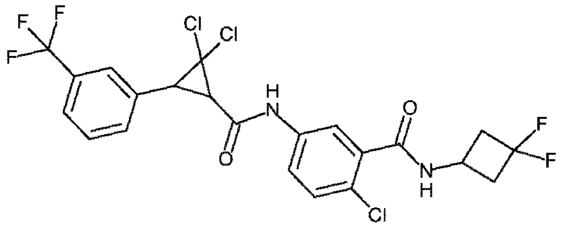 |
| 1509 | AND Enantiomer 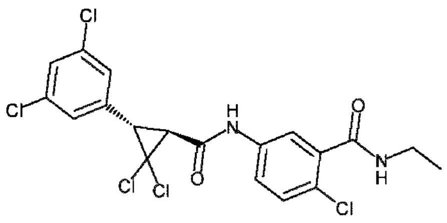 |

| | |
|---|---|
| 1510 | AND Enantiomer 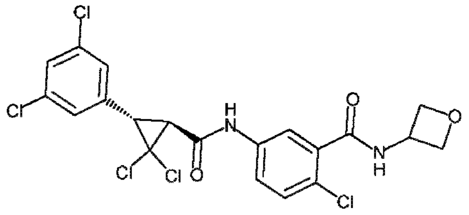 |
| 1511 | AND Enantiomer 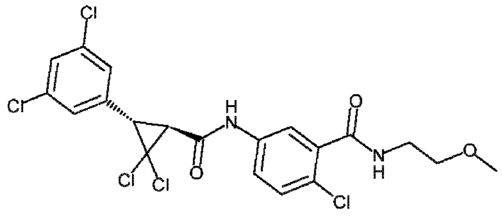 |
| 1512 | AND Enantiomer 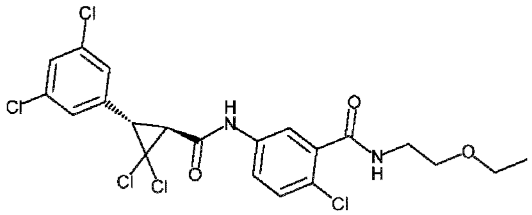 |
| 1513 | AND Enantiomer 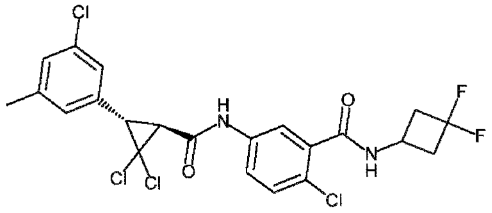 |
| 1514 | AND Enantiomer 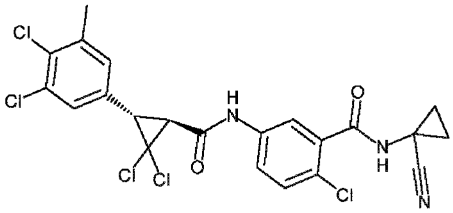 |

| | |
|---|---|
| 1515 | AND Enantiomer 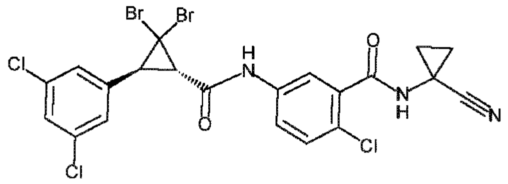 |
| 1516 | AND Enantiomer 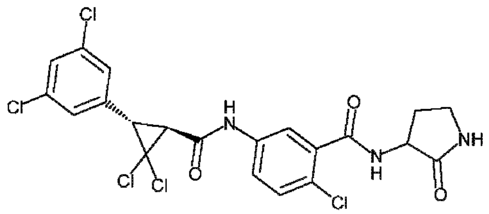 |
| 1517 | AND Enantiomer 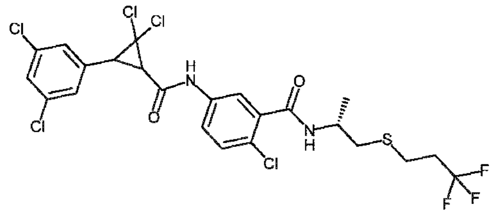 |
| 1518 | AND Enantiomer 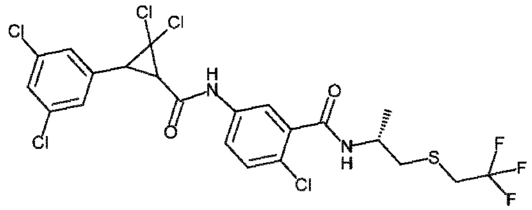 |
| 1519 | AND Enantiomer 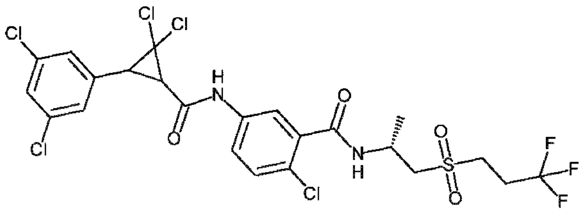 |

| | |
|---|---|
| 1520 | AND Enantiomer 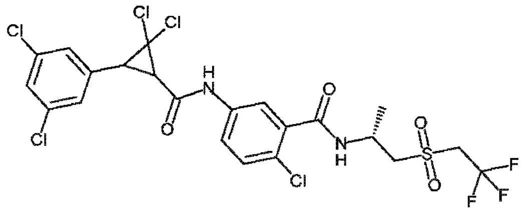 |
| 1521 | AND Enantiomer 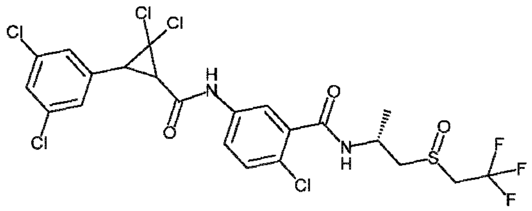 |
| 1522 | 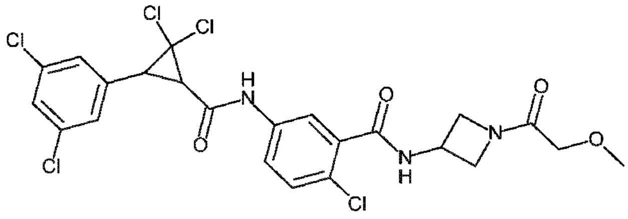 |
| 1523 | 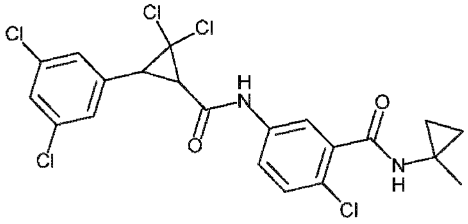 |
| 1524 | 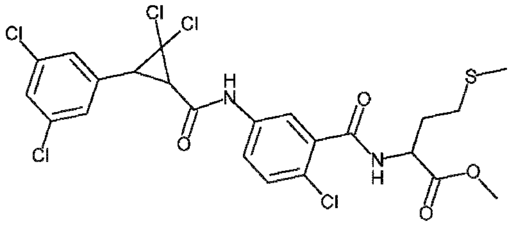 |

| | |
|---|---|
| **1525** | AND Enantiomer 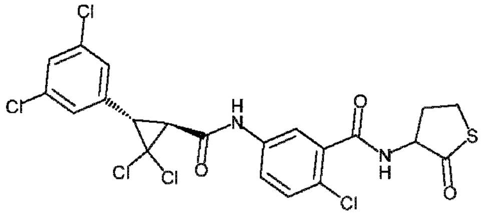 |
| **1526** | AND Enantiomer 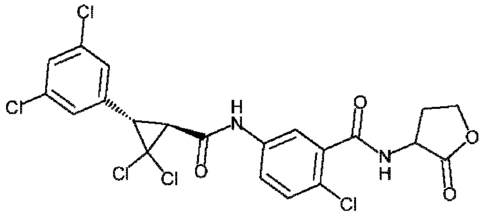 |
| **1527** | AND Enantiomer 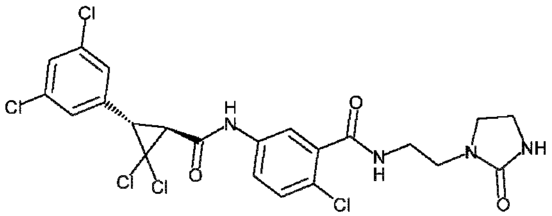 |
| **1528** | AND Enantiomer 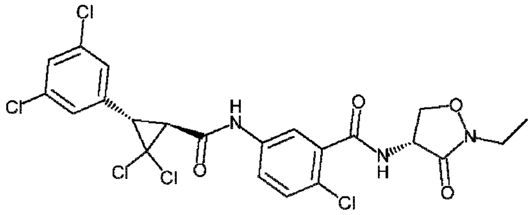 |
| **1529** | AND Enantiomer 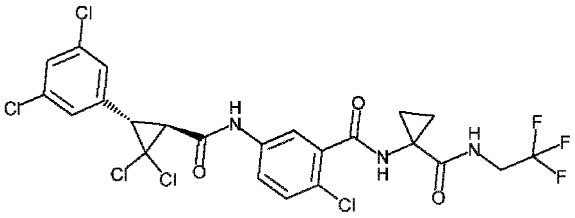 |

| | |
|---|---|
| 1530 | AND Enantiomer 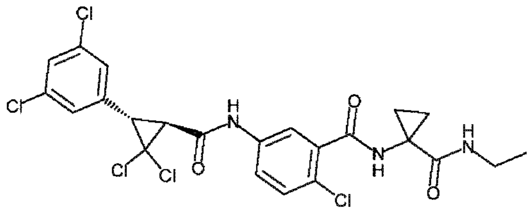 |
| 1531 | 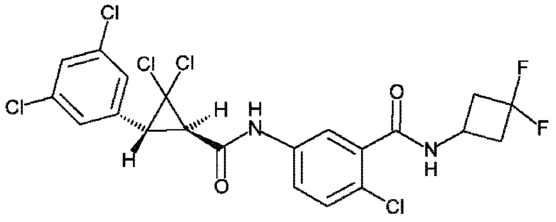 |
| 1532 | 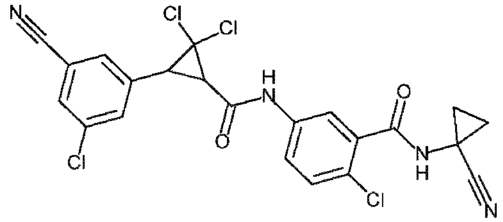 |
| 1533 | AND Enantiomer 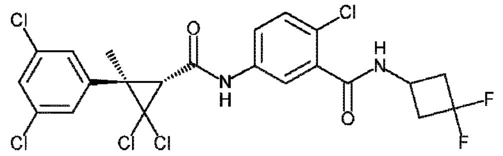 |
| 1534 | AND Enantiomer 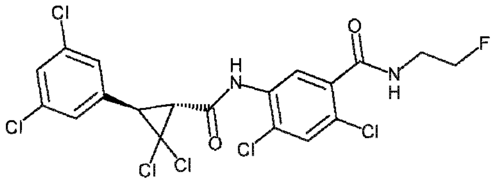 |

| | |
|---|---|
| 1535 | 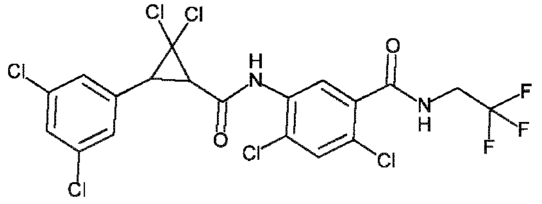 |
| 1536 | 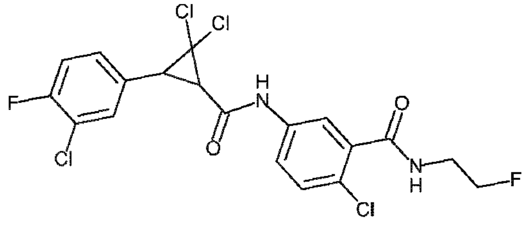 |
| 1537 | AND Enantiomer 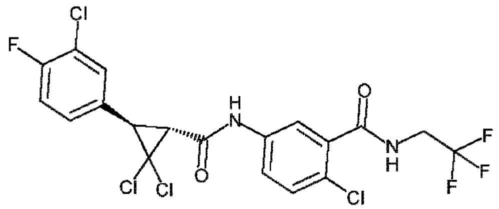 |
| 1538 | 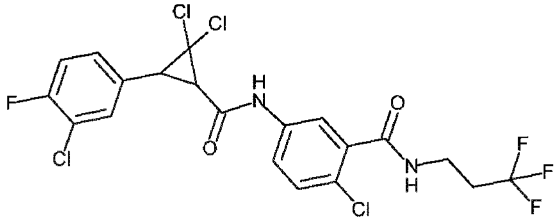 |
| 1539 | 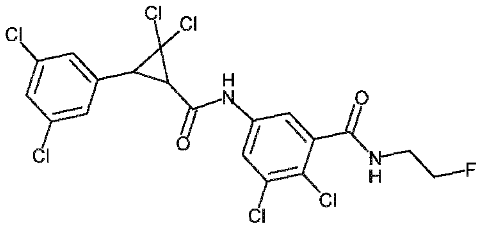 |

| | |
|---|---|
| 1540 | AND Enantiomer 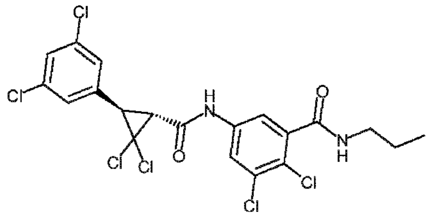 |
| 1541 | 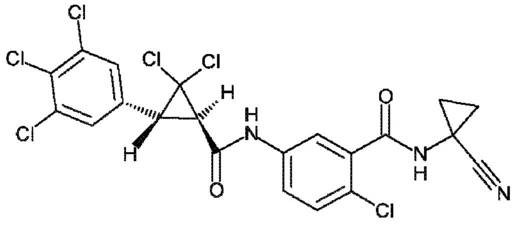 |
| 1542 | 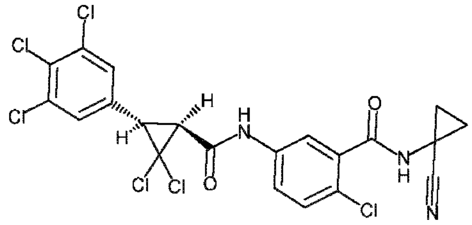 |
| 1543 | AND Enantiomer 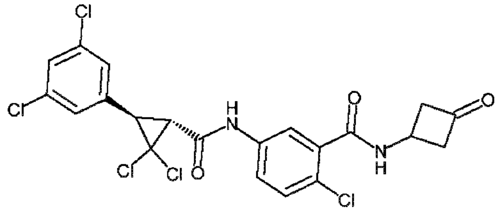 |
| 1544 | AND Enantiomer 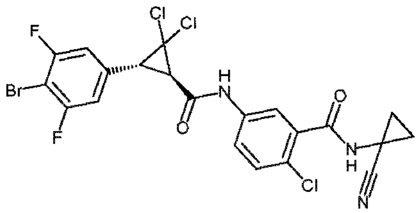 |

| | |
|---|---|
| 1545 | 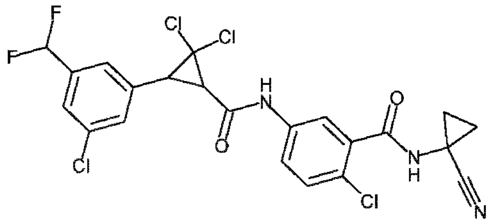 |
| 1546 | 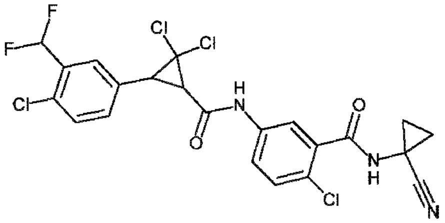 |
| 1547 | 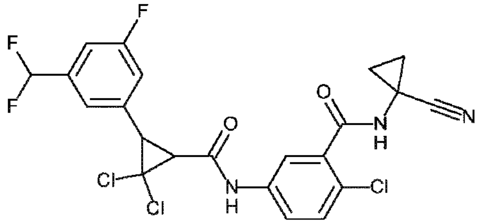 |
| 1548 | 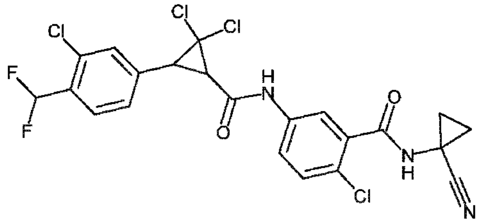 |
| 1549 | AND Enantiomer 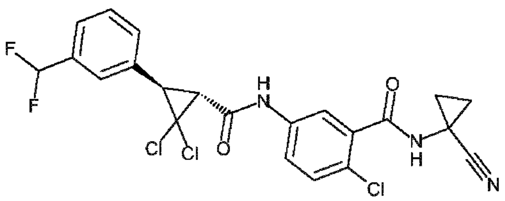 |

| | |
|---|---|
| 1550 | 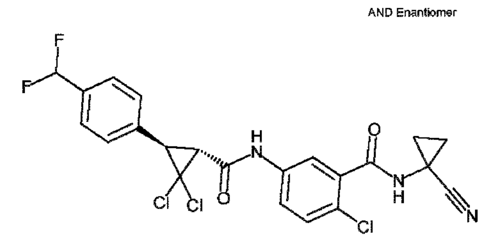 |
| 1551 | 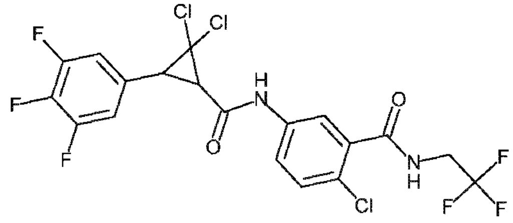 |
| 1552 | 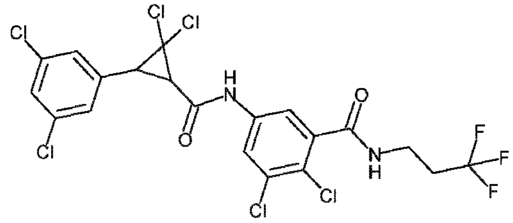 |
| 1553 | 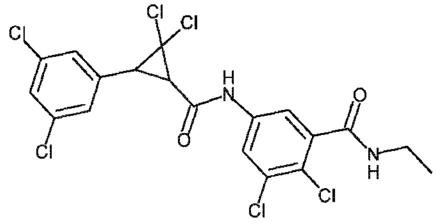 |
| 1554 | 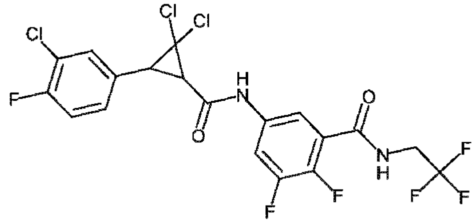 |

| | |
|---|---|
| 1555 | 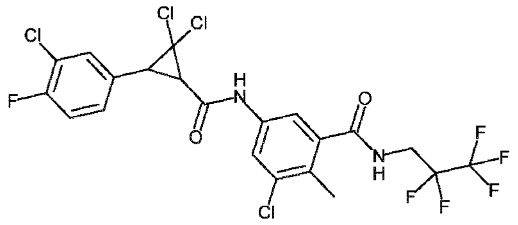 |
| 1556 | 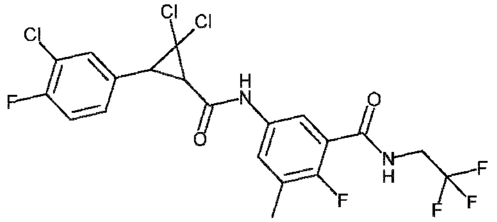 |
| 1557 | 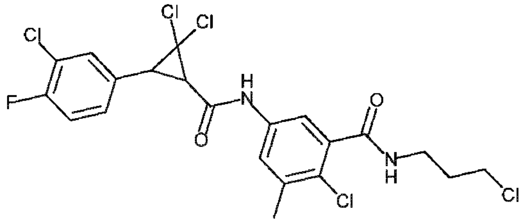 |
| 1558 | 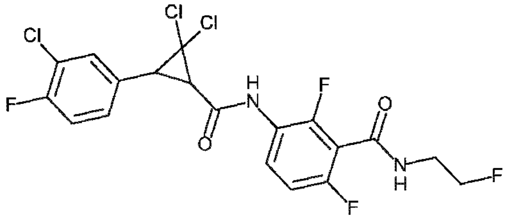 |
| 1559 | 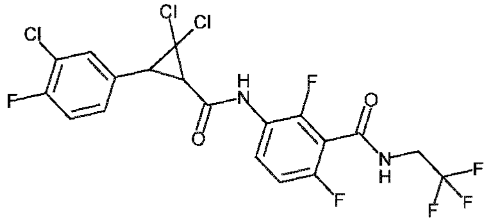 |

| | |
|---|---|
| 1560 | 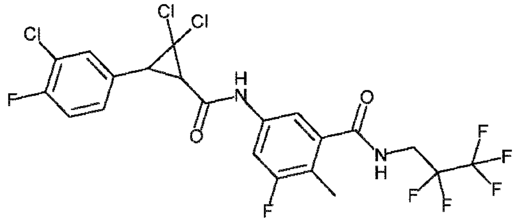 |
| 1561 | 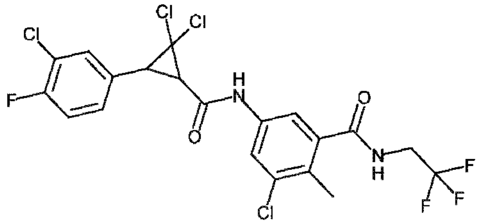 |
| 1562 | 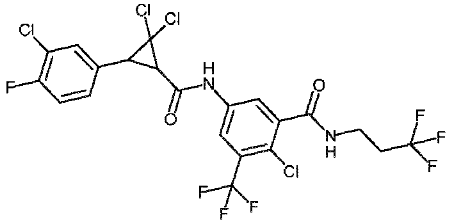 |
| 1563 | 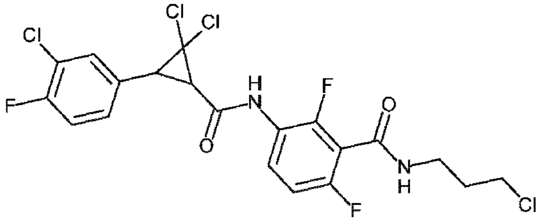 |
| 1564 | 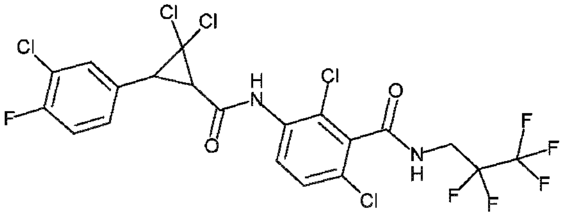 |

| | |
|---|---|
| 1565 | 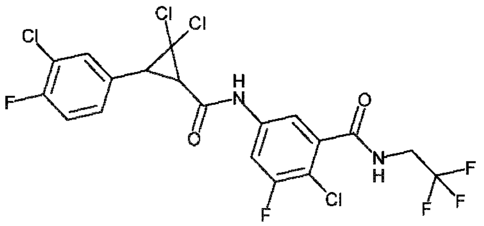 |
| 1566 | 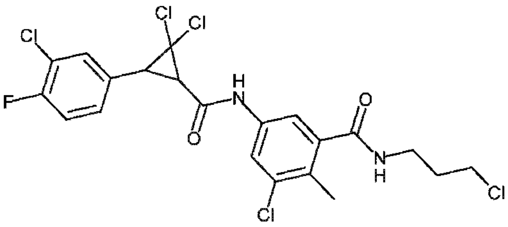 |
| 1567 | 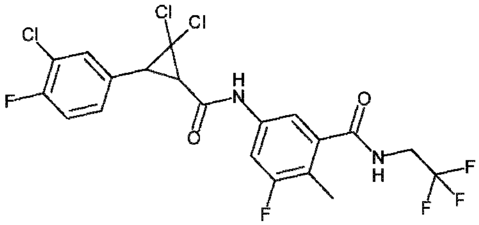 |
| 1568 | 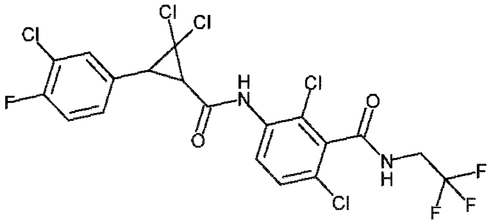 |
| 1569 | 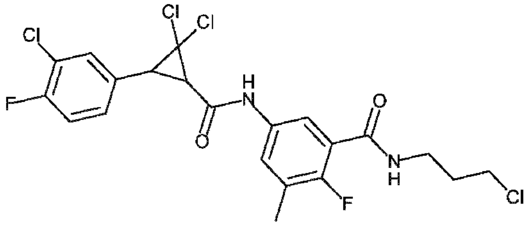 |

| | |
|---|---|
| 1570 | 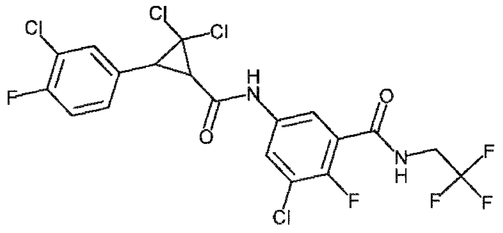 |
| 1571 | 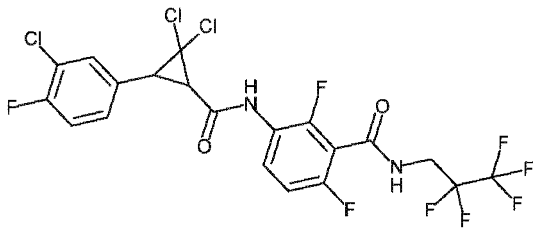 |
| 1572 | 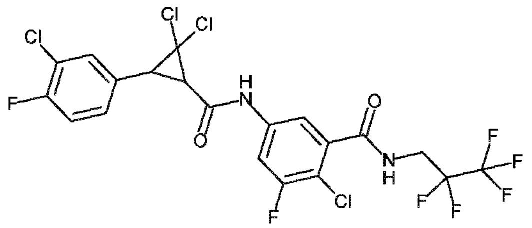 |
| 1573 | 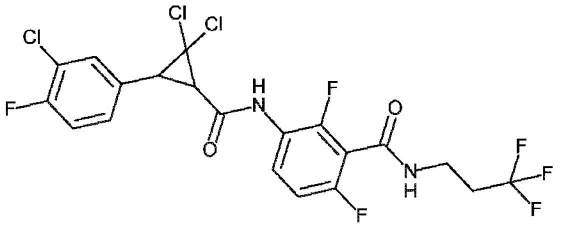 |
| 1574 | 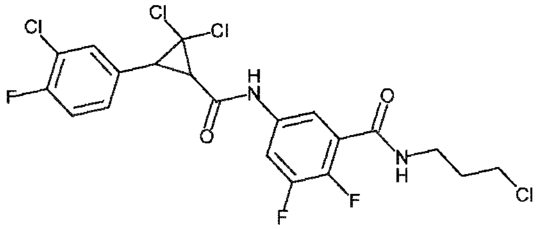 |

| | |
|---|---|
| 1575 | 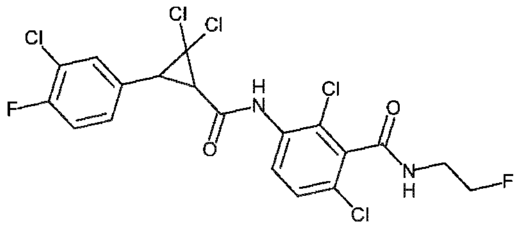 |
| 1576 | 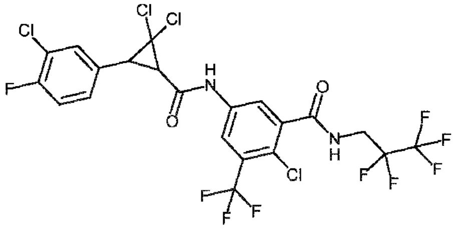 |
| 1577 | 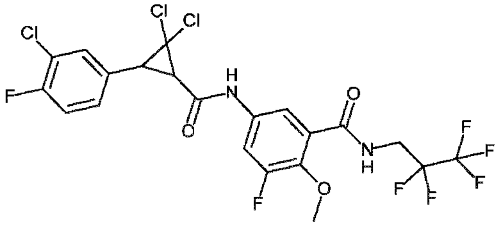 |
| 1578 | 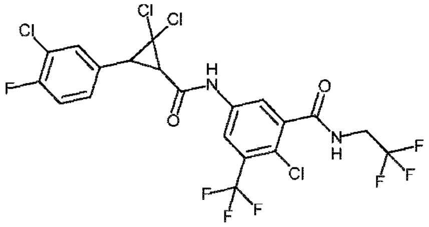 |
| 1579 | 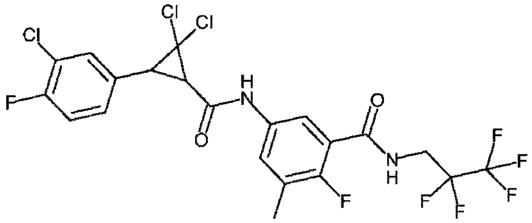 |

| | |
|---|---|
| 1580 | 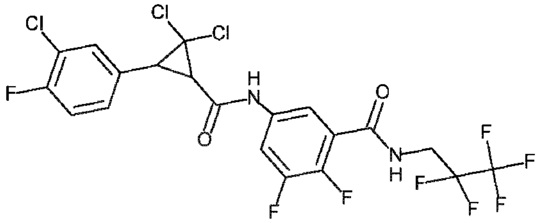 |
| 1581 | 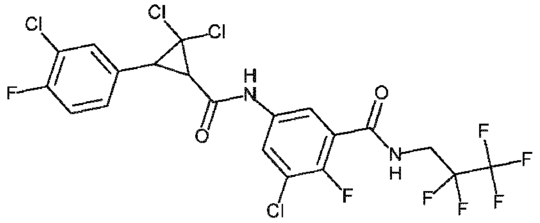 |
| 1582 | 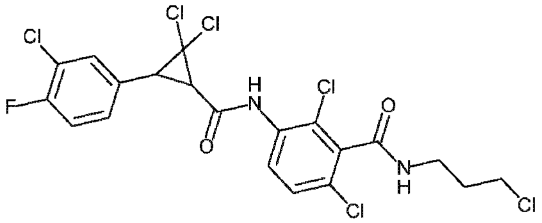 |
| 1583 | 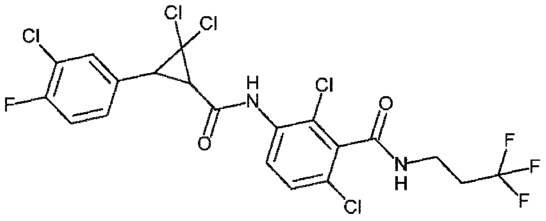 |
| 1584 | 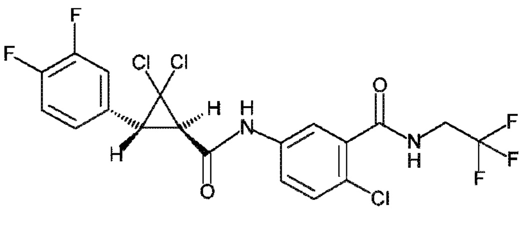 |

| | |
|---|---|
| 1585 | 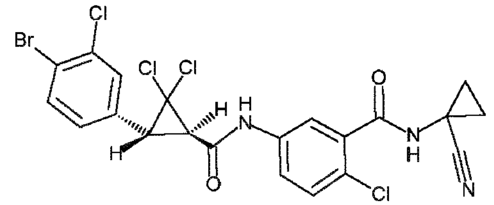 |
| 1586 | 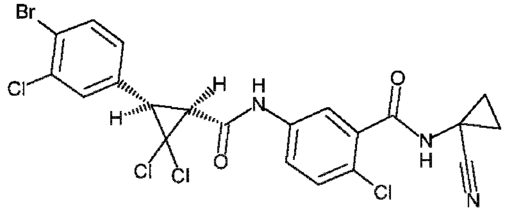 |
| 1587 | 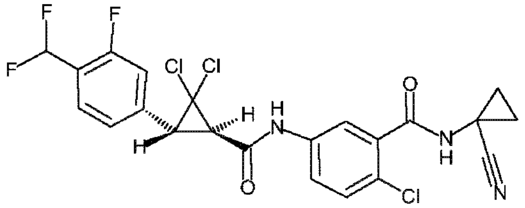 |
| 1588 | 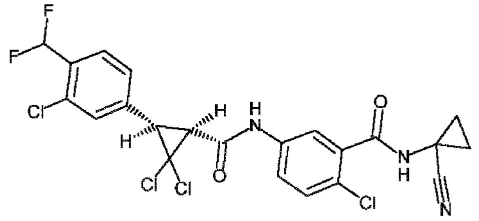 |
| 1589 | 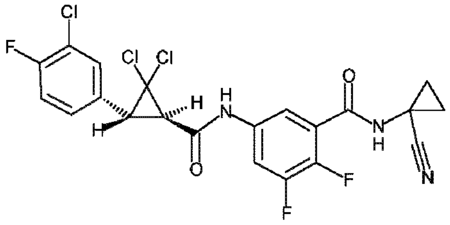 |

| | |
|---|---|
| 1590 | 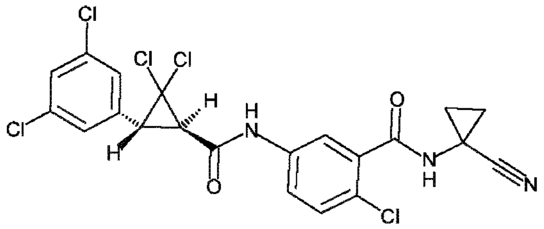 |
| 1591 | 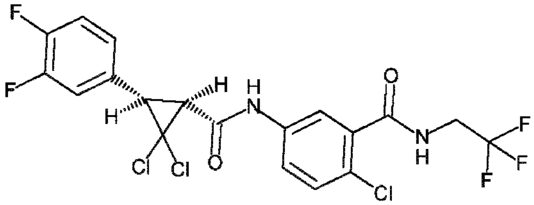 |
| 1592 | 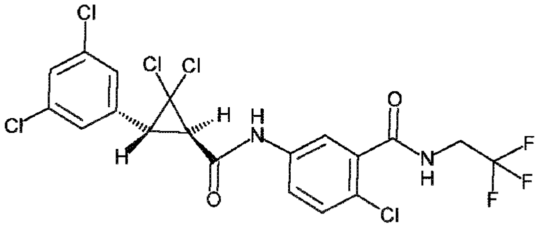 |
| 1593 | 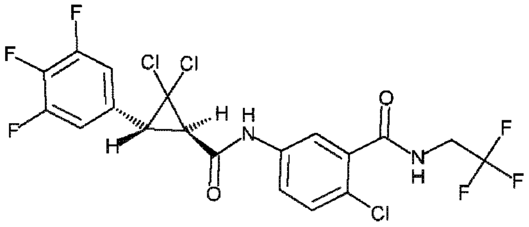 |
| 1594 | 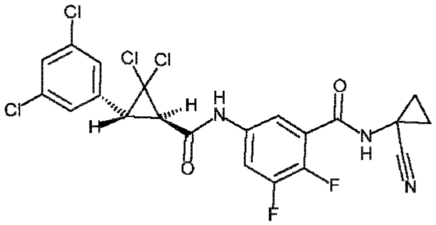 |

| | |
|---|---|
| 1600 | 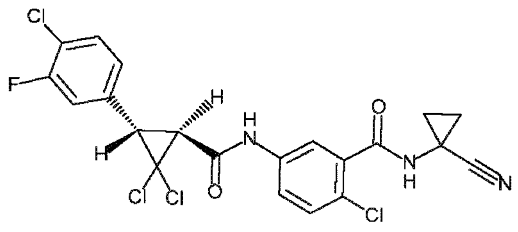 |
| 1601 | 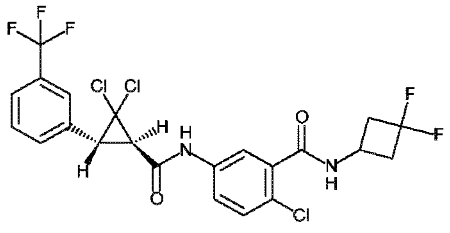 |
| 1602 | 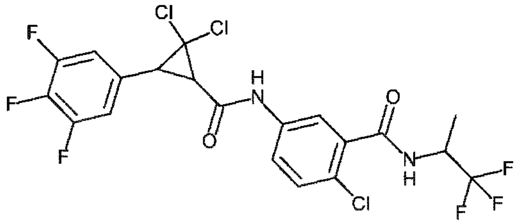 |
| 1603 | 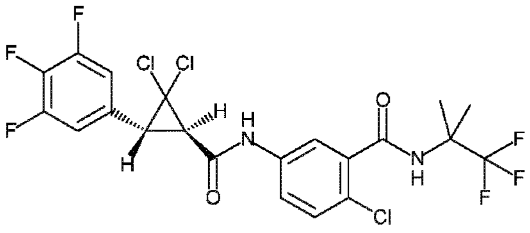 |
| 1604 | 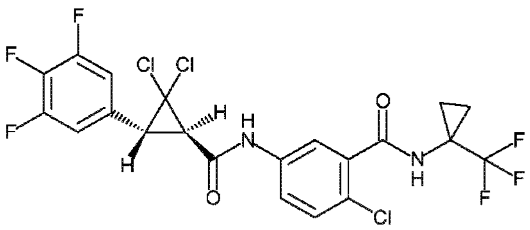 |

| | |
|---|---|
| 1605 | 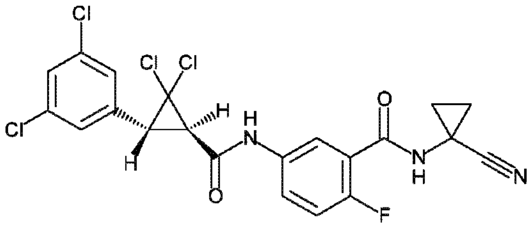 |
| 1606 | 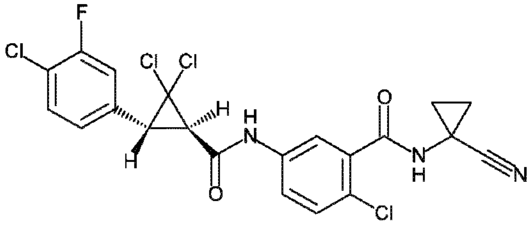 |
| 1607 | 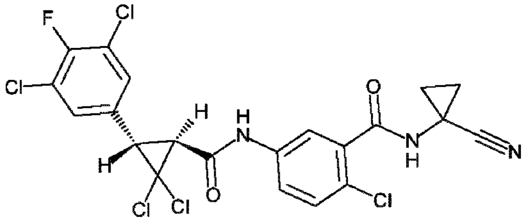 |
| 1608 | 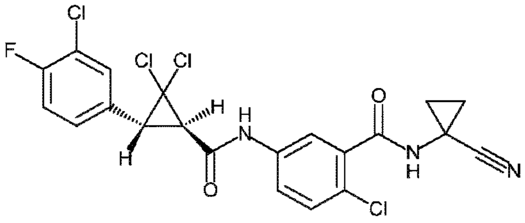 |
| 1609 | 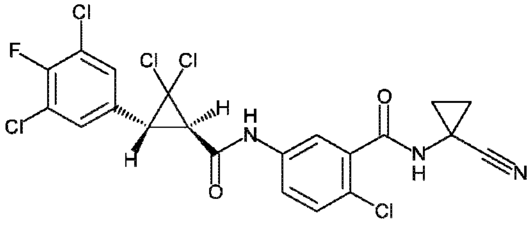 |

| | |
|---|---|
| 1610 | 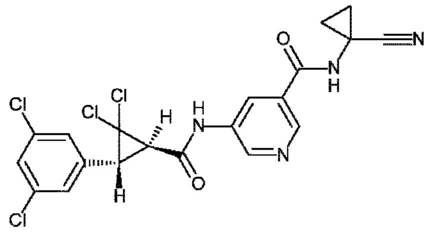 |
| 1611 | 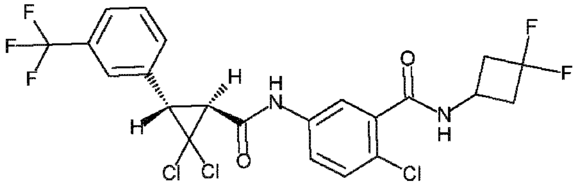 |
| 1612 | 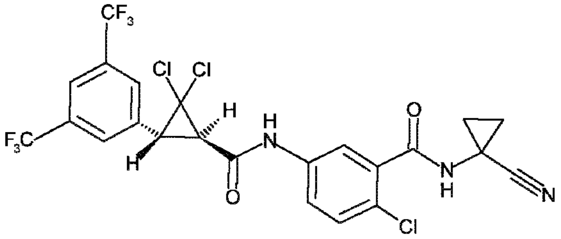 |
| 1613 | 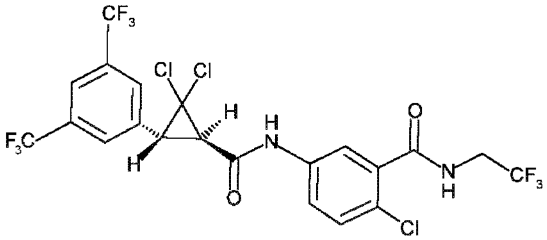 |
| 1614 | 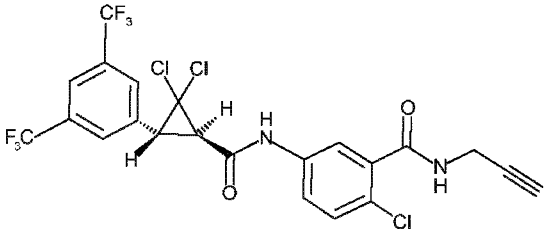 |

| | |
|---|---|
| 1615 | 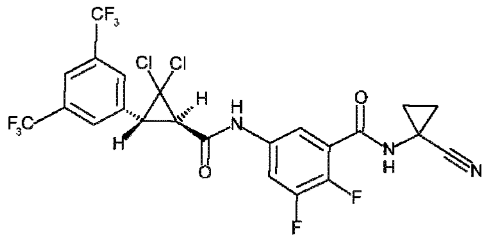 |
| 1616 | 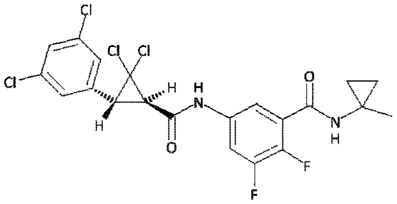 |
| 1617 | 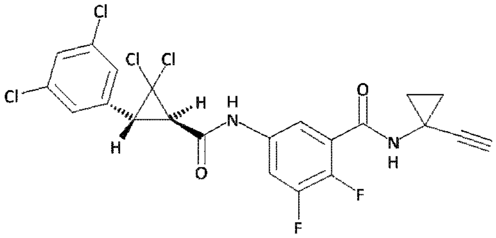 |
| 1618 | 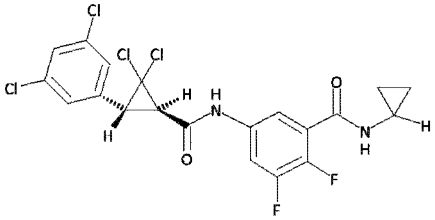 |
| 1619 | 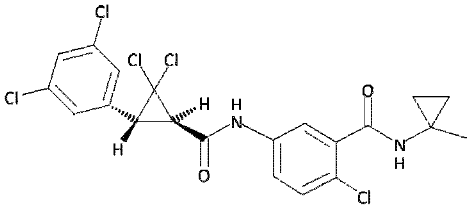 |

| | |
|---|---|
| 1620 | 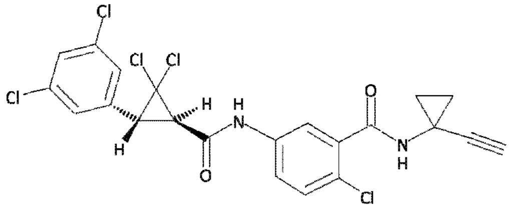 |
| 1621 | 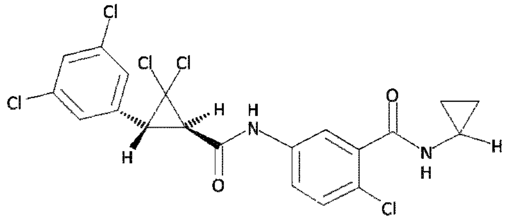 |
| 1622 | 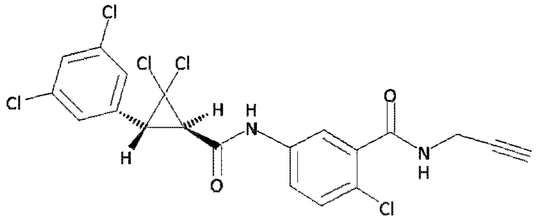 |
| 1623 | 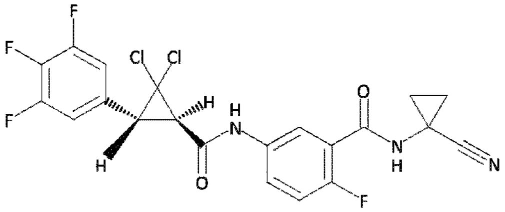 |
| 1624 | 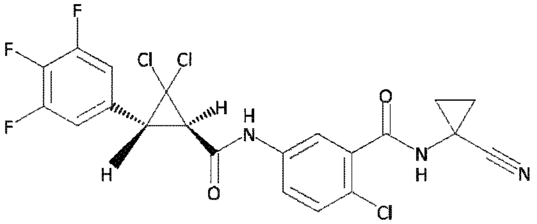 |

| | |
|---|---|
| 1625 | 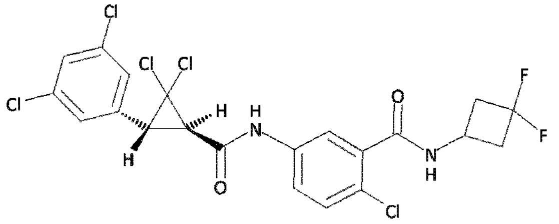 |
| 1626 | 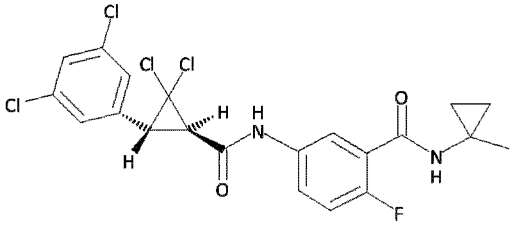 |
| 1627 | 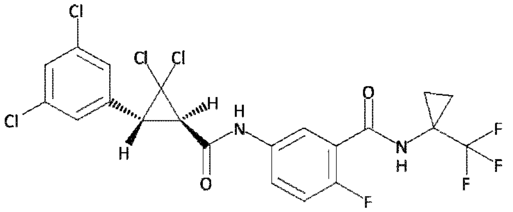 |
| 1628 | 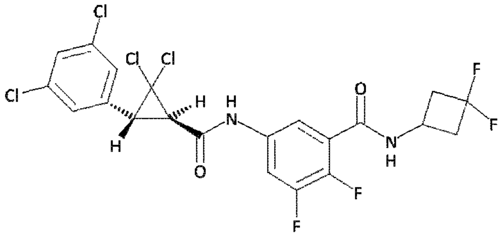 |
| 1629 | 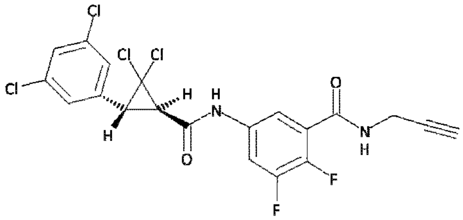 |

| | |
|---|---|
| 1630 | 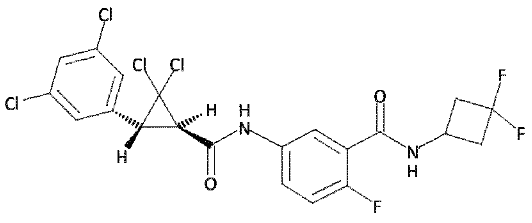 |
| 1631 | 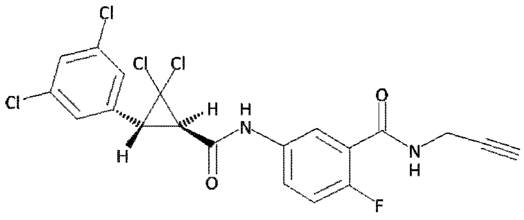 |
| 1632 | 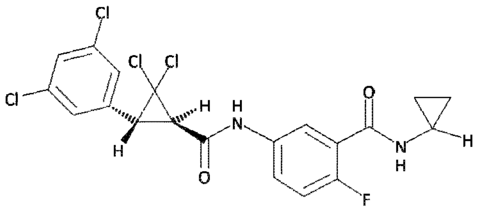 |
| 1633 | 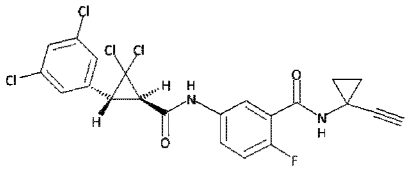 |

CYCLOPROPYLAMIDE COMPOUNDS AGAINST PARASITES IN FISH

CROSS-REFERENCE TO RELATED APPLICATIONS

This is a U.S. National Phase entry under 35 U.S.C. § 371 of International Patent Application No. PCT/EP2022/051751, filed Jan. 26, 2022, which published as WO2022/162001 on Aug. 4, 2022, which claims priority to EP application Ser. Nos. 21153646.1, filed Jan. 27, 2021, and EP 21212467.1, filed Dec. 6, 2021; the content of each of which is hereby incorporated by reference in its entirety.

FIELD OF INVENTION

The present invention relates to the treatment or prevention of parasitic infestations of animals.

BACKGROUND OF THE INVENTION

Infestation of fish by parasites is a major problem for commercial fish farming. Fish farmers who are confronted with a parasite problem usually suffer substantial financial losses and carry additional expenses.

Sea lice are ectoparasites that belong to the sub-class of copepoda which affect fish, particularly farmed salmonids, negatively by feeding on the mucus, skin, tissue, and blood of the fish host. Sea lice can cause significant harm (i.e., serious fin damage, skin erosion, bleeding, and open wounds) to host fish. Additionally, sea lice can cause chronic stress response in fish, which in turn can make them susceptible to other diseases. In addition, it appears that the sea lice have immunomodulatory effects on the host fish and can function as a vector in the transmission of other fish diseases. Damages due to parasitic infestations from sea lice result in considerable animal welfare issues, fish losses and increased expense. Infestation with sea lice is considered one of the most important disease problems in salmonid farming, especially Atlantic salmon (*Salmo salar*) and rainbow trout (*Oncorhynchus mykiss*).

Infestation with sea lice can also occur in other fish species, for example, sea bass, tilapia, carp, and the like. In addition to the costs that are associated with treatment, lower classification ratings of slaughtered fish and reduced growth rate due to reduced feed intake contribute to the economic losses.

Sea lice are meanwhile widely prevalent and encountered in all fish farms. Severe infestation kills the fish. Mortality rates of over 50%, based on sea lice infestation, have been reported from Norwegian fish farms. The extent of the damage depends on the time of year and on environmental factors, for example the salinity of the water and average water temperature. In a first phase, sea lice infestation is seen in the appearance of the parasites attached to the fish and later—even more clearly—from the damage caused to skin and tissue. The most severe damage is observed in smolts which are just in the phase in which they change from fresh water to sea water. The situation is made even worse by the specific conditions in the fish farms, where salmon of different age groups but of the same weight class are kept together; where fouled nets or cages are used; where high salt concentrations are to be found; where flow through the nets and cages is minimal and the fish are kept in a very narrow space.

There are a number of treatments already on the market for controlling sea lice including bath treatments, such as organophosphates (for example, dichlorvos and azamethiphos) and pyrethroids (for example, cypermethrin and deltamethrin), and in-feed-treatments, such as avermectins (for example, ivermectin and emamectin benzoate) and growth regulators (for example, lufenuron and teflubenzuron). However, resistance to many of these treatments has been observed and therefore, a need for new treatments remains, in particular treatments having a long duration of action.

Accordingly, a need still exists for new treatment options to control sea lice infestations on fish, particularly in farmed fish populations, that is safe and selective against the target parasite and is capable of treating sea lice populations showing resistance or reduced sensitivity to the current products. The present invention provides a new treatment option for controlling sea lice on fish.

International patent applications WO2016/168056, WO2016/168058, WO 2016/168059 and WO2018/071327 disclose certain compounds as having insecticidal and acaricidal activity and therefore, being useful in controlling agricultural plant pests. However, none of these citations exemplify or describe their use in aquaculture.

It has surprisingly been found that aliphatic cyclopropyl amide compounds of Formula (I) are effective to control parasite infestations of fish, especially sea lice infestations.

SUMMARY OF THE INVENTION

In a first aspect the invention is directed to compounds of

Formula (I)

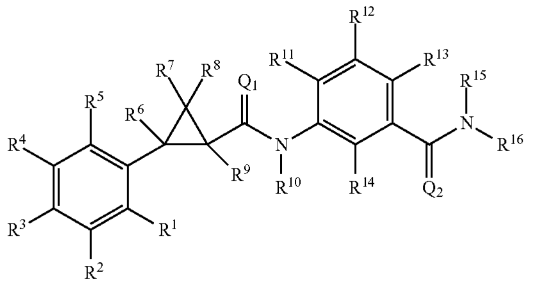

and N-oxides, veterinary acceptable acid addition salts, salt derivatives, solvates, ester derivatives, crystal polymorphs, isotopes, stereoisomers, and tautomers, for use in a method to control a parasite infestation in fish wherein $R^1$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^2$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$ haloalkyl, $(C_1\text{-}C_6)$alkyl-$S(O)_2NH_2$, $(C_1\text{-}C_6)$haloalkyl-$S(O)_2NH_2$, and S-(Halo)$_5$;

$R^3$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, $(C_1\text{-}C_6)$haloalkyl-$S(O)_2NH_2$, and S-(Halo)$_5$;

$R^4$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, $(C_1\text{-}C_6)$haloalkyl-$S(O)_2NH_2$, and S-(Halo)$_5$;

$R^5$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^6$ is selected from the group consisting of H and $(C_1\text{-}C_6)$alkyl;

$R^7$ is selected from the group consisting of H, F, Cl, Br, and I;

$R^8$ is selected from the group consisting of F, Cl, Br, and I;

$R^9$ is selected from the group consisting of H and $(C_1\text{-}C_6)$alkyl;

$R^{10}$ is selected from the group consisting of H, $(C_1\text{-}C_6)$alkyl, $(C_2\text{-}C_6)$alkenyl, $(C_1\text{-}C_6)$haloalkyl, $(C_1\text{-}C_6)$alkyl$(C_1\text{-}C_6)$alkoxy, C(=O)$(C_1\text{-}C_6)$alkyl, and $(C_1\text{-}C_6)$alkoxyC(=O)$(C_1\text{-}C_6)$alkyl;

$R^{11}$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^{12}$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^{13}$ is selected from the group consisting of H, F, Cl, Br, I, CN, $NH_2$, $NO_2$, CHO, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, $(C_1\text{-}C_6)$haloalkyl-$S(O)_2NH_2$, and triazolyl;

$R^{14}$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^{15}$ is selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_1\text{-}C_6)$alkyl$(C_1\text{-}C_6)$alkoxy, C(=O)$(C_1\text{-}C_6)$alkyl, and $(C_1\text{-}C_6)$alkoxyC(=O)$(C_1\text{-}C_6)$alkyl;

$R^{16}$ is selected from the group consisting of $(C_1\text{-}C_8)$alkyl, $(C_3\text{-}C_8)$cycloalkyl, $(C_1\text{-}C_8)$alkyl-O—$(C_1\text{-}C_8)$alkyl, $(C_1\text{-}C_8)$alkyl$(C_3\text{-}C_8)$cycloalkyl, $(C_1\text{-}C_8)$alkylphenyl, $(C_2\text{-}C_8)$alkenyl, $(C_2\text{-}C_8)$alkynyl, $(C_1\text{-}C_8)$haloalkyl, $(C_1\text{-}C_8)$alkyl-S—$(C_1\text{-}C_8)$alkyl, $(C_1\text{-}C_8)$alkyl-S(O)—$(C_1\text{-}C_8)$alkyl, $(C_1\text{-}C_8)$alkyl-$S(O)_2$—$(C_1\text{-}C_8)$alkyl, O-phenyl, O—$(C_2\text{-}C_8)$alkenyl, O—$(C_1\text{-}C_8)$alkyl$(C_3\text{-}C_8)$cycloalkyl, O—$(C_1\text{-}C_8)$alkylphenyl, $(C_1\text{-}C_8)$alkyl-O—$(C_1\text{-}C_8)$alkyl$(C_3\text{-}C_8)$cycloalkyl, $(C_1\text{-}C_8)$alkyl-O—$(C_1\text{-}C_8)$haloalkyl, $(C_1\text{-}C_8)$alkyl-C(=O)NH—$(C_1\text{-}C_8)$haloalkyl, $(C_1\text{-}C_8)$alkyl-NHC(O)—$(C_1\text{-}C_8)$alkyl, $(C_1\text{-}C_8)$alkyl-S—$(C_1\text{-}C_8)$haloalkyl, $(C_1\text{-}C_8)$alkyl-S(O)—$(C_1\text{-}C_8)$haloalkyl, $(C_1\text{-}C_8)$alkyl-$S(O)_2$—$(C_1\text{-}C_8)$haloalkyl, and $(C_1\text{-}C_8)$alkyl-$S(O)_2$—$NH_2$, wherein each alkyl, alkenyl, alkynyl, alkyl-cycloalkyl, haloalkyl, and phenyl, may be optionally substituted with one or more substituents selected from the group consisting of F, Cl, Br, I, CN, OH, $NH_2$, $NO_2$, $(C_1\text{-}C_8)$alkyl, $(C_2\text{-}C_8)$alkenyl, $(C_2\text{-}C_8)$alkynyl, $(C_1\text{-}C_8)$alkoxy, $(C_1\text{-}C_8)$haloalkyl, $N((C_1\text{-}C_8)alkyl)_2$, C(O)O$(C_1\text{-}C_8)$alkyl, benzothioenyl, oxoimidazolidinyl, furanyl, pyrazolyl, pyridinyl, thiazolyl, and triazolyl;

$R^{15}$ and $R^{16}$ together can optionally form a 2- to 5-membered saturated or unsaturated, hydrocarbyl link, which may contain one or more heteroatoms selected from the group consisting of nitrogen, sulfur, and oxygen, wherein said hydrocarbyl link may be optionally substituted with one or more substituents selected from the group consisting of F, Cl, Br, I, CN, $NH_2$, and $NO_2$;

or $R^{16}$ is selected from the group consisting of $(C_3\text{-}C_8)$cycloalkyl, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, wherein each cycloalkyl, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl may be optionally substituted with one or more substituents selected from the group consisting of H, F, Cl, Br, I, CN, $NH_2$, $NO_2$, oxo, $(C_1$-$C_4)$alkyl, $(C_1$-$C_4)$haloalkyl, C(=O)O$(C_1$-$C_4)$alkyl, (C=O)NH$(C_1$-$C_4)$alkyl, (C=O)NH$(C_1$-$C_4)$haloalkyl, C(=O)$(C_3$-$C_6)$cyclopropyl, C(=O)$(C_1$-$C_4)$haloalkyl, C(=O)$(C_1$-$C_4)$alkyl$(C_1$-$C_4)$alkoxy, and $(C_1$-$C_4)$alkyl-morpholinyl;

$Q^1$ and $Q^2$ are each independently selected from the group consisting of O and S.

Suitably compounds for use according to the invention and embodiments thereof are compounds wherein $R^{16}$ is selected from the group consisting of $(C_1$-$C_8)$alkyl, $(C_3$-$C_8)$cycloalkyl, $(C_1$-$C_8)$alkyl-O—$(C_1$-$C_8)$alkyl, $(C_1$-$C_8)$alkyl$(C_3$-$C_8)$cycloalkyl, $(C_1$-$C_8)$alkylphenyl, $(C_2$-$C_8)$alkenyl, $(C_2$-$C_8)$alkynyl, $(C_1$-$C_8)$haloalkyl, $(C_1$-$C_8)$alkyl-S—$(C_1$-$C_8)$alkyl, $(C_1$-$C_8)$alkyl-S(O)—$(C_1$-$C_8)$alkyl, $(C_1$-$C_8)$alkyl-$S(O)_2$—$(C_1$-$C_8)$alkyl, O- phenyl, O—$(C_2$-$C_8)$alkenyl, O—$(C_1$-$C_8)$alkyl$(C_3$-$C_8)$cycloalkyl, O—$(C_1$-$C_8)$alkylphenyl, $(C_1$-$C_8)$alkyl-O—$(C_1$-$C_8)$alkyl$(C_3$-$C_8)$cycloalkyl, $(C_1$-$C_8)$alkyl-O—$(C_1$-$C_8)$haloalkyl, $(C_1$-$C_8)$alkyl-C(=O)NH—$(C_1$-$C_8)$haloalkyl, $(C_1$-$C_8)$alkyl-NHC(O)—$(C_1$-$C_8)$alkyl, $(C_1$-$C_8)$alkyl-S—$(C_1$-$C_8)$haloalkyl, $(C_1$-$C_8)$alkyl-S(O)—$(C_1$-$C_8)$haloalkyl, $(C_1$-$C_8)$alkyl-$S(O)_2$—$(C_1$-$C_8)$haloalkyl, $(C_1$-$C_8)$alkyl-$S(O)_2$—$NH_2$, and a heterocycle, wherein each alkyl, alkenyl, alkynyl, alkyl-cycloalkyl, haloalkyl, and phenyl, may be optionally substituted with one or more substituents selected from the group consisting of F, Cl, Br, I, CN, OH, $NH_2$, $NO_2$, $(C_1$-$C_8)$alkyl, $(C_2$-$C_8)$alkenyl, $(C_2$-$C_8)$alkynyl, $(C_1$-$C_8)$alkoxy, $(C_1$-$C_8)$haloalkyl, $N((C_1$-$C_8)alkyl)_2$, C(O)O$(C_1$-$C_8)$alkyl, benzothioenyl, oxoimidazolidinyl, furanyl, pyrazolyl, pyridinyl, thiazolyl, and triazolyl, and wherein the heterocycle is selected from the group consisting of, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, and wherein each $(C_3$-$C_8)$cycloalkyl and heterocycle may be optionally substituted with one or more substituents selected from the group consisting of H, F, Cl, Br, I, CN, $NH_2$, $NO_2$, oxo, $(C_1$-$C_4)$alkyl, $(C_2$-$C_8)$alkenyl, $(C_2$-$C_8)$alkynyl, $(C_1$-$C_4)$haloalkyl, C(=O)O$(C_1$-$C_4)$alkyl, (C=O)NH$(C_1$-$C_4)$alkyl, (C=O)NH$(C_1$-$C_4)$haloalkyl, C(=O)$(C_3$-$C_6)$cyclopropyl, C(=O)$(C_1$-$C_4)$haloalkyl, C(=O)$(C_1$-$C_4)$alkyl$(C_1$-$C_4)$alkoxy, and $(C_1$-$C_4)$alkyl-morpholinyl.

Suitably compounds for use according to the invention and embodiments thereof are compounds wherein $R^{16}$ is selected from the group consisting of $(C_1$-$C_8)$alkyl, $(C_3$-$C_8)$cycloalkyl, $(C_1$-$C_8)$alkyl-O—$(C_1$-$C_8)$alkyl, $(C_1$-$C_8)$alkyl$(C_3$-$C_8)$cycloalkyl, $(C_2$-$C_8)$alkenyl, $(C_2$-$C_8)$alkynyl, $(C_1$-$C_8)$haloalkyl, $(C_1$-$C_8)$alkyl- S—$(C_1$-$C_8)$alkyl, $(C_1$-$C_8)$alkyl-S(O)—$(C_1$-$C_8)$alkyl, $(C_1$-$C_8)$alkyl-$S(O)_2$—$(C_1$-$C_8)$alkyl, $(C_1$-$C_8)$alkyl-O—$(C_1$- $C_8)$haloalkyl, $(C_1$-$C_8)$alkyl-S—$(C_1$-$C_8)$haloalkyl, $(C_1$-$C_8)$alkyl-S(O)—$(C_1$-$C_8)$haloalkyl, $(C_1$-$C_8)$alkyl-$S(O)_2$—$(C_1$-$C_8)$haloalkyl, and $(C_1$-$C_8)$alkyl-$S(O)_2$—$NH_2$, and a heterocycle wherein each alkyl, alkenyl, alkynyl, alkyl-cycloalkyl, and haloalkyl, may be optionally substituted with one or more substituents selected from the group consisting of F, Cl, Br, I, CN, OH, $NH_2$, $NO_2$, $(C_1$-$C_8)$alkyl, $(C_2$-$C_8)$alkenyl, $(C_2$-$C_8)$alkynyl, $(C_1$-$C_8)$alkoxy, $(C_1$-$C_8)$haloalkyl, C(O)O$(C_1$-$C_8)$alkyl, oxoimidazolidinyl, furanyl, and pyrazolyl.

Suitably compounds for use according to the invention and embodiments thereof are compounds wherein the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide.

Suitably compounds for use according to the invention and embodiments thereof are compounds wherein $R^{16}$ each $(C_3$-$C_8)$cycloalkyl, or heterocycle may be optionally substituted with one or more substituents selected from the group consisting of H, F, Cl, Br, I, CN, $NH_2$, $NO_2$, oxo, $(C_1$-$C_4)$alkyl, $(C_2$-$C_8)$alkenyl, $(C_2$-$C_8)$alkynyl, $(C_1$-$C_4)$haloalkyl, C(=O)O$(C_1$-$C_4)$alkyl, (C=O)NH$(C_1$-$C_4)$alkyl, (C=O)NH$(C_1$-$C_4)$haloalkyl, C(=O)$(C_3$-$C_6)$cyclopropyl, C(=O)$(C_1$-$C_4)$haloalkyl, C(=O)$(C_1$-$C_4)$alkyl$(C_1$-$C_4)$alkoxy, and $(C_1$-$C_4)$alkyl-morpholinyl.

Suitably compounds for use according to the invention and embodiments thereof are compounds wherein:

$R^1$ is selected from the group consisting of H F, and Cl;

$R^2$ is selected from the group consisting of H, F, Cl, Br, $CH_3$, and $CF_3$;

$R^3$ is selected from the group consisting of H, F, Cl, $CH_3$, and $CHF_2$, $CF_3$, $OCF_3$;

$R^4$ is selected from the group consisting of H, F, Cl, Br, $CH_3$, and $CF_3$;

$R^5$ is H;

$R^6$ is H;

$R^7$ is selected from the group consisting of Cl and Br;

$R^8$ is selected from the group consisting of Cl and Br;

$R^9$, $R^{10}$, and $R^{11}$ is H;

$R^{12}$ is selected from the group consisting H, F, Cl, Br, $CH_3$;

$R^{13}$ is selected from the group consisting of H, F, Cl, $CH_3$ and $CF_3$;

$R^{14}$ is H or F;

$R^{15}$ is selected from the group consisting of H and $CH_3$;

Q1 and Q2 are O.

In a suitable use of the invention and/or any embodiment thereof, the parasite infestation is a sea lice infestation.

In a suitable use of the invention and/or any embodiment thereof, the parasite is at least one of *Lepeophtheirus salmonis, Caligus celmensi, Caligus curtus, Caligus dussumieri, Caligus elongates, Caligus longicaudatus, Caligus rogercresseyi* or *Caligus stromii.*

In a suitable use of the invention and/or any embodiment thereof, the parasite infestation is with copepodites, pre-adult, or adult sea lice or a mixed infestation with various stages.

In a suitable use of the invention and/or any embodiment thereof, the rate of infestation of the fish is between 0.5 and 3 parasites on average per fish in a fish facility, preferably wherein the parasite is an adult female sea louse.

In a suitable use of the invention and/or any embodiment thereof, the method comprises administering to fish the compound of Formula (i) as defined in any of the claims 1 to 4 by oral administration, or by topical administration such as by bath treatment or by intraperitoneal or intramuscular injection.

In a suitable use of the invention and/or any embodiment thereof, the method comprises administering to fish the compound of Formula (i) as defined in any of the claims 1 to 4 by oral administration, wherein the oral administration comprises administering a medicated fish feed comprising a therapeutically effective amount the compound and fish feed.

In a suitable use of the invention and/or any embodiment thereof, the method comprises administering the compound of Formula (i) as defined in any of the claims 1 to 4, by bath treatment, wherein the bath treatment comprises immersion of fish in water with a therapeutically effective amount of a compound.

In a suitable use of the invention and/or any embodiment thereof, the fish is a salmonid.

The invention is also directed to a premix comprising a compound of Formula (I) as defined in any embodiment as described herein, wherein the premix further comprises nutrients.

Suitably, the premix comprises nutrients in the form of pellets wherein the pellets are coated with a composition comprising a compound of Formula (I) as defined in any embodiment described herein.

In a suitable embodiment, a medicated fish feed is provided comprising the premix as defined herein and fish feed.

In a preferred embodiment the parasite infestation is an infestation with sea lice.

In one embodiment the invention provides a composition comprising one or more compounds of Formula (I) according to any embodiment as described herein and veterinarily acceptable formulation auxiliaries for use to control parasitic infestations in a fish population.

Another embodiment is a premix comprising nutrients, formulation auxiliaries and at least one compound of Formula (I) according to any embodiment as described herein.

Another embodiment is a medicated fish feed comprising such composition according to any embodiment as described herein or premix and nutritional fish feed.

Further embodiments are directed to kits comprising such compound or composition according to any embodiment as described herein and instructions for administration of the composition to fish.

A preferred embodiment is directed to a kit comprising the premix according to any embodiment as described herein and instructions for preparation of medicated fish feed and/or instructions for administration of the medicated fish feed to a fish population for use in the control of sea lice infestation.

Another preferred embodiment is directed to a kit comprising a stock solution according to any embodiment as described herein and instructions for preparation of medicated water for a bath treatment, and/or instructions for immersion of fish to control sea lice infestation.

DETAILED DESCRIPTION

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only.

This invention, therefore, is not limited to the preferred embodiments described in this specification and may be variously modified. In addition, for conciseness purposes and readability only some combinations of embodiments are explicitly described, however it should be understood that other combinations of embodiments are also contemplated.

The inventors of the current invention discovered that parasites, especially sea lice infestations of fish, can be treated or prevented by administering an effective amount of an aliphatic cyclopropyl amide compound of Formula (I).

The benefits of such method are that such method is effective in both treating existing sea lice infestations and preventing new infestations and thus prevent the establishment of an adult sea lice colony, which is known to be the most damaging stage. The resistance breaking properties of such compounds are very favorable.

Surprisingly, it has been found that the aliphatic cyclopropyl amide compounds of Formula (I) are effective and can be successfully used against juvenile and adult stages of sea lice on fish while having low toxicity to fish.

A further advantageous property of the aliphatic cyclopropyl amide compounds of Formula (I) is that, at the proposed concentrations, other marine animals such as lobsters, oysters, crustaceans (with the exception of sea lice), fish and marine plants do not suffer injury.

As it has been shown in the examples, the administration of aliphatic cyclopropyl amide compounds of Formula (I) as described in this application, can effectively control sea lice infestations using oral administration, and especially when using medicated feed administration comprising a compound of the invention and fish feed. Furthermore, it has been shown that compounds of Formula (I) can be effectively used to control resistant populations of fish parasites.

Hence the current invention would be an advancement in the control of fish parasites, especially sea lice, allowing effective control of sea lice in fish populations.

Compounds of Formula (I) can be used to control parasite infestations in fish. The use according to the current invention is described below in more detail Compounds of Formula (I), re in the following called aliphatic cyclopropyl amide compounds of Formula (I), or compounds or compounds according to the/this invention.

Therefore the present invention is directed to a compound of the following formula Formula (I)

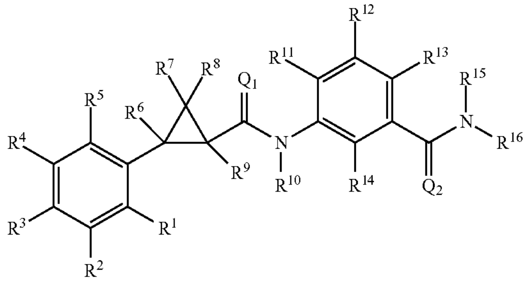

and N-oxides, veterinary acceptable acid addition salts, salt derivatives, solvates, ester derivatives, crystal polymorphs, isotopes, stereoisomers, and tautomers, for use in a method to control a parasite infestation in fish wherein $R^1$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$ haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^5$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^6$ is selected from the group consisting of H and $(C_1-C_6)$alkyl;

$R^7$ is selected from the group consisting of H, F, Cl, Br, and I;

$R^8$ is selected from the group consisting of F, Cl, Br, and I;

$R^9$ is selected from the group consisting of H and $(C_1-C_6)$alkyl;

$R^{10}$ is selected from the group consisting of H, $(C_1-C_6)$alkyl, $(C_2-C_6)$alkenyl, $(C_1-C_6)$haloalkyl, $(C_1-C_6)$alkyl$(C_1-C_6)$alkoxy, $C(=O)(C_1-C_6)$alkyl, and $(C_1-C_6)$alkoxy$C(=O)(C_1-C_6)$alkyl;

$R^{11}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^{12}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^{13}$ is selected from the group consisting of H, F, Cl, Br, I, CN, $NH_2$, $NO_2$, CHO, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and triazolyl;

$R^{14}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^{15}$ is selected from the group consisting of H, $(C_1-C_6)$alkyl, $(C_2-C_6)$alkenyl, $(C_2-C_6)$alkynyl, $(C_1-C_6)$haloalkyl, $(C_1-C_6)$alkyl$(C_1-C_6)$alkoxy, $C(=O)(C_1-C_6)$alkyl, and $(C_1-C_6)$alkoxy$C(=O)(C_1-C_6)$alkyl;

$R^{16}$ is selected from the group consisting of $(C_1-C_8)$alkyl, $(C_3-C_8)$cycloalkyl, $(C_1-C_8)$alkyl-O—$(C_1-C_8)$alkyl, $(C_1-C_8)$alkyl$(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, O-phenyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$cycloalkyl, $(C_1-C_8)$alkyl-O—$(C_1-C_8)$haloalkyl, $(C_1-C_8)$alkyl-C(=O)NH—$(C_1-C_8)$haloalkyl, $(C_1-C_8)$alkyl-NHC(O)—$(C_1-C_8)$alkyl, $(C_1-C_8)$alkyl-S—$(C_1-C_8)$haloalkyl, $(C_1-C_8)$alkyl-S(O)—$(C_1-C_8)$haloalkyl, $(C_1-C_8)$alkyl-$S(O)_2$—$(C_1-C_8)$haloalkyl, and $(C_1-C_8)$alkyl-$S(O)_2$—$NH_2$, wherein each alkyl, alkenyl, alkynyl, cycloalkyl, haloalkyl, and phenyl, may be optionally substituted with one or more substituents selected from the group consisting of F, Cl, Br, I, CN, OH, $NH_2$, $NO_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $N((C_1-C_8)alkyl)_2$, $C(O)O(C_1-C_8)$alkyl, benzothioenyl, oxoimidazolidinyl, furanyl, pyrazolyl, pyridinyl, thiazolyl, and triazolyl;

$R^{15}$ and $R^{16}$ together can optionally form a 2- to 5-membered saturated or unsaturated, hydrocarbyl link, which may contain one or more heteroatoms selected from the group consisting of nitrogen, sulfur, and oxygen, wherein said hydrocarbyl link may be optionally substituted with one or more substituents selected from the group consisting of F, Cl, Br, I, CN, $NH_2$, and $NO_2$;

or $R^{16}$ is selected from the group consisting of $(C_3-C_8)$cycloalkyl, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, wherein each cycloalkyl, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, C(=O)O$(C_1-C_4)$alkyl, (C=O)NH$(C_1-C_4)$alkyl, (C=O)NH$(C_1-C_4)$haloalkyl, C(=O)$(C_3-C_6)$cyclopropyl, C(=O)$(C_1-C_4)$haloalkyl, C(=O)$(C_1-C_4)$alkyl$(C_1-C_4)$alkoxy, and $(C_1-C_4)$alkyl-morpholinyl;

$Q^1$ and $Q^2$ are each independently selected from the group consisting of O and S.

In embodiment of the invention and/or embodiments thereof, $R^1$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, and $(C_1-C_6)$haloalkoxy.

In embodiment of the invention and/or embodiments thereof, $R^1$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$haloalkyl, and $(C_1-C_6)$haloalkoxy.

In embodiment of the invention and/or embodiments thereof, $R^1$ is selected from the group consisting of H, F, Cl, Br, I, CN, $NH_2$, $NO_2$, $(C_1-C_6)$alkyl, $(C_1-C_6)$alkoxy, $(C_1-C_6)$haloalkyl, and $(C_1-C_6)$haloalkoxy.

In embodiment of the invention and/or embodiments thereof, $R^1$ is selected from the group consisting of H, F, Cl, Br, I, CN, $NH_2$, $NO_2$, $(C_1-C_6)$alkyl, and $(C_1-C_6)$haloalkyl.

In embodiment of the invention and/or embodiments thereof, $R^1$ is selected from the group consisting of H, F, Cl, Br, I, $NH_2$, $(C_1-C_6)$alkyl, and $(C_1-C_6)$haloalkyl.

In embodiment of the invention and/or embodiments thereof, $R^1$ is selected from the group consisting of H, F, Cl, $(C_1-C_6)$alkyl, and $(C_1-C_6)$haloalkyl.

In embodiment of the invention and/or embodiments thereof, $R^1$ is selected from the group consisting of H, F, and Cl.

In embodiment of the invention and/or embodiments thereof, $R^1$ is selected from the group consisting of H, and F.

In embodiment of the invention and/or embodiments thereof, $R^1$ is H.

In embodiment of the invention and/or embodiments thereof, $R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_1-C_6)$haloalkoxy, $(C_1-C_6)$alkyl- $S(O)_2NH_2$, and $S-(Halo)_5$.

In embodiment of the invention and/or embodiments thereof, $R^2$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, $(C_1-C_6)$haloalkyl, $(C_2-C_6)$haloalkenyl, $(C_1-C_6)$haloalkoxy, and $S-(Halo)_5$.

In embodiment of the invention and/or embodiments thereof, $R^2$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, and $(C_1-C_6)$haloalkyl.

In embodiment of the invention and/or embodiments thereof, $R^2$ is selected from the group consisting of H, F, Cl, Br, I, CN, $NH_2$, $(C_1-C_6)$alkyl, $(C_1-C_6)$alkoxy, and $(C_1-C_6)$haloalkyl.

In embodiment of the invention and/or embodiments thereof, $R^2$ is selected from the group consisting of H, F, Cl, Br, CN, $NH_2$, $(C_1-C_6)$alkyl, and $(C_1-C_6)$haloalkyl.

In embodiment of the invention and/or embodiments thereof, $R^2$ is selected from the group consisting of H, F, Cl, CN, $(C_1-C_6)$alkyl, and $(C_1-C_6)$haloalkyl.

In embodiment of the invention and/or embodiments thereof, $R^2$ is selected from the group consisting of H, F, Cl, CN, $CH_3$, $CHF_2$ and $CF_3$.

In embodiment of the invention and/or embodiments thereof, $R^2$ is selected from the group consisting of H, F, and Cl, preferably $R^2$ is F or Cl.

In embodiment of the invention and/or embodiments thereof, $R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_1-C_6)$haloalkoxy, $(C_1-C_6)$alkyl- $S(O)_2NH_2$, and $S-(Halo)_5$.

In embodiment of the invention and/or embodiments thereof, $R^3$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, $(C_1-C_6)$haloalkyl, $(C_2-C_6)$haloalkenyl, $(C_1-C_6)$haloalkoxy, and $S-(Halo)_5$.

In embodiment of the invention and/or embodiments thereof, $R^3$ is selected from the group consisting of H, F, Cl, Br, I, CN, $NH_2$, $NO_2$, $(C_1-C_6)$alkyl, $(C_1-C_6)$alkoxy, $(C_1-C_6)$haloalkyl, and $(C_1-C_6)$haloalkoxy.

In embodiment of the invention and/or embodiments thereof, $R^3$ is selected from the group consisting of H, F, Cl, Br, I, CN, $NH_2$, $(C_1-C_6)$alkyl, and $(C_1-C_6)$haloalkyl.

In embodiment of the invention and/or embodiments thereof, $R^3$ is selected from the group consisting of H, F, Cl, Br, I, $(C_1-C_6)$alkyl, and $(C_1-C_6)$haloalkyl.

In embodiment of the invention and/or embodiments thereof, $R^3$ is selected from the group consisting of H, F, Cl, Br, $CH_3$, $CHF_2$ and $CF_3$, preferably $R^3$ is selected from the group consisting of H, F, Cl, Br and $CHF_2$.

In embodiment of the invention and/or embodiments thereof, $R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $(C_1-C_6)$alkyl-$S(O)_2NH_2$, and $S-(Halo)_5$.

In embodiment of the invention and/or embodiments thereof, $R^4$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, $(C_1-C_6)$haloalkyl, $(C_2-C_6)$haloalkenyl, $(C_1-C_6)$haloalkoxy, and $S-(Halo)_5$.

In embodiment of the invention and/or embodiments thereof, $R^4$ is selected from the group consisting of H, F, Cl, Br, I, CN, $NH_2$, $(C_1-C_6)$alkyl, $(C_1-C_6)$alkoxy, $(C_1-C_6)$haloalkyl, and $(C_1-C_6)$haloalkoxy.

In embodiment of the invention and/or embodiments thereof, $R^4$ is selected from the group consisting of H, F, Cl, Br, I, $(C_1-C_6)$alkyl, and $(C_1-C_6)$haloalkyl.

In embodiment of the invention and/or embodiments thereof, $R^4$ is selected from the group consisting of H, F, Cl, Br, $CH_3$, $CHF_2$ and $CF_3$, preferably $R^4$ is selected from the group consisting of H, F, and Cl, more preferably $R^4$ is F or Cl.

In embodiment of the invention and/or embodiments thereof, $R^5$ is selected from the group consisting of H, F, Cl, Br, I, CN, $NH_2$, $NO_2$, $(C_1-C_6)$alkyl, $(C_2-C_6)$alkenyl, $(C_2-C_6)$alkynyl, $(C_1-C_6)$alkoxy, $(C_1-C_6)$haloalkyl, $(C_2-C_6)$haloalkenyl, and $(C_1-C_6)$haloalkoxy.

In embodiment of the invention and/or embodiments thereof, $R^5$ is selected from the group consisting of H, F, Cl, Br, $NH_2$, $(C_1-C_6)$alkyl, $(C_1-C_6)$alkoxy, $(C_1-C_6)$haloalkyl, and $(C_1-C_6)$haloalkoxy.

In embodiment of the invention and/or embodiments thereof, $R^5$ is selected from the group consisting of H, F, Cl, Br, $(C_1-C_6)$alkyl, and $(C_1-C_6)$haloalkyl.

In embodiment of the invention and/or embodiments thereof, $R^5$ is selected from the group consisting of H, F, and Cl.

In embodiment of the invention and/or embodiments thereof, $R^5$ is H.

In embodiment of the invention and/or embodiments thereof, $R^6$ and $R^9$ are each selected from the group consisting of H, $CH_3$ and $CH_2CH_3$.

In embodiment of the invention and/or embodiments thereof, $R^6$ and $R^9$ are each selected from the group consisting of H, and $CH_3$.

In embodiment of the invention and/or embodiments thereof, $R^6$ and $R^9$ are each H.

In embodiment of the invention and/or embodiments thereof, $R^7$ and $R^8$ are each selected from the group consisting of Cl and Br.

In embodiment of the invention and/or embodiments thereof, $R^7$ and $R^8$ are each Cl.

In embodiment of the invention and/or embodiments thereof, $R^{10}$ is selected from the group consisting of H, $(C_1-C_6)$alkyl, $(C_2-C_6)$alkenyl, and $(C_1-C_6)$haloalkyl.

In embodiment of the invention and/or embodiments thereof, $R^{10}$ is selected from the group consisting of H, $(C_1-C_6)$alkyl.

In embodiment of the invention and/or embodiments thereof, $R^{10}$ is selected from the group consisting of H, and $CH_3$.

In embodiment of the invention and/or embodiments thereof, $R^{10}$ is H.

In embodiment of the invention and/or embodiments thereof, $R^{11}$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, $(C_1-C_6)$haloalkyl, and $(C_1-C_6)$haloalkoxy.

In embodiment of the invention and/or embodiments thereof, $R^{11}$ is selected from the group consisting of H, F, Cl, Br, I, $(C_1-C_6)$alkyl, and $(C_1-C_6)$haloalkyl.

In embodiment of the invention and/or embodiments thereof, $R^{11}$ is selected from the group consisting of H, F, Cl, $(C_1-C_6)$alkyl, and $(C_1-C_6)$haloalkyl.

In embodiment of the invention and/or embodiments thereof, $R^{11}$ is selected from the group consisting of H, F, Cl, $CH_3$, and $CF_3$.

In embodiment of the invention and/or embodiments thereof, $R^{11}$ is H.

In embodiment of the invention and/or embodiments thereof, $R^{12}$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, $(C_1-C_6)$haloalkyl, $(C_2-C_6)$haloalkenyl, and $(C_1-C_6)$haloalkoxy.

In embodiment of the invention and/or embodiments thereof, $R^{12}$ is selected from the group consisting of H, F, Cl, Br, I, CN, $NH_2$, $(C_1-C_6)$alkyl, $(C_1-C_6)$alkoxy, $(C_1-C_6)$haloalkyl, and $(C_1-C_6)$haloalkoxy.

In embodiment of the invention and/or embodiments thereof, $R^{12}$ is selected from the group consisting of H, F, Cl, Br, I, $(C_1-C_6)$alkyl, and $(C_1-C_6)$haloalkyl.

In embodiment of the invention and/or embodiments thereof, $R^{12}$ is selected from the group consisting of H, F, Cl, $CH_3$, and $CF_3$.

In embodiment of the invention and/or embodiments thereof, $R^{13}$ is selected from the group consisting of H, F, Cl, Br, I, CN, $NH_2$, $NO_2$, CHO, $(C_1-C_6)$alkyl, $(C_2-C_6)$alkenyl, $(C_1-C_6)$alkoxy, $(C_1-C_6)$haloalkyl, $(C_2-C_6)$haloalkenyl, and $(C_1-C_6)$haloalkoxy.

In embodiment of the invention and/or embodiments thereof, $R^{13}$ is selected from the group consisting of H, F, Cl, Br, I, $NH_2$, $(C_1-C_6)$alkyl, $((C_1-C_6)$alkoxy, $(C_1-C_6)$haloalkyl, and $(C_1-C_6)$haloalkoxy.

In embodiment of the invention and/or embodiments thereof, $R^{13}$ is selected from the group consisting of H, F, Cl, Br, $CH_3$, $OCH_3$, and $CF_3$.

In embodiment of the invention and/or embodiments thereof, $R^{13}$ is selected from the group consisting of H, Cl, F, $CH_3$, and $OCH_3$.

In embodiment of the invention and/or embodiments thereof, $R^{13}$ is Cl or F.

In embodiment of the invention and/or embodiments thereof, $R^{14}$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, $(C_1-C_6)$haloalkyl, $(C_2-C_6)$haloalkenyl, and $(C_1-C_6)$haloalkoxy.

In embodiment of the invention and/or embodiments thereof, $R^{14}$ is selected from the group consisting of H, F, Cl, Br, I, $NH_2$, $(C_1-C_6)$alkyl, and $(C_1-C_6)$haloalkyl.

In embodiment of the invention and/or embodiments thereof, $R^{14}$ is selected from the group consisting of H, F, Cl, $CH_3$ and $CF_3$.

In embodiment of the invention and/or embodiments thereof, $R^{14}$ is selected from the group consisting of H, F, or Cl.

In embodiment of the invention and/or embodiments thereof, $R^{14}$ is H or F preferably H.

In embodiment of the invention and/or embodiments thereof, $R^{15}$ is selected from the group consisting of H, $(C_1-C_6)$alkyl, and $(C_2-C_6)$alkenyl.

In embodiment of the invention and/or embodiments thereof, $R^{15}$ is selected from the group consisting of H, and $(C_1-C_6)$alkyl.

In embodiment of the invention and/or embodiments thereof, $R^{15}$ is selected from the group consisting of H and $CH_3$.

In embodiment of the invention and/or embodiments thereof, $Q^1$ and $Q^2$ are O.

In embodiment of the invention and/or embodiments thereof, $R^{16}$ is selected from the group consisting of $(C_1-C_8)$alkyl, $(C_3-C_8)$cycloalkyl, $(C_1-C_8)$alkyl-O—$(C_1-C_8)$alkyl, $(C_1-C_8)$alkyl$(C_3-C_8)$cycloalkyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, $(C_1-C_8)$alkyl-O—$(C_1-C_8)$haloalkyl, $(C_1-C_8)$alkyl-S—$(C_1-C_8)$haloalkyl, $(C_1-C_8)$alkyl-S(O)—$(C_1-C_8)$haloalkyl, $(C_1-C_8)$alkyl-$S(O)_2$—$(C_1-C_8)$haloalkyl, $(C_1-C_8)$alkyl-$S(O)_2$—$NH_2$, and heterocycle.

In embodiment of the invention and/or embodiments thereof, in $R^{16}$ each alkyl, alkenyl, alkynyl, alkyl-cycloalkyl, $(C_3-C_8)$cycloalkyl, and haloalkyl, may be optionally substituted with one or more substituents selected from the group consisting of F, Cl, Br, I, CN, OH, $NH_2$, $NO_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $C(O)O(C_1-C_8)$alkyl, oxoimidazolidinyl, furanyl, and pyrazolyl.

In embodiment of the invention and/or embodiments thereof, in $R^{16}$ the $(C_3-C_8)$cycloalkyl, may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, $C(=O)O(C_1-C_4)$alkyl, $(C=O)NH(C_1-C_4)$alkyl, $(C=O)NH(C_1-C_4)$haloalkyl, $C(=O)(C_3-C_6)$cyclopropyl, $C(=O)(C_1-C_4)$haloalkyl, $C(=O)(C_1-C_4)$alkyl$(C_1-C_4)$alkoxy, and $(C_1-C_4)$alkyl-morpholinyl.

In embodiment of the invention and/or embodiments thereof, in $R^{16}$ the $(C_3-C_8)$cycloalkyl, may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, $(C=O)NH(C_1-C_4)$alkyl, $(C=O)NH(C_1-C_4)$haloalkyl, $C(=O)(C_3-C_6)$cyclopropyl, $C(=O)(C_1-C_4)$haloalkyl, and $C(=O)(C_1-C_4)$alkyl$(C_1-C_4)$alkoxy.

In embodiment of the invention and/or embodiments thereof, in $R^{16}$ the $(C_3-C_8)$cycloalkyl, may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, $(C=O)NH(C_1-C_4)$alkyl, and $(C=O)NH(C_1-C_4)$haloalkyl.

In embodiment of the invention and/or embodiments thereof, in $R^{16}$ the $(C_3-C_8)$cycloalkyl, may be optionally substituted with one or more substituents selected from the group consisting of H, F, Cl, Br, I, CN, oxo, $(C_1-C_4)$alkyl, $(C_2-C_8)$alkenyl, $(C_2-C_8)$alkynyl, $(C_1-C_4)$haloalkyl, and $(C=O)NH(C_1-C_4)$alkyl.

In embodiment of the invention and/or embodiments thereof, in $R^{16}$ the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, $(C_2-C_8)$alkynyl, $(C_1-C_4)$haloalkyl, and $(C=O)NH(C_1-C_4)$alkyl.

In embodiment of the invention and/or embodiments thereof, in $R^{16}$ the $(C_3-C_8)$cycloalkyl, may be optionally substituted with one or more substituents selected from the group consisting of H, F, Cl, and CN.

In embodiment of the invention and/or embodiments thereof, in $R^{16}$ the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, and $(C_2-C_8)$alkynyl.

In embodiment of the invention and/or embodiments thereof, $R^{16}$ is selected from the group consisting of $(C_1-C_8)$alkyl, $(C_3-C_8)$cycloalkyl, $(C_1-C_8)$alkyl$(C_3-C_8)$cycloalkyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, and $(C_1-C_8)$alkyl-O—$(C_1-C_8)$haloalkyl.

In embodiment of the invention and/or embodiments thereof, $R^{16}$ is selected from the group consisting of $(C_1-C_8)$alkyl, $(C_3-C_8)$cycloalkyl, $(C_2-C_8)$alkenyl, $(C_2-C_8)$alkynyl, $(C_1-C_8)$haloalkyl, and $(C_1-C_8)$alkyl-O—$(C_1-C_8)$haloalkyl.

In embodiment of the invention and/or embodiments thereof, $R^{16}$ is selected from the group consisting of $(C_1-C_8)$alkyl, $(C_3-C_8)$cycloalkyl, $(C_2-C_8)$alkenyl, $(C_2-C_8)$alkynyl, and $(C_1-C_8)$haloalkyl. In embodiment of the invention and/or embodiments thereof, in $R^{16}$ each alkyl, alkenyl, alkynyl, alkyl-cycloalkyl, and haloalkyl, may be optionally substituted with one or more substituents selected from the group consisting of F, Cl, Br, I, CN, OH, $NH_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $C(O)O(C_1-C_8)$alkyl, oxoimidazolidinyl, and furanyl.

In embodiment of the invention and/or embodiments thereof, $R^{16}$ is selected from the group consisting of $(C_1-C_8)$alkyl, $(C_3-C_8)$cycloalkyl, and $(C_1-C_8)$haloalkyl.

In embodiment of the invention and/or embodiments thereof, in $R^{16}$ each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$alkoxy, $C(O)O(C_1-C_8)$alkyl, and oxoimidazolidinyl.

In embodiment of the invention and/or embodiments thereof, in $R^{16}$ each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, and $(C_1-C_8)$alkoxy.

In embodiment of the invention and/or embodiments thereof, in $R^{16}$ each alkyl, $(C_3-C_8)$cycloalkyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$alkoxy, $C(O)O(C_1-C_8)$alkyl, and oxoimidazolidinyl.

In embodiment of the invention and/or embodiments thereof, $R^{16}$ is selected from the group consisting of $CH_2$, $CH_2CH_2$, $CH_2CH_2CH_2$, $CH_2CH_2CH_2CH_2$, $CH_2CH_2CH_2OCH_2CH_2$, $CH_3$, $CH_2CH_3$, $CH_2CH_2CH_3$, $CH_2CH_2CH_2CH_3$, $CH_2CH_2CH_2CH_2CH_3$, $CH_2CH_2CH_2CH_2CH_2CH_3$, $CH_2CH(CH_3)_2$, cyclopropyl, cyclobutyl, $CH_2$cyclopropyl, $CH_2CH_2$cyclopropyl, $CH_2$cyclobutyl, $CH_2$phenyl, $CH_2CH_2$phenyl, $CH_2C{\equiv}CH$, $CH_2C{\equiv}CH$, $CH_2CF_3$, $CH_2CH_2F$, $CH_2CHF_2$, $CH(CH_3)CF_3$, $C(CH_3)_2CF_3$, $CH_2CH_2CF_3$, $CH_2CF_2CF_3$, $CH_2CH_2CH_2Cl$, $CH_2CH_2CH_2CF_3$, $CH_2CH_2CF_2CF_3$, $CH_2CF_2CF_2CF_3$, $CH_2CH_2CH_2CH_2F$, $CH_2CH_2SCH_3$, $CH_2CH_2CH_2SCH_3$, $CH(CH_3)CH_2SCH_2CH_2CF_3$, $CH_2CH_2S(O)CH_3$, $CH(CH_3)CH_2S(O)CH_2CH_2CF_3$, $CH_2CH_2S(O)_2CH_3$, $CH(CH_3)CH_2S(O)_2CH_2CH_2CF_3$, $C(CH_3)_2CH_2S(O)_2CH_3$, Ophenyl, $OCH_2CH{=}CH_2$, $OCH_2$cyclopropyl, $OCH_2$phenyl, $CH_2CH_2OCH_2$cyclopropyl, $CH_2CH_2CH_2OCH_2CF_3$, $CH_2C(=O)NHCH_2CF_3$, or $CH_2CH_2NHC(=O)CH_3$, In embodiment of the invention and/or embodiments thereof, in $R^{16}$ each $CH_2$, $CH_2CH_2$, $CH_2CH_2CH_2$, $CH_2CH_2CH_2CH_2$, cyclopropyl, cyclobutyl, and phenyl, may be optionally substituted with one or more substituents selected from the group consisting of F, Cl, CN, $C(CH_3)_3$, $CF_3$, $OCH_3$, $OCH_2CH_3$, $N(CH_3)_2$, and pyridinyl.

In embodiment of the invention and/or embodiments thereof, $R^{16}$ is selected from the group consisting of $CH_3$, $CH_2CH_3$, $CH_2CH_2CH_3$, $CH_2CH_2CH_2CH_3$, $CH_2CH_2CH_2CH_2CH_3$, $CH_2CH_2CH_2CH_2CH_2CH_3$, $CH_2CH(CH_3)_2$, cyclopropyl, cyclopropyl-CN, $CH_2C{\equiv}CH$, $CH_2C{\equiv}CH$, $CH_2CF_3$, $CH_2CHF_2$, $CH_2CH_2F$, $CH(CH_3)CF_3$, $C(CH_3)_2CF_3$, $CH_2CH_2CF_3$, $CH_2CF_2CF_3$, $CH_2CH_2CH_2Cl$, $CH_2CH_2CH_2CF_3$, $CH_2CH_2CF_2CF_3$, $CH_2CH_2CH_2SCH_3$, $CH_2CF_2CF_2CF_3$, $CH_2CH_2CH_2CH_2F$, $CH_2CH_2SCH_3$, $CH(CH_3)CH_2SCH_2CH_2CF_3$, $CH_2CH_2S(O)CH_3$, $CH(CH_3)CH_2S(O)_2CH_2CH_2CF_3$, $CH(CH_3)CH_2S(O)CH_2CH_2CF_3$, $CH_2CH_2S(O)_2CH_3$, $C(CH_3)_2CH_2S(O)_2CH_3$, and $CH_2CH_2CH_2OCH_2CF_3$.

In embodiment of the invention and/or embodiments thereof, $R^{16}$ is selected from the group consisting of $CH_3$, $CH_2CH_3$, $CH_2CH(CH_3)_2$, cyclopropyl-CN, $CH_2CF_3$, $CH_2CHF_2$, $CH_2CH_2F$, $CH_2CH_2CF_3$, $CH_2CF_2CF_3$, $CH(CH_3)CF_3$, $C(CH_3)_2CF_3$, and $CH_2CH_2CH_2Cl$.

In embodiment of the invention and/or embodiments thereof, $R^{16}$ is selected from the group consisting of $CH_3$, $CH_2CH_3$, $CH_2CH(CH_3)_2$, $CH_2CF_3$, $CH_2CH_2F$, $CH_2CH_2CF_3$, $CH(CH_3)CF_3$, $C(CH_3)_2CF_3$, and $CH_2CH_2CH_2Cl$.

In embodiment of the invention and/or embodiments thereof, the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide. wherein $R^{16}$ each $(C_3-C_8)$cycloalkyl, and heterocycle may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, $C(=O)O(C_1-C_4)$alkyl, $(C=O)NH(C_1-C_4)$alkyl, $(C=O)NH(C_1-C_4)$haloalkyl, $C(=O)(C_3-C_6)$cyclopropyl, $C(=O)(C_1-C_4)$haloalkyl, $C(=O)(C_1-C_4)$alkyl$(C_1-C_4)$alkoxy, and $(C_1-C_4)$alkyl-morpholinyl.

In embodiment of the invention and/or embodiments thereof, the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide.

In embodiment of the invention and/or embodiments thereof, the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide.

In embodiment of the invention and/or embodiments thereof, each heterocycle in $R^{16}$ may be optionally substituted with one or more substituents selected from the group consisting of H, F, Cl, Br, I, CN, oxo, $(C_1-C_4)$alkyl, $(C_2-C_8)$alkenyl, $(C_2-C_8)$alkynyl, $(C_1-C_4)$haloalkyl, $(C=O)NH(C_1-C_4)$alkyl, $(C=O)NH(C_1-C_4)$haloalkyl, and $C(=O)(C_1-C_4)$alkyl$(C_1-C_4)$alkoxy.

In embodiment of the invention and/or embodiments thereof, the heterocycle in $R^{16}$ is selected from the group consisting of azetidinyl, oxetanyl, and tetrahydrofuranyl.

In embodiment of the invention and/or embodiments thereof, each heterocycle in $R^{16}$ may be optionally substituted with one or more substituents selected from the group consisting of H, F, Cl, Br, I, CN, oxo, $(C_1-C_4)$alkyl, $(C_2-C_8)$alkenyl, $(C_2-C_8)$alkynyl, $(C_1-C_4)$haloalkyl, $(C=O)NH(C_1-C_4)$alkyl, $(C=O)NH(C_1-C_4)$haloalkyl, and $C(=O)(C_1-C_4)$alkyl$(C_1-C_4)$alkoxy.

In embodiment of the invention and/or embodiments thereof, the heterocycle in $R^{16}$ is selected from the group consisting of azetidinyl, oxetanyl, and tetrahydrofuranyl, In embodiment of the invention and/or embodiments thereof, each heterocycle in $R^{16}$ may be optionally substituted with one or more substituents selected from the group consisting of H, F, Cl, Br, I, CN, oxo, $(C_1-C_4)$alkyl, $(C_2-C_8)$alkenyl, $(C_2-C_8)$alkynyl, and $(C_1-C_4)$haloalkyl.

In embodiment of the invention and/or embodiments thereof, the heterocycle in $R^{16}$ is selected from the group consisting of oxetanyl, and tetrahydrofuranyl.

In embodiment of the invention and/or embodiments thereof, each heterocycle in $R^{16}$ may be optionally substituted with one or more substituents selected from the group consisting of H, F, CN, oxo, $(C_1-C_4)$alkyl, $(C_2-C_8)$alkenyl, $(C_2-C_8)$alkynyl, and $(C_1-C_4)$haloalkyl.

In embodiment of the invention and/or embodiments thereof, the heterocycle in $R^{16}$ is selected from the group consisting of azetidinyl, morpholinyl, oxetanyl, oxotetrahydrofuranyl pyranyl, tetrahydrothiophenyl, thietanyl, thietanyl-oxide, and thietanyl-dioxide.

In embodiment of the invention and/or embodiments thereof, the $(C_3-C_8)$cycloalkyl in $R^{16}$ selected from the group consisting of cyclopropyl, cyclobutyl, cyclopentyl, cyclohexyl.

In embodiment of the invention and/or embodiments thereof, each heterocycle in $R^{16}$ may be optionally substituted with one or more substituents selected from the group consisting of H, F, CN, C≡CH, CH=CH$_2$, $C(=O)OC(CH_3)_3$, and $C(=O)CF_3$.

In embodiment of the invention and/or embodiments thereof, $R^{16}$ is selected from the group consisting of cyclopropyl, cyclobutyl, azetidinyl, oxetanyl, oxotetrahydrofuranyl.

In embodiment of the invention and/or embodiments thereof, each heterocycle in $R^{16}$ may be optionally substituted with one or more substituents selected from the group consisting of H, F, CN, C≡CH, $C(=O)OC(CH_3)_3$, and $C(=O)CF_3$.

In embodiment of the invention and/or embodiments thereof, $R^{16}$ is selected from the group consisting of cyclopropyl, cyclobutyl, azetidinyl, oxetanyl, oxotetrahydrofuranyl.

In embodiment of the invention and/or embodiments thereof, each heterocycle in $R^{16}$ may be optionally substituted with one or more substituents selected from the group consisting of H, F, and CN.

In embodiment of the invention and/or embodiments thereof, $R^1$ is selected from the group consisting of H F, and Cl;

$R^2$ is selected from the group consisting of H, F, Cl, Br, $CH_3$, and $CF_3$;

$R^3$ is selected from the group consisting of H, F, Cl, $CH_3$, and $CHF_2$, $CF_3$, $OCF_3$;

$R^4$ is selected from the group consisting of H, F, Cl, Br, $CH_3$, and $CF_3$;

$R^5$ is H;

$R^6$ is H;

$R^7$ is selected from the group consisting of Cl and Br;

$R^8$ is selected from the group consisting of Cl and Br;

$R^9$, $R^{10}$, and $R^{11}$ is H;

$R^{12}$ is selected from the group consisting H, F, Cl, Br, $CH_3$;

$R^{13}$ is selected from the group consisting of H, F, Cl, $CH_3$ and $CF_3$;

$R^{14}$ is H or F;

$R^{15}$ is selected from the group consisting of H and $CH_3$;

Q1 and Q2 are O.

In embodiment of the invention and/or embodiments thereof, $R^1$ is H;

$R^2$ is selected from the group consisting of H, F, Cl, and $CH_3$;

$R^3$ is selected from the group consisting of H, F, Cl, $CH_3$, and $CHF_2$;

$R^4$ is selected from the group consisting of H, F, Cl, Br, $CH_3$, $CHF_2$ and $CF_3$;

$R^5$ is H;

$R^6$ is H;

$R^7$ is Cl;

$R^8$ is Cl;

$R^9$, $R^{10}$, and $R^{11}$ is H;

$R^{12}$ is selected from the group consisting H, F, Cl, Br, $CH_3$;

$R^{13}$ is selected from the group consisting of F, Cl, and $CH_3$;

$R^{14}$ is H or F;

$R^{15}$ is selected from the group consisting of H and $CH_3$;

Q1 and Q2 are O.

In embodiment of the invention and/or embodiments thereof, $R^1$ is H;

$R^2$ is selected from the group consisting of H, F, and Cl;

$R^3$ is selected from the group consisting of H, F, and Cl;

$R^4$ is selected from the group consisting of H, F, and Cl;

$R^5$ is H;

$R^6$ is H;

$R^7$ is Cl;

$R^8$ is Cl;

$R^9$, $R^{10}$, and $R^{11}$ is H;

$R^{12}$ is selected from the group consisting H, and F;

$R^{13}$ is selected from the group consisting of F, and Cl;

$R^{14}$ is H;

$R^{15}$ is H;

Q1 and Q2 are O.

In embodiment of the invention and/or embodiments thereof, at least one of the following conditions is met:

a) $R^1$ is selected from the group consisting of H F, and Cl;

b) $R^2$ is selected from the group consisting of H, F, Cl, Br, $CH_3$, and $CHF_2$;

c) $R^3$ is selected from the group consisting of H, F, Cl, $CH_3$, and $CHF_2$, $CF_3$, $OCF_3$;

d) $R^4$ is selected from the group consisting of H, F, Cl, Br, $CH_3$, and $CF_3$;

e) $R^5$ is H;

f) $R^6$ is H;

g) $R^7$ is selected from the group consisting of Cl and Br;

h) $R^8$ is selected from the group consisting of Cl and Br;

i) $R^9$, $R^{10}$, and $R^{11}$ is H;

j) $R^{12}$ is selected from the group consisting H, F, Cl, Br, $CH_3$;

k) $R^{13}$ is selected from the group consisting of H, F, Cl, $CH_3$ and $CF_3$;

l) $R^{14}$ is is selected from the group consisting of H, Cl and F;

m) $R^{15}$ is selected from the group consisting of H and $CH_3$;

n) $Q^1$ and $Q^2$ are O.

In embodiment of the invention and/or embodiments thereof. $R^1$ is selected from the group consisting of H F, and Cl and at least one of the following conditions is met:

a) $R^2$ is selected from the group consisting of H, F, Cl, Br, $CH_3$, and $CHF_2$;

b) $R^3$ is selected from the group consisting of H, F, Cl, $CH_3$, and $CHF_2$, $CF_3$, $OCF_3$;

c) $R^4$ is selected from the group consisting of H, F, Cl, Br, $CH_3$, and $CF_3$;

d) $R^5$ is H;

e) $R^6$ is H;

f) $R^7$ is selected from the group consisting of Cl and Br;

g) $R^8$ is selected from the group consisting of Cl and Br;

h) $R^9$, $R^{10}$, and $R^{11}$ is H;

i) $R^{12}$ is selected from the group consisting H, F, Cl, Br, $CH_3$;

j) $R^{13}$ is selected from the group consisting of H, F, Cl, $CH_3$ and $CF_3$;

k) $R^{14}$ is is selected from the group consisting of H, Cl and F;

I) $R^{15}$ is selected from the group consisting of H and $CH_3$;

m) Q1 and Q2 are O.

In embodiment of the invention and/or embodiments thereof, $R^6$ is H, $R^7$ is selected from the group consisting of Cl and Br, $R^8$ is selected from the group consisting of Cl and Br, $R^9$, $R^{10}$, and $R^{11}$ are H and at least one of the following conditions is met:

a) $R^1$ is selected from the group consisting of H F, and Cl;

b) $R^2$ is selected from the group consisting of H, F, Cl, Br, $CH_3$, and $CHF_2$;

c) $R^3$ is selected from the group consisting of H, F, Cl, $CH_3$, and $CHF_2$, $CF_3$, $OCF_3$;

d) $R^4$ is selected from the group consisting of H, F, Cl, Br, $CH_3$, and $CF_3$;

e) $R^5$ is H;

f) $R^{12}$ is selected from the group consisting H, F, Cl, Br, $CH_3$;

g) $R^{13}$ is selected from the group consisting of H, F, Cl, $CH_3$ and $CF_3$;

h) $R^{14}$ is is selected from the group consisting of H, Cl and F;

i) $R^{15}$ is selected from the group consisting of H and $CH_3$;

j) Q1 and Q2 are O.

In embodiment of the invention and/or embodiments thereof, at least one of the following conditions is met:

a) $R^1$ is selected from the group consisting of H F, and Cl;

b) $R^2$ is selected from the group consisting of H, F, and Cl;

c) $R^3$ is selected from the group consisting of H, F, and Cl;

d) $R^4$ is selected from the group consisting of H, F, and Cl;

e) $R^5$ is H;

f) $R^6$ is H;

g) $R^7$ is selected from the group consisting of Cl;

h) $R^8$ is selected from the group consisting of Cl;

i) $R^9$, $R^{10}$, and $R^{11}$ is H;

j) $R^{12}$ is selected from the group consisting H, F, and Cl;

k) $R^{13}$ is selected from the group consisting of F, and Cl;

l) $R^{14}$ is is selected from the group consisting of H, Cl and F;

m) $R^{15}$ is selected from the group consisting of H;

n) Q1 and Q2 are O.

In embodiment of the invention and/or embodiments thereof, $R^1$ is selected from the group consisting of H F, and Cl and at least one of the following conditions is met:

a) $R^2$ is selected from the group consisting of H, F, and Cl;

b) $R^3$ is selected from the group consisting of H, F, and Cl;

c) $R^4$ is selected from the group consisting of H, F, and Cl;

d) $R^5$ is H;

e) $R^6$ is H;

f) $R^7$ is selected from the group consisting of Cl;

g) $R^8$ is selected from the group consisting of Cl;

h) $R^9$, $R^{10}$, and $R^{11}$ is H;

i) $R^{12}$ is selected from the group consisting H, F, and Cl;

j) $R^{13}$ is selected from the group consisting of F, and Cl;

k) $R^{14}$ is is selected from the group consisting of H, Cl and F;

l) $R^{15}$ is selected from the group consisting of H;

m) Q1 and Q2 are O.

In embodiment of the invention and/or embodiments thereof, $R^6$ is H, $R^7$ is selected from the group consisting of Cl, $R^8$ is selected from the group consisting of Cl, $R^9$, $R^{10}$, and $R^{11}$ are H and at least one of the following conditions is met:

a) $R^1$ is selected from the group consisting of H F, and Cl;

b) $R^2$ is selected from the group consisting of H, F, and Cl;

c) $R^3$ is selected from the group consisting of H, F, and Cl;

d) $R^4$ is selected from the group consisting of H, F, and Cl;

e) $R^5$ is H;

f) $R^{12}$ is selected from the group consisting H, F, and Cl;

g) $R^{13}$ is selected from the group consisting of F, and Cl;

h) $R^{14}$ is is selected from the group consisting of H, Cl and F;

i) $R^{15}$ is selected from the group consisting of H;

j) Q1 and Q2 are O.

In an embodiment of the invention and/or embodiments thereof, the invention is directed to a compound of formula (II)

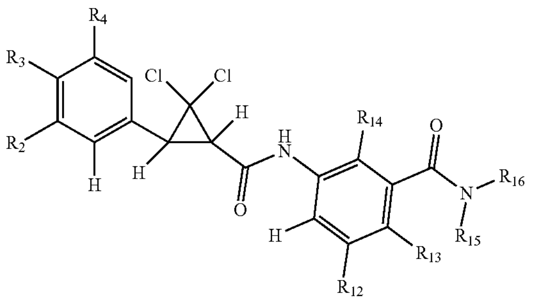

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^5$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^6$ is selected from the group consisting of H and $(C_1-C_6)$alkyl;

$R^7$ is selected from the group consisting of H, F, Cl, Br, and I;

$R^8$ is selected from the group consisting of F, Cl, Br, and I;

$R^9$ is selected from the group consisting of H and $(C_1-C_6)$alkyl;

$R^{10}$ is selected from the group consisting of H, $(C_1-C_6)$alkyl, $(C_2-C_6)$alkenyl, $(C_1-C_6)$haloalkyl, $(C_1-C_6)$alkyl$(C_1-C_6)$alkoxy, $C(=O)(C_1-C_6)$alkyl, and $(C_1-C_6)$alkoxy$C(=O)(C_1-C_6)$alkyl;

$R^{12}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^{13}$ is selected from the group consisting of H, F, Cl, Br, I, CN, $NH_2$, $NO_2$, CHO, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and triazolyl;

$R^{14}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^{15}$ is selected from the group consisting of H, $(C_1-C_6)$alkyl, and $(C_2-C_6)$alkenyl;

$R^{16}$ is selected from the group consisting of $(C_1-C_8)$alkyl, $(C_3-C_8)$cycloalkyl, $(C_1-C_8)$alkyl-O—$(C_1-C_8)$alkyl, $(C_1-C_8)$alkyl$(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, O- phenyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$cycloalkyl, $(C_1-C_8)$alkyl-O—$(C_1-C_8)$haloalkyl, $(C_1-C_8)$alkyl-C(=O)NH—$(C_1-C_8)$haloalkyl, $(C_1-C_8)$alkyl-NHC(O)—$(C_1-C_8)$alkyl, $(C_1-C_8)$alkyl-S—$(C_1-C_8)$haloalkyl, $(C_1-C_8)$alkyl-S(O)—$(C_1-C_8)$haloalkyl, $(C_1-C_8)$alkyl-$S(O)_2$—$(C_1-C_8)$haloalkyl, $(C_1-C_8)$alkyl-$S(O)_2$—$NH_2$, and a heterocycle, wherein each alkyl, alkenyl, alkynyl, alkyl-cycloalkyl, haloalkyl, and phenyl, may be optionally substituted with one or more substituents selected from the group consisting of F, Cl, Br, I, CN, OH, $NH_2$, $NO_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $N((C_1-C_8)alkyl)_2$, $C(O)O(C_1-C_8)$alkyl, benzothioenyl, oxoimidazolidinyl, furanyl, pyrazolyl, pyridinyl, thiazolyl, and triazolyl, and wherein the heterocycle is selected from the group consisting of, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, and wherein each ($C_3$-$C_8$)cycloalkyl and heterocycle may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, C(=O)O($C_1$-$C_4$)alkyl, (C=O)NH($C_1$-$C_4$)alkyl, (C=O)NH($C_1$-$C_4$)haloalkyl, C(=O)($C_3$-$C_6$)cyclopropyl, C(=O)($C_1$-$C_4$)haloalkyl, C(=O)($C_1$-$C_4$)alkyl($C_1$-$C_4$)alkoxy, and ($C_1$-$C_4$)alkyl-morpholinyl;

$R^{15}$ and $R^{16}$ together can optionally form a 2- to 5-membered saturated or unsaturated, hydrocarbyl link, which may contain one or more heteroatoms selected from the group consisting of nitrogen, sulfur, and oxygen, wherein said hydrocarbyl link may be optionally substituted with one or more substituents selected from the group consisting of F, Cl, Br, I, CN, $NH_2$, and $NO_2$;

$Q^1$ and $Q^2$ are each independently selected from the group consisting of O and S.

In an embodiment of the invention and/or embodiments thereof, the invention is directed to a compound of formula (II)

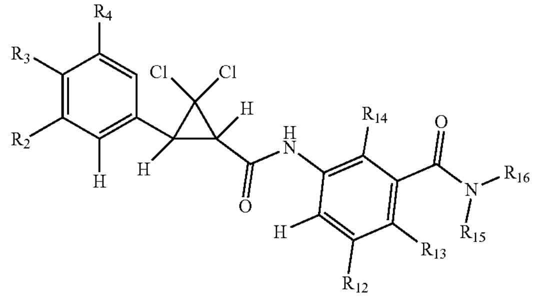

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_1$-$C_6$)haloalkoxy, ($C_1$-$C_6$)alkyl-$S(O)_2NH_2$, and S-$(Halo)_5$;

$R^3$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_1$-$C_6$)haloalkoxy, ($C_1$-$C_6$)alkyl-$S(O)_2NH_2$, and S-$(Halo)_5$;

$R^4$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, ($C_1$-$C_6$)alkyl-$S(O)_2NH_2$, and S-$(Halo)_5$;

$R^5$ is selected from the group consisting of H, F, Cl, Br, I, CN, $NH_2$, $NO_2$, ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_2$-$C_6$)haloalkenyl, and ($C_1$-$C_6$)haloalkoxy;

$R^6$ and $R^9$ are each selected from the group consisting of H, $CH_3$ and $CH_2CH_3$;

$R^7$ and $R^8$ are each selected from the group consisting of Cl and Br;

$R^{10}$ is selected from the group consisting of H, ($C_1$-$C_6$)alkyl, ($C_2$-$C_6$)alkenyl, and ($C_1$-$C_6$)haloalkyl;

$R^{12}$ is selected from the group consisting of H, F, Cl, Br, I, CN, $NH_2$, $NO_2$, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{13}$ is selected from the group consisting of H, F, Cl, Br, I, CN, $NH_2$, $NO_2$, CHO, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{14}$ is selected from the group consisting of H, F, Cl, Br, I, CN, $NH_2$, $NO_2$, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{15}$ is selected from the group consisting of H, ($C_1$-$C_6$)alkyl, and ($C_2$-$C_6$)alkenyl;

$R^{16}$ is selected from the group consisting of ($C_1$-$C_8$)alkyl, ($C_3$-$C_8$)cycloalkyl, ($C_1$-$C_8$)alkyl-O—($C_1$-$C_8$)alkyl, ($C_1$-$C_8$)alkyl($C_3$-$C_8$)cycloalkyl, ($C_2$-$C_8$)alkenyl, ($C_2$-$C_8$)alkynyl, ($C_1$-$C_8$)haloalkyl, ($C_1$-$C_8$)alkyl- S—($C_1$-$C_8$)alkyl, ($C_1$-$C_8$)alkyl-S(O)—($C_1$-$C_8$)alkyl, ($C_1$-$C_8$)alkyl-$S(O)_2$—($C_1$-$C_8$)alkyl, ($C_1$-$C_8$)alkyl-O—($C_1$- $C_8$)haloalkyl, ($C_1$-$C_8$)alkyl-S—($C_1$-$C_8$)haloalkyl, ($C_1$-$C_8$)alkyl-S(O)—($C_1$-$C_8$)haloalkyl, ($C_1$-$C_8$)alkyl-$S(O)_2$—($C_1$-$C_8$)haloalkyl, ($C_1$-$C_8$)alkyl-$S(O)_2$—$NH_2$, and heterocycle, wherein each alkyl, alkenyl, alkynyl, alkyl-cycloalkyl, and haloalkyl in $R^{16}$, may be optionally substituted with one or more substituents selected from the group consisting of F, Cl, Br, I, CN, OH, $NH_2$, $NO_2$, ($C_1$-$C_8$)alkyl, ($C_2$-$C_8$)alkenyl, ($C_2$-$C_8$)alkynyl, ($C_1$-$C_8$)alkoxy, ($C_1$-$C_8$)haloalkyl, C(O)O($C_1$-$C_8$)alkyl, oxoimidazolidinyl, furanyl, and pyrazolyl, wherein each ($C_3$-$C_8$)cycloalkyl in $R^{16}$, may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, C(=O)O($C_1$-$C_4$)alkyl, (C=O)NH($C_1$-$C_4$)alkyl, (C=O)NH($C_1$-$C_4$)haloalkyl, C(=O)($C_3$-$C_6$)cyclopropyl, C(=O)($C_1$-$C_4$)haloalkyl, C(=O)($C_1$-$C_4$)alkyl($C_1$-$C_4$)alkoxy, and ($C_1$-$C_4$)alkyl-morpholinyl, wherein the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide, wherein, each heterocycle in $R^{16}$ may be optionally substituted with one or more substituents selected from the group consisting of H, F, Cl, Br, I, CN, oxo, ($C_1$-$C_4$)alkyl, ($C_2$-$C_8$)alkenyl, ($C_2$-$C_8$)alkynyl, ($C_1$-$C_4$)haloalkyl, (C=O)NH($C_1$-$C_4$)alkyl, (C=O)NH($C_1$-$C_4$)haloalkyl, and C(=O)($C_1$-$C_4$)alkyl($C_1$-$C_4$)alkoxy;

$Q^1$ and $Q^2$ are each independently selected from the group consisting of O and S.

In an embodiment of the invention and/or embodiments thereof, the invention is directed to a compound of formula (II)

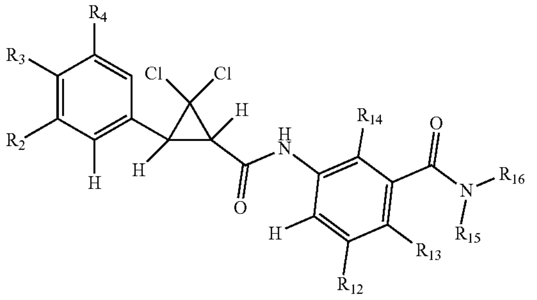

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, and $(C_1-C_6)$haloalkyl;

$R^3$ is selected from the group consisting of H, F, Cl, Br, I, CN, $NH_2$, $NO_2$, $(C_1-C_6)$alkyl, $(C_1-C_6)$alkoxy, $(C_1-C_6)$haloalkyl, and $(C_1-C_6)$haloalkoxy;

$R^4$ is selected from the group consisting of H, F, Cl, Br, I, CN, $NH_2$, $(C_1-C_6)$alkyl, $(C_1-C_6)$alkoxy, $(C_1-C_6)$ haloalkyl, and $(C_1-C_6)$haloalkoxy;

$R^5$ is selected from the group consisting of H, F, Cl, Br, $NH_2$, $(C_1-C_6)$alkyl, $(C_1-C_6)$alkoxy, $(C_1-C_6)$haloalkyl, and $(C_1-C_6)$haloalkoxy;

$R^6$ and $R^9$ are each selected from the group consisting of H, and $CH_3$;

$R^7$ and $R^8$ are each selected from the group consisting of Cl and Br;

$R^{10}$ is selected from the group consisting of H, and $CH_3$; preferably $R^{10}$ is H;

$R^{12}$ is selected from the group consisting of H, F, Cl, Br, I, $(C_1-C_6)$alkyl, and $(C_1-C_6)$haloalkyl;

$R^{13}$ is selected from the group consisting of H, F, Cl, Br, $CH_3$, $OCH_3$, and $CF_3$;

$R^{14}$ is selected from the group consisting of H, F, Cl, Br, I, $NH_2$, $(C_1-C_6)$alkyl, and $(C_1-C_6)$haloalkyl;

$R^{15}$ is selected from the group consisting of H, and $(C_1-C_6)$alkyl;

$R^{16}$ is selected from the group consisting of $(C_1-C_8)$ alkyl, $(C_3-C_8)$cycloalkyl, $(C_1-C_8)$alkyl$(C_3-C_8)$cycloalkyl, $(C_2-C_8)$alkenyl, $(C_2-C_8)$alkynyl, $(C_1-C_8)$ haloalkyl, $(C_1-C_8)$alkyl-S—$(C_1-C_8)$alkyl, $(C_1-C_8)$ alkyl-S(O)—$(C_1-C_8)$alkyl, $(C_1-C_8)$alkyl-$S(O)_2$—$(C_1-C_8)$alkyl, and $(C_1-C_8)$alkyl-O—$(C_1-C_8)$ haloalkyl, wherein each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$alkoxy, C(O)O$(C_1-C_8)$alkyl, and oxoimidazolidinyl, wherein in $R^{16}$ the $(C_3-C_8)$cycloalkyl, may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, (C═O)NH$(C_1-C_4)$alkyl, and (C═O)NH$(C_1-C_4)$haloalkyl;

$Q^1$ and $Q^2$ are O.

In an embodiment of the invention and/or embodiments thereof, the invention is directed to a compound of formula (II)

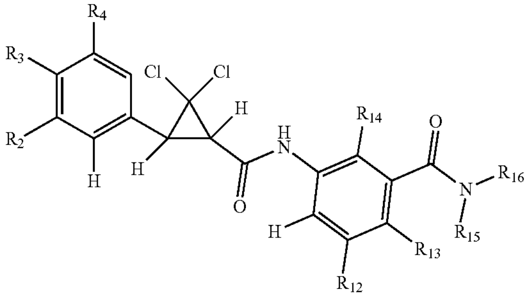

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $(C_1-C_6)$alkyl, $(C_1-C_6)$alkoxy, and $(C_1-C_6)$haloalkyl;

$R^3$ is selected from the group consisting of H, F, Cl, Br, I, CN, $NH_2$, $(C_1-C_6)$alkyl, and $(C_1-C_6)$haloalkyl;

$R^4$ is selected from the group consisting of H, F, Cl, Br, I, $(C_1-C_6)$alkyl, and $(C_1-C_6)$haloalkyl;

$R^5$ is selected from the group consisting of H, F, Cl, Br, $(C_1-C_6)$alkyl, and $(C_1-C_6)$haloalkyl;

$R^6$ and $R^9$ are each H;

$R^7$ and $R^8$ are each Cl;

$R^{10}$ is H;

$R^{12}$ is selected from the group consisting of H, F, Cl, $CH_3$, and $CF_3$;

$R^{13}$ is selected from the group consisting of H, Cl, F, $CH_3$, and $OCH_3$;

$R^{14}$ is selected from the group consisting of H, F, or Cl;

$R^{15}$ is selected from the group consisting of H and $CH_3$;

$R^{16}$ is selected from the group consisting of $(C_1-C_8)$ alkyl, $(C_3-C_8)$cycloalkyl, $(C_2-C_8)$alkenyl, $(C_2-C_8)$ alkynyl, $(C_1-C_8)$haloalkyl, and $(C_1-C_8)$alkyl-O—$(C_1-C_8)$haloalkyl, wherein each alkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$ alkoxy, C(O)O$(C_1-C_8)$alkyl, and oxoimidazolidinyl, wherein the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, $(C_2-C_8)$alkynyl, $(C_1-C_4)$haloalkyl, and (C═O)NH$(C_1-C_4)$alkyl;

$Q^1$ and $Q^2$ are O.

In an embodiment of the invention and/or embodiments thereof, the invention is directed to a compound of formula (III)

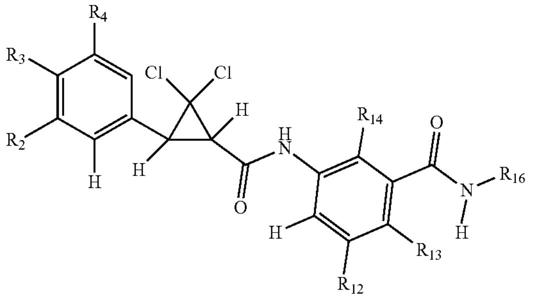

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^5$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^6$ is selected from the group consisting of H and $(C_1-C_6)$alkyl;

$R^7$ is selected from the group consisting of H, F, Cl, Br, and I;

$R^8$ is selected from the group consisting of F, Cl, Br, and I;

$R^9$ is selected from the group consisting of H and $(C_1-C_6)$alkyl;

$R^{10}$ is selected from the group consisting of H, $(C_1-C_6)$alkyl, $(C_2-C_6)$alkenyl, $(C_1-C_6)$haloalkyl, $(C_1-C_6)$alkyl$(C_1-C_6)$alkoxy, $C(=O)(C_1-C_6)$alkyl, and $(C_1-C_6)$alkoxy$C(=O)(C_1-C_6)$alkyl;

$R^{12}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^{13}$ is selected from the group consisting of H, F, Cl, Br, I, CN, $NH_2$, $NO_2$, CHO, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and triazolyl;

$R^{14}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^{16}$ is selected from the group consisting of $(C_1-C_8)$alkyl, $(C_3-C_8)$cycloalkyl, $(C_1-C_8)$alkyl-O—$(C_1-C_8)$alkyl, $(C_1-C_8)$alkyl$(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, O- phenyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$cycloalkyl, $(C_1-C_8)$alkyl-O—$(C_1-C_8)$haloalkyl, $(C_1-C_8)$alkyl-C(=O)NH—$(C_1-C_8)$haloalkyl, $(C_1-C_8)$alkyl-NHC(O)—$(C_1-C_8)$alkyl, $(C_1-C_8)$alkyl-S—$(C_1-C_8)$haloalkyl, $(C_1-C_8)$alkyl-S(O)—$(C_1-C_8)$haloalkyl, $(C_1-C_8)$alkyl-$S(O)_2$—$(C_1-C_8)$haloalkyl, $(C_1-C_8)$alkyl-$S(O)_2$—$NH_2$, and a heterocycle, wherein each alkyl, alkenyl, alkynyl, alkyl-cycloalkyl, haloalkyl, and phenyl, may be optionally substituted with one or more substituents selected from the group consisting of F, Cl, Br, I, CN, OH, $NH_2$, $NO_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $N((C_1-C_8)alkyl)_2$, $C(O)O(C_1-C_8)$alkyl, benzothioenyl, oxoimidazolidinyl, furanyl, pyrazolyl, pyridinyl, thiazolyl, and triazolyl, and wherein the heterocycle is selected from the group consisting of, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, and wherein each ($C_3$-$C_8$)cycloalkyl and heterocycle may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, C(=O)O($C_1$-$C_4$)alkyl, (C=O)NH($C_1$-$C_4$)alkyl, (C=O)NH($C_1$-$C_4$)haloalkyl, C(=O)($C_3$-$C_6$)cyclopropyl, C(=O)($C_1$-$C_4$) haloalkyl, C(=O)($C_1$-$C_4$)alkyl($C_1$-$C_4$)alkoxy, and ($C_1$-$C_4$)alkyl-morpholinyl;

$Q^1$ and $Q^2$ are each independently selected from the group consisting of O and S.

In an embodiment of the invention and/or embodiments thereof, the invention is directed to a compound of formula (III)

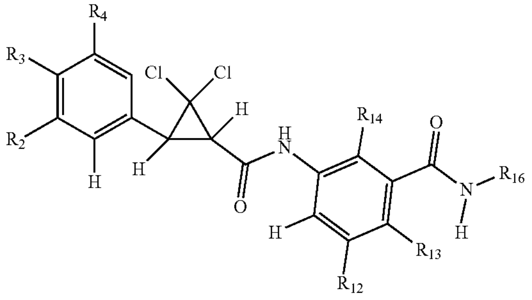

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_1$-$C_6$)haloalkoxy, ($C_1$-$C_6$)alkyl-$S(O)_2NH_2$, and S-$(Halo)_5$;

$R^3$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_1$-$C_6$)haloalkoxy, ($C_1$-$C_6$)alkyl-$S(O)_2NH_2$, and S-$(Halo)_5$;

$R^4$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, ($C_1$-$C_6$)alkyl-$S(O)_2NH_2$, and S-$(Halo)_5$;

$R^5$ is selected from the group consisting of H, F, Cl, Br, I, CN, $NH_2$, $NO_2$, ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_2$-$C_6$)haloalkenyl, and ($C_1$-$C_6$)haloalkoxy;

$R^6$ and $R^9$ are each selected from the group consisting of H, $CH_3$ and $CH_2CH_3$;

$R^7$ and $R^8$ are each selected from the group consisting of Cl and Br;

$R^{10}$ is selected from the group consisting of H, ($C_1$-$C_6$)alkyl, ($C_2$-$C_6$)alkenyl, and ($C_1$-$C_6$)haloalkyl;

$R^{12}$ is selected from the group consisting of H, F, Cl, Br, I, CN, $NH_2$, $NO_2$, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{13}$ is selected from the group consisting of H, F, Cl, Br, I, CN, $NH_2$, $NO_2$, CHO, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{14}$ is selected from the group consisting of H, F, Cl, Br, I, CN, $NH_2$, $NO_2$, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{16}$ is selected from the group consisting of ($C_1$-$C_8$) alkyl, ($C_3$-$C_8$)cycloalkyl, ($C_1$-$C_8$)alkyl-O—($C_1$-$C_8$) alkyl, ($C_1$-$C_8$)alkyl($C_3$-$C_8$)cycloalkyl, ($C_2$-$C_8$)alkenyl, ($C_2$-$C_8$)alkynyl, ($C_1$-$C_8$)haloalkyl, ($C_1$-$C_8$) alkyl- S—($C_1$-$C_8$)alkyl, ($C_1$-$C_8$)alkyl-S(O)—($C_1$-$C_8$)alkyl, ($C_1$-$C_8$)alkyl-$S(O)_2$—($C_1$-$C_8$)alkyl, ($C_1$-$C_8$)alkyl-O—($C_1$- $C_8$)haloalkyl, ($C_1$-$C_8$)alkyl-S—($C_1$-$C_8$)haloalkyl, ($C_1$-$C_8$)alkyl-S(O)—($C_1$-$C_8$) haloalkyl, ($C_1$-$C_8$)alkyl-$S(O)_2$—($C_1$-$C_8$)haloalkyl, ($C_1$-$C_8$)alkyl-$S(O)_2$—$NH_2$, and heterocycle, wherein each alkyl, alkenyl, alkynyl, alkyl-cycloalkyl, and haloalkyl in $R^{16}$, may be optionally substituted with one or more substituents selected from the group consisting of F, Cl, Br, I, CN, OH, $NH_2$, $NO_2$, ($C_1$-$C_8$) alkyl, ($C_2$-$C_8$)alkenyl, ($C_2$-$C_8$)alkynyl, ($C_1$-$C_8$)alkoxy, ($C_1$-$C_8$)haloalkyl, C(O)O($C_1$-$C_8$)alkyl, oxoimidazolidinyl, furanyl, and pyrazolyl, wherein each ($C_3$-$C_8$)cycloalkyl in $R^{16}$, may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, C(=O)O($C_1$-$C_4$)alkyl, (C=O)NH ($C_1$-$C_4$)alkyl, (C=O)NH($C_1$-$C_4$)haloalkyl, C(=O) ($C_3$-$C_6$)cyclopropyl, C(=O)($C_1$-$C_4$)haloalkyl, C(=O) ($C_1$-$C_4$)alkyl($C_1$-$C_4$)alkoxy, and ($C_1$-$C_4$)alkyl-morpholinyl, wherein the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide, wherein, each heterocycle in $R^{16}$ may be optionally substituted with one or more substituents selected from the group consisting of H, F, Cl, Br, I, CN, oxo, ($C_1$-$C_4$) alkyl, ($C_2$-$C_8$)alkenyl, ($C_2$-$C_8$)alkynyl, ($C_1$-$C_4$)haloalkyl, (C=O)NH($C_1$-$C_4$)alkyl, (C=O)NH($C_1$-$C_4$)haloalkyl, and C(=O)($C_1$-$C_4$)alkyl($C_1$-$C_4$)alkoxy;

$Q^1$ and $Q^2$ are each independently selected from the group consisting of O and S.

In an embodiment of the invention and/or embodiments thereof, the invention is directed to a compound of formula (III)

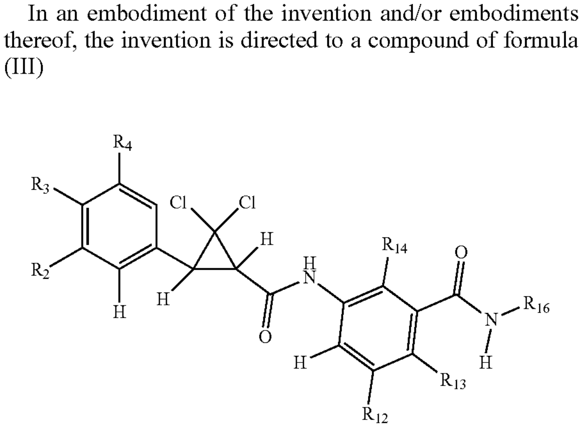

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1\text{-}C_6)$alkyl, $(C_2\text{-}C_6)$alkenyl, $(C_1\text{-}C_6)$alkoxy, and $(C_1\text{-}C_6)$haloalkyl;

$R^3$ is selected from the group consisting of H, F, Cl, Br, I, CN, $NH_2$, $NO_2$, $(C_1\text{-}C_6)$alkyl, $(C_1\text{-}C_6)$alkoxy, $(C_1\text{-}C_6)$haloalkyl, and $(C_1\text{-}C_6)$haloalkoxy;

$R^4$ is selected from the group consisting of H, F, Cl, Br, I, CN, $NH_2$, $(C_1\text{-}C_6)$alkyl, $(C_1\text{-}C_6)$alkoxy, $(C_1\text{-}C_6)$ haloalkyl, and $(C_1\text{-}C_6)$haloalkoxy;

$R^5$ is selected from the group consisting of H, F, Cl, Br, $NH_2$, $(C_1\text{-}C_6)$alkyl, $(C_1\text{-}C_6)$alkoxy, $(C_1\text{-}C_6)$haloalkyl, and $(C_1\text{-}C_6)$haloalkoxy;

$R^6$ and $R^9$ are each selected from the group consisting of H, and $CH_3$;

$R^7$ and $R^8$ are each selected from the group consisting of Cl and Br;

$R^{10}$ is selected from the group consisting of H, and $CH_3$; preferably $R^{10}$ is H;

$R^{12}$ is selected from the group consisting of H, F, Cl, Br, I, $(C_1\text{-}C_6)$alkyl, and $(C_1\text{-}C_6)$haloalkyl;

$R^{13}$ is selected from the group consisting of H, F, Cl, Br, $CH_3$, $OCH_3$, and $CF_3$;

$R^{14}$ is selected from the group consisting of H, F, Cl, Br, I, $NH_2$, $(C_1\text{-}C_6)$alkyl, and $(C_1\text{-}C_6)$haloalkyl;

$R^{16}$ is selected from the group consisting of $(C_1\text{-}C_8)$ alkyl, $(C_3\text{-}C_8)$cycloalkyl, $(C_1\text{-}C_8)$alkyl$(C_3\text{-}C_8)$cycloalkyl, $(C_2\text{-}C_8)$alkenyl, $(C_2\text{-}C_8)$alkynyl, $(C_1\text{-}C_8)$ haloalkyl, $(C_1\text{-}C_8)$alkyl-S—$(C_1\text{-}C_8)$alkyl, $(C_1\text{-}C_8)$ alkyl-S(O)—$(C_1\text{-}C_8)$alkyl, $(C_1\text{-}C_8)$alkyl-$S(O)_2$—$(C_1\text{-}C_8)$alkyl, and $(C_1\text{-}C_8)$alkyl-O—$(C_1\text{-}C_8)$ haloalkyl, wherein each alkyl, cycloalkyl, alkenyl, alkynyl, and haloalkyl, may be optionally substituted with one or more substituents selected from the group consisting of F, Cl, Br, $(C_1\text{-}C_8)$alkyl, $(C_2\text{-}C_8)$alkenyl, $(C_2\text{-}C_8)$alkynyl, $(C_1\text{-}C_8)$alkoxy, $C(O)O(C_1\text{-}C_8)$alkyl, and oxoimidazolidinyl, wherein in $R^{16}$ the $(C_3\text{-}C_8)$cycloalkyl, may be optionally substituted with one or more substituents selected from the group consisting of H, F, Cl, Br, I, CN, $NH_2$, $NO_2$, oxo, $(C_1\text{-}C_4)$alkyl, $(C_2\text{-}C_8)$alkenyl, $(C_2\text{-}C_8)$alkynyl, $(C_1\text{-}C_4)$haloalkyl, $(C{=}O)NH(C_1\text{-}C_4)$alkyl, and $(C{=}O)NH(C_1\text{-}C_4)$haloalkyl;

$Q^1$ and $Q^2$ are O.

In an embodiment of the invention and/or embodiments thereof, the invention is directed to a compound of formula (III)

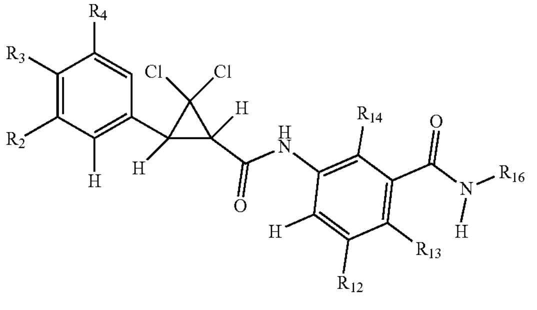

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $(C_1\text{-}C_6)$alkyl, $(C_1\text{-}C_6)$alkoxy, and $(C_1\text{-}C_6)$haloalkyl;

$R^3$ is selected from the group consisting of H, F, Cl, Br, I, CN, $NH_2$, $(C_1\text{-}C_6)$alkyl, and $(C_1\text{-}C_6)$haloalkyl;

$R^4$ is selected from the group consisting of H, F, Cl, Br, I, $(C_1\text{-}C_6)$alkyl, and $(C_1\text{-}C_6)$haloalkyl;

$R^5$ is selected from the group consisting of H, F, Cl, Br, $(C_1\text{-}C_6)$alkyl, and $(C_1\text{-}C_6)$haloalkyl;

$R^6$ and $R^9$ are each H;

$R^7$ and $R^8$ are each Cl;

$R^{10}$ is H;

$R^{12}$ is selected from the group consisting of H, F, Cl, $CH_3$, and $CF_3$;

$R^{13}$ is selected from the group consisting of H, Cl, F, $CH_3$, and $OCH_3$;

$R^{14}$ is selected from the group consisting of H, F, or Cl;

$R^{16}$ is selected from the group consisting of $(C_1\text{-}C_8)$ alkyl, $(C_3\text{-}C_8)$cycloalkyl, $(C_2\text{-}C_8)$alkenyl, $(C_2\text{-}C_8)$ alkynyl, $(C_1\text{-}C_8)$haloalkyl, and $(C_1\text{-}C_8)$alkyl-O—$(C_1\text{-}C_8)$haloalkyl, wherein each alkyl, alkenyl, alkynyl, and haloalkyl, may be optionally substituted with one or more substituents selected from the group consisting of F, Cl, Br, $(C_1\text{-}C_8)$alkyl, $(C_2\text{-}C_8)$alkenyl, $(C_2\text{-}C_8)$alkynyl, $(C_1\text{-}C_8)$ alkoxy, $C(O)O(C_1\text{-}C_8)$alkyl, and oxoimidazolidinyl, wherein the $(C_3\text{-}C_8)$cycloalkyl, may be optionally substituted with one or more substituents selected from the group consisting of H, F, Cl, CN, oxo, $(C_1\text{-}C_4)$alkyl, $(C_2\text{-}C_8)$alkenyl, $(C_2\text{-}C_8)$alkynyl, $(C_1\text{-}C_4)$haloalkyl, and $(C{=}O)NH(C_1\text{-}C_4)$alkyl;

$Q^1$ and $Q^2$ are O.

In an embodiment of the invention and/or embodiments thereof, the invention is directed to a compound of formula (III)

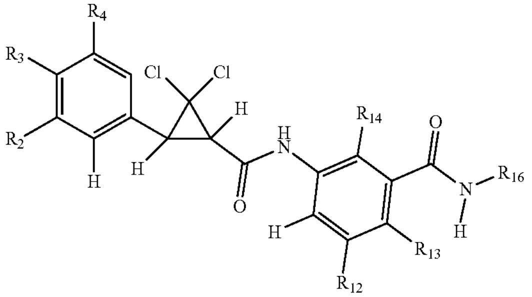

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, CN, $CH_3$, $CHF_2$ and $CF_3$, preferably $R^2$ is selected from the group consisting of H, F, and Cl, preferably $R^2$ is F or Cl;

$R^3$ is selected from the group consisting of H, F, Cl, Br, $CH_3$, $CHF_2$ and $CF_3$, preferably $R^3$ is selected from the group consisting of H, F, Cl, Br and $CHF_2$;

$R^4$ is selected from the group consisting of H, F, Cl, Br, $CH_3$, $CHF_2$ and $CF_3$, preferably $R^4$ is selected from the group consisting of H, F, and Cl, more preferably $R^4$ is F or Cl;

$R^5$ is selected from the group consisting of H, F, and Cl, preferably $R^5$ is H;

$R^6$ and $R^9$ are each H;

$R^7$ and $R^8$ are each Cl;

$R^{10}$ is H;

$R^{12}$ is selected from the group consisting of H, F, Cl, $CH_3$, and $CF_3$;

$R^{13}$ is Cl or F;

$R^{14}$ is H or F preferably H;

$R^{16}$ is selected from the group consisting of $(C_1-C_8)$alkyl, $(C_3-C_8)$cycloalkyl, $(C_2-C_8)$alkenyl, $(C_2-C_8)$alkynyl, and $(C_1-C_8)$haloalkyl, wherein each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, and $(C_1-C_8)$alkoxy, wherein the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, and $(C_2-C_8)$alkynyl;

$Q^1$ and $Q^2$ are O.

In an embodiment of the invention and/or embodiments thereof, the invention is directed to a compound of formula (IV)

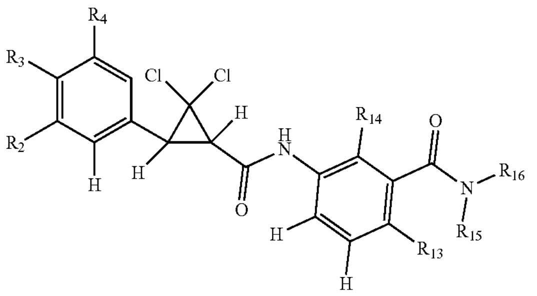

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl- $S(O)_2NH_2$, $(C_1-C_6)$haloalkyl-$S(O)_2NH_2$, and S-$(Halo)_5$;

$R^5$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^6$ is selected from the group consisting of H and $(C_1-C_6)$alkyl;

$R^7$ is selected from the group consisting of H, F, Cl, Br, and I;

$R^8$ is selected from the group consisting of F, Cl, Br, and I;

$R^9$ is selected from the group consisting of H and $(C_1-C_6)$alkyl;

$R^{10}$ is selected from the group consisting of H, $(C_1-C_6)$alkyl, $(C_2-C_6)$alkenyl, $(C_1-C_6)$haloalkyl, $(C_1-C_6)$alkyl$(C_1-C_6)$alkoxy, $C(=O)(C_1-C_6)$alkyl, and $(C_1-C_6)$alkoxy$C(=O)(C_1-C_6)$alkyl;

$R^{13}$ is selected from the group consisting of H, F, Cl, Br, I, CN, $NH_2$, $NO_2$, CHO, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and triazolyl;

$R^{14}$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^{15}$ is selected from the group consisting of H, $(C_1-C_6)$alkyl, and $(C_2-C_6)$alkenyl;

$R^{16}$ is selected from the group consisting of $(C_1-C_8)$alkyl, $(C_3-C_8)$cycloalkyl, $(C_1-C_8)$alkyl-O—$(C_1-C_8)$alkyl, $(C_1-C_8)$alkyl$(C_3-C_8)$cycloalkyl, $(C_1-C_8)$alkylphenyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, O- phenyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$cycloalkyl, $(C_1-C_8)$alkyl-O—$(C_1-C_8)$haloalkyl, $(C_1-C_8)$alkyl-C(=O)NH—$(C_1-C_8)$haloalkyl, $(C_1-C_8)$ alkyl-NHC(O)—($C_1$-$C_8$)alkyl, ($C_1$-$C_8$)alkyl-S—($C_1$-$C_8$)haloalkyl, ($C_1$-$C_8$)alkyl-S(O)—($C_1$-$C_8$) haloalkyl, ($C_1$-$C_8$)alkyl-S(O)$_2$—($C_1$-$C_8$)haloalkyl, ($C_1$-$C_8$)alkyl-S(O)$_2$—$NH_2$, and a heterocycle, wherein each alkyl, alkenyl, alkynyl, alkyl-cycloalkyl, haloalkyl, and phenyl, may be optionally substituted with one or more substituents selected from the group consisting of F, Cl, Br, I, CN, OH, $NH_2$, $NO_2$, ($C_1$-$C_8$)alkyl, ($C_2$-$C_8$)alkenyl, ($C_2$-$C_8$)alkynyl, ($C_1$-$C_8$)alkoxy, ($C_1$-$C_8$)haloalkyl, N(($C_1$-$C_8$)alkyl)$_2$, C(O)O($C_1$-$C_8$)alkyl, benzothioenyl, oxoimidazolidinyl, furanyl, pyrazolyl, pyridinyl, thiazolyl, and triazolyl, and wherein the heterocycle is selected from the group consisting of, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, and wherein each ($C_3$-$C_8$)cycloalkyl and heterocycle may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, C(═O)O($C_1$-$C_4$)alkyl, (C═O)NH($C_1$-$C_4$)alkyl, (C═O)NH($C_1$-$C_4$)haloalkyl, C(═O)($C_3$-$C_6$)cyclopropyl, C(═O)($C_1$-$C_4$) haloalkyl, C(═O)($C_1$-$C_4$)alkyl($C_1$-$C_4$)alkoxy, and ($C_1$-$C_4$)alkyl-morpholinyl;

$R^{15}$ and $R^{16}$ together can optionally form a 2- to 5-membered saturated or unsaturated, hydrocarbyl link, which may contain one or more heteroatoms selected from the group consisting of nitrogen, sulfur, and oxygen, wherein said hydrocarbyl link may be optionally substituted with one or more substituents selected from the group consisting of F, Cl, Br, I, CN, $NH_2$, and $NO_2$;

$Q^1$ and $Q^2$ are each independently selected from the group consisting of O and S.

In an embodiment of the invention and/or embodiments thereof, the invention is directed to a compound of formula (IV)

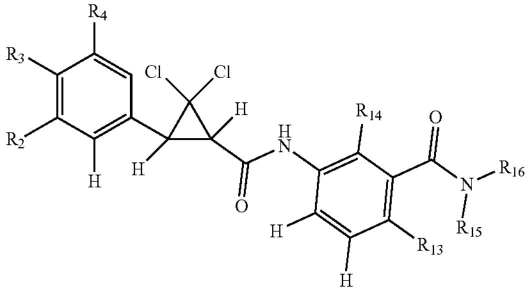

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_1$-$C_6$)haloalkoxy, ($C_1$-$C_6$)alkyl-S(O)$_2$$NH_2$, and S-(Halo)$_5$;

$R^3$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_1$-$C_6$)haloalkoxy, ($C_1$-$C_6$)alkyl-S(O)$_2$$NH_2$, and S-(Halo)$_5$;

$R^4$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, ($C_1$-$C_6$)alkyl-S(O)$_2$$NH_2$, and S-(Halo)$_5$;

$R^5$ is selected from the group consisting of H, F, Cl, Br, I, CN, $NH_2$, $NO_2$, ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_2$-$C_6$)haloalkenyl, and ($C_1$-$C_6$)haloalkoxy;

$R^6$ and $R^9$ are each selected from the group consisting of H, $CH_3$ and $CH_2CH_3$;

$R^7$ and $R^8$ are each selected from the group consisting of Cl and Br;

$R^{10}$ is selected from the group consisting of H, ($C_1$-$C_6$)alkyl, ($C_2$-$C_6$)alkenyl, and ($C_1$-$C_6$)haloalkyl;

$R^{13}$ is selected from the group consisting of H, F, Cl, Br, I, CN, $NH_2$, $NO_2$, CHO, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{14}$ is selected from the group consisting of H, F, Cl, Br, I, CN, $NH_2$, $NO_2$, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{15}$ is selected from the group consisting of H, ($C_1$-$C_6$)alkyl, and ($C_2$-$C_6$)alkenyl;

$R^{16}$ is selected from the group consisting of ($C_1$-$C_8$) alkyl, ($C_3$-$C_8$)cycloalkyl, ($C_1$-$C_8$)alkyl-O—($C_1$-$C_8$) alkyl, ($C_1$-$C_8$)alkyl($C_3$-$C_8$)cycloalkyl, ($C_2$-$C_8$)alkenyl, ($C_2$-$C_8$)alkynyl, ($C_1$-$C_8$)haloalkyl, ($C_1$-$C_8$) alkyl- S—($C_1$-$C_8$)alkyl, ($C_1$-$C_8$)alkyl-S(O)—($C_1$-$C_8$)alkyl, ($C_1$-$C_8$)alkyl-S(O)$_2$—($C_1$-$C_8$)alkyl, ($C_1$-$C_8$)alkyl-O—($C_1$- $C_8$)haloalkyl, ($C_1$-$C_8$)alkyl-S—($C_1$-$C_8$)haloalkyl, ($C_1$-$C_8$)alkyl-S(O)—($C_1$-$C_8$) haloalkyl, ($C_1$-$C_8$)alkyl-S(O)$_2$—($C_1$-$C_8$)haloalkyl, ($C_1$-$C_8$)alkyl-S(O)$_2$—$NH_2$, and heterocycle, wherein each alkyl, alkenyl, alkynyl, alkyl-cycloalkyl, and haloalkyl in $R^{16}$, may be optionally substituted with one or more substituents selected from the group consisting of F, Cl, Br, I, CN, OH, $NH_2$, $NO_2$, ($C_1$-$C_8$) alkyl, ($C_2$-$C_8$)alkenyl, ($C_2$-$C_8$)alkynyl, ($C_1$-$C_8$)alkoxy, ($C_1$-$C_8$)haloalkyl, C(O)O($C_1$-$C_8$)alkyl, oxoimidazolidinyl, furanyl, and pyrazolyl, wherein each ($C_3$-$C_8$)cycloalkyl in $R^{16}$, may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, C(═O)O($C_1$-$C_4$)alkyl, (C═O)NH ($C_1$-$C_4$)alkyl, (C═O)NH($C_1$-$C_4$)haloalkyl, C(═O) ($C_3$-$C_6$)cyclopropyl, C(═O)($C_1$-$C_4$)haloalkyl, C(═O) ($C_1$-$C_4$)alkyl($C_1$-$C_4$)alkoxy, and ($C_1$-$C_4$)alkyl-morpholinyl, wherein the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide, wherein, each heterocycle in $R^{16}$ may be optionally substituted with one or more substituents selected from the group consisting of H, F, Cl, Br, I, CN, oxo, $(C_1-C_4)$alkyl, $(C_2-C_8)$alkenyl, $(C_2-C_8)$alkynyl, $(C_1-C_4)$haloalkyl, (C═O)NH$(C_1-C_4)$alkyl, (C═O)NH$(C_1-C_4)$haloalkyl, and C(═O)$(C_1-C_4)$alkyl$(C_1-C_4)$alkoxy;

$Q^1$ and $Q^2$ are each independently selected from the group consisting of O and S.

In an embodiment of the invention and/or embodiments thereof, the invention is directed to a compound of formula (IV)

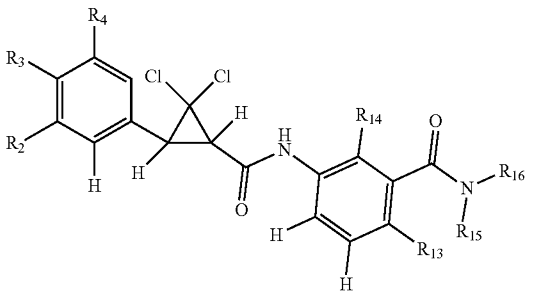

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, and $(C_1-C_6)$haloalkyl;

$R^3$ is selected from the group consisting of H, F, Cl, Br, I, CN, $NH_2$, $NO_2$, $(C_1-C_6)$alkyl, $(C_1-C_6)$alkoxy, $(C_1-C_6)$haloalkyl, and $(C_1-C_6)$haloalkoxy;

$R^4$ is selected from the group consisting of H, F, Cl, Br, I, CN, $NH_2$, $(C_1-C_6)$alkyl, $(C_1-C_6)$alkoxy, $(C_1-C_6)$haloalkyl, and $(C_1-C_6)$haloalkoxy;

$R^5$ is selected from the group consisting of H, F, Cl, Br, $NH_2$, $(C_1-C_6)$alkyl, $(C_1-C_6)$alkoxy, $(C_1-C_6)$haloalkyl, and $(C_1-C_6)$haloalkoxy;

$R^6$ and $R^9$ are each selected from the group consisting of H, and $CH_3$;

$R^7$ and $R^8$ are each selected from the group consisting of Cl and Br;

$R^{10}$ is selected from the group consisting of H, and $CH_3$; preferably $R^{10}$ is H;

$R^{13}$ is selected from the group consisting of H, F, Cl, Br, $CH_3$, $OCH_3$, and $CF_3$;

$R^{14}$ is selected from the group consisting of H, F, Cl, Br, I, $NH_2$, $(C_1-C_6)$alkyl, and $(C_1-C_6)$haloalkyl;

$R^{15}$ is selected from the group consisting of H, and $(C_1-C_6)$alkyl;

$R^{16}$ is selected from the group consisting of $(C_1-C_8)$alkyl, $(C_3-C_8)$cycloalkyl, $(C_1-C_8)$alkyl$(C_3-C_8)$cycloalkyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, and $(C_1-C_8)$alkyl-O—$(C_1-C_8)$haloalkyl, wherein each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$alkoxy, C(O)O$(C_1-C_8)$alkyl, and oxoimidazolidinyl, wherein in $R^{16}$ the $(C_3-C_8)$cycloalkyl, may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, (C═O)NH$(C_1-C_4)$alkyl, and (C═O)NH$(C_1-C_4)$haloalkyl;

$Q^1$ and $Q^2$ are O.

In an embodiment of the invention and/or embodiments thereof, the invention is directed to a compound of formula (IV)

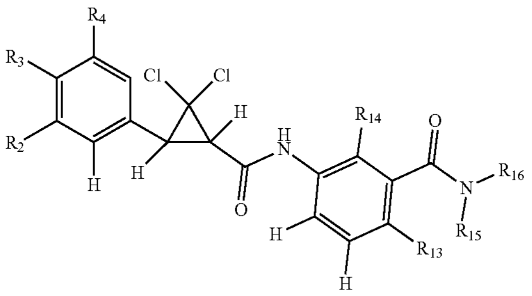

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $(C_1-C_6)$alkyl, $(C_1-C_6)$alkoxy, and $(C_1-C_6)$haloalkyl;

$R^3$ is selected from the group consisting of H, F, Cl, Br, I, CN, $NH_2$, $(C_1-C_6)$alkyl, and $(C_1-C_6)$haloalkyl;

$R^4$ is selected from the group consisting of H, F, Cl, Br, I, $(C_1-C_6)$alkyl, and $(C_1-C_6)$haloalkyl;

$R^5$ is selected from the group consisting of H, F, Cl, Br, $(C_1-C_6)$alkyl, and $(C_1-C_6)$haloalkyl;

$R^6$ and $R^9$ are each H;

$R^7$ and $R^8$ are each Cl;

$R^{10}$ is H;

$R^{13}$ is selected from the group consisting of H, Cl, F, $CH_3$, and $OCH_3$;

$R^{14}$ is selected from the group consisting of H, F, or Cl;

$R^{15}$ is selected from the group consisting of H and $CH_3$;

$R^{16}$ is selected from the group consisting of $(C_1-C_8)$alkyl, $(C_3-C_8)$cycloalkyl, $(C_2-C_8)$alkenyl, $(C_2-C_8)$alkynyl, $(C_1-C_8)$haloalkyl, and $(C_1-C_8)$alkyl-O—$(C_1-C_8)$haloalkyl, wherein each alkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$alkoxy, C(O)O$(C_1-C_8)$alkyl, and oxoimidazolidinyl, wherein the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, $(C_2-C_8)$alkynyl, $(C_1-C_4)$haloalkyl, and (C═O)NH$(C_1-C_4)$alkyl;

$Q^1$ and $Q^2$ are O.

In an embodiment of the invention and/or embodiments thereof, the invention is directed to a compound of formula (IV)

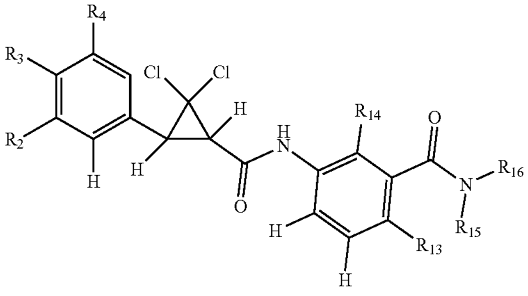

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, CN, $CH_3$, $CHF_2$ and $CF_3$, preferably $R^2$ is selected from the group consisting of H, F, and Cl, preferably $R^2$ is F or Cl;

$R^3$ is selected from the group consisting of H, F, Cl, Br, $CH_3$, $CHF_2$ and $CF_3$, preferably $R^3$ is selected from the group consisting of H, F, Cl, Br and $CHF_2$;

$R^4$ is selected from the group consisting of H, F, Cl, Br, $CH_3$, $CHF_2$ and $CF_3$, preferably $R^4$ is selected from the group consisting of H, F, and Cl, more preferably $R^4$ is F or Cl;

$R^5$ is selected from the group consisting of H, F, and Cl, preferably $R^5$ is H;

$R^6$ and $R^9$ are each H;

$R^7$ and $R^8$ are each Cl;

$R^{10}$ is H;

$R^{13}$ is Cl or F;

$R^{14}$ is H or F preferably H;

$R^{15}$ is H;

$R^{16}$ is selected from the group consisting of ($C_1$-$C_8$)alkyl, ($C_3$-$C_8$)cycloalkyl, ($C_2$-$C_8$)alkenyl, ($C_2$-$C_8$)alkynyl, and ($C_1$-$C_8$)haloalkyl, wherein each alkyl, cycloalkyl, alkenyl, alkynyl, and haloalkyl, may be optionally substituted with one or more substituents selected from the group consisting of F, Cl, Br, ($C_1$-$C_8$)alkyl, ($C_2$-$C_8$)alkenyl, ($C_2$-$C_8$)alkynyl, and ($C_1$-$C_8$)alkoxy, wherein the ($C_3$-$C_8$)cycloalkyl, may be optionally substituted with one or more substituents selected from the group consisting of H, F, Cl, CN, oxo, ($C_1$-$C_4$)alkyl, ($C_2$-$C_8$)alkenyl, and ($C_2$-$C_8$)alkynyl;

$Q^1$ and $Q^2$ are O.

In an embodiment of the invention and/or embodiments thereof, the invention is directed to a compound of formula (V)

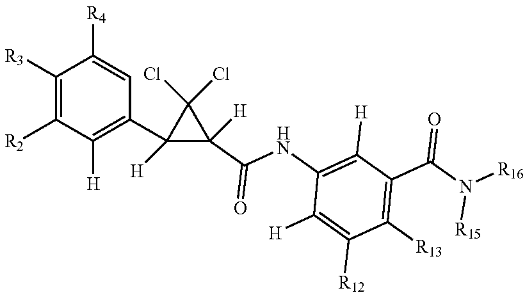

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, $S(O)_2$($C_1$-$C_6$)alkyl, S($C_1$-$C_6$)haloalkyl, S(O)($C_1$-$C_6$)haloalkyl, $S(O)_2$($C_1$-$C_6$)haloalkyl, ($C_1$-$C_6$)alkyl-$S(O)_2NH_2$, ($C_1$-$C_6$)haloalkyl-$S(O)_2NH_2$, and S-$(Halo)_5$;

$R^3$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, $S(O)_2$($C_1$-$C_6$)alkyl, S($C_1$-$C_6$)haloalkyl, S(O)($C_1$-$C_6$)haloalkyl, $S(O)_2$($C_1$-$C_6$)haloalkyl, ($C_1$-$C_6$)alkyl-$S(O)_2NH_2$, ($C_1$-$C_6$)haloalkyl-$S(O)_2NH_2$, and S-$(Halo)_5$;

$R^4$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, $S(O)_2$($C_1$-$C_6$)alkyl, S($C_1$-$C_6$)haloalkyl, S(O)($C_1$-$C_6$)haloalkyl, $S(O)_2$($C_1$-$C_6$)haloalkyl, ($C_1$-$C_6$)alkyl-$S(O)_2NH_2$, ($C_1$-$C_6$)haloalkyl-$S(O)_2NH_2$, and S-$(Halo)_5$;

$R^5$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, $S(O)_2$($C_1$-$C_6$)alkyl, S($C_1$-$C_6$)haloalkyl, S(O)($C_1$-$C_6$)haloalkyl, $S(O)_2$($C_1$-$C_6$)haloalkyl, ($C_1$-$C_6$)alkyl-$S(O)_2NH_2$, and ($C_1$-$C_6$)haloalkyl-$S(O)_2NH_2$;

$R^6$ is selected from the group consisting of H and ($C_1$-$C_6$)alkyl;

$R^7$ is selected from the group consisting of H, F, Cl, Br, and I;

$R^8$ is selected from the group consisting of F, Cl, Br, and I;

$R^9$ is selected from the group consisting of H and ($C_1$-$C_6$)alkyl;

$R^{10}$ is selected from the group consisting of H, ($C_1$-$C_6$)alkyl, ($C_2$-$C_6$)alkenyl, ($C_1$-$C_6$)haloalkyl, ($C_1$-$C_6$)alkyl($C_1$-$C_6$)alkoxy, C(=O)($C_1$-$C_6$)alkyl, and ($C_1$-$C_6$)alkoxyC(=O)($C_1$-$C_6$)alkyl;

$R^{12}$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, $S(O)_2$($C_1$-$C_6$)alkyl, S($C_1$-$C_6$)haloalkyl, S(O)($C_1$-$C_6$)haloalkyl, $S(O)_2$($C_1$-$C_6$)haloalkyl, ($C_1$-$C_6$)alkyl-$S(O)_2NH_2$, and ($C_1$-$C_6$)haloalkyl-$S(O)_2NH_2$;

$R^{13}$ is selected from the group consisting of H, F, Cl, Br, I, CN, $NH_2$, $NO_2$, CHO, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$ halocycloalkenyl, $(C_1-C_6)$haloalkoxy, $S(C_1-C_6)$ alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$ haloalkyl, $(C_1-C_6)$alkyl-$S(O)_2NH_2$, $(C_1-C_6)$ haloalkyl-$S(O)_2NH_2$, and triazolyl;

$R^{15}$ is selected from the group consisting of H, $(C_1-C_6)$alkyl, and $(C_2-C_6)$alkenyl;

$R^{16}$ is selected from the group consisting of $(C_1-C_8)$ alkyl, $(C_3-C_8)$cycloalkyl, $(C_1-C_8)$alkyl-O—$(C_1-C_8)$ alkyl, $(C_1-C_8)$alkyl$(C_3-C_8)$cycloalkyl, $(C_1-C_8)$alkylphenyl, $(C_2-C_8)$alkenyl, $(C_2-C_8)$alkynyl, $(C_1-C_8)$ haloalkyl, $(C_1-C_8)$alkyl-S—$(C_1-C_8)$alkyl, $(C_1-C_8)$ alkyl-S(O)—$(C_1-C_8)$alkyl, $(C_1-C_8)$alkyl-$S(O)_2$—$(C_1-C_8)$alkyl, O- phenyl, O—$(C_2-C_8)$alkenyl, O—$(C_1-C_8)$alkyl$(C_3-C_8)$cycloalkyl, O—$(C_1-C_8)$alkylphenyl, $(C_1-C_8)$alkyl-O—$(C_1-C_8)$alkyl$(C_3-C_8)$ cycloalkyl, $(C_1-C_8)$alkyl-O—$(C_1-C_8)$haloalkyl, $(C_1-C_8)$alkyl-C(═O)NH—$(C_1-C_8)$haloalkyl, $(C_1-C_8)$ alkyl-NHC(O)—$(C_1-C_8)$alkyl, $(C_1-C_8)$alkyl-S—$(C_1-C_8)$haloalkyl, $(C_1-C_8)$alkyl-S(O)—$(C_1-C_8)$ haloalkyl, $(C_1-C_8)$alkyl-$S(O)_2$—$(C_1-C_8)$haloalkyl, $(C_1-C_8)$alkyl-$S(O)_2$—$NH_2$, and a heterocycle, wherein each alkyl, alkenyl, alkynyl, alkyl-cycloalkyl, haloalkyl, and phenyl, may be optionally substituted with one or more substituents selected from the group consisting of F, Cl, Br, I, CN, OH, $NH_2$, $NO_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $N((C_1-C_8)alkyl)_2$, $C(O)O(C_1-C_8)$alkyl, benzothioenyl, oxoimidazolidinyl, furanyl, pyrazolyl, pyridinyl, thiazolyl, and triazolyl, and wherein the heterocycle is selected from the group consisting of, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, and wherein each $(C_3-C_8)$cycloalkyl and heterocycle may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, C(═O)O$(C_1-C_4)$alkyl, (C═O)NH$(C_1-C_4)$alkyl, (C═O)NH$(C_1-C_4)$haloalkyl, C(═O)$(C_3-C_6)$cyclopropyl, C(═O)$(C_1-C_4)$ haloalkyl, C(═O)$(C_1-C_4)$alkyl$(C_1-C_4)$alkoxy, and $(C_1-C_4)$alkyl-morpholinyl;

$R^{15}$ and $R^{16}$ together can optionally form a 2- to 5-membered saturated or unsaturated, hydrocarbyl link, which may contain one or more heteroatoms selected from the group consisting of nitrogen, sulfur, and oxygen, wherein said hydrocarbyl link may be optionally substituted with one or more substituents selected from the group consisting of F, Cl, Br, I, CN, $NH_2$, and $NO_2$;

$Q^1$ and $Q^2$ are each independently selected from the group consisting of O and S.

In an embodiment of the invention and/or embodiments thereof, the invention is directed to a compound of formula (V)

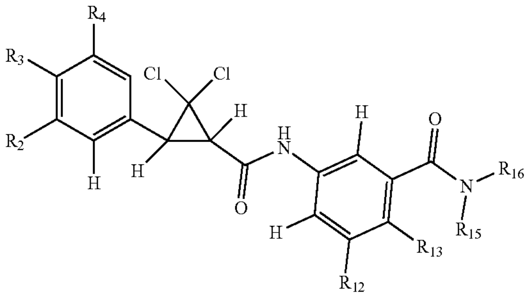

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_1-C_6)$haloalkoxy, $(C_1-C_6)$alkyl-$S(O)_2NH_2$, and S-$(Halo)_5$;

$R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_1-C_6)$haloalkoxy, $(C_1-C_6)$alkyl-$S(O)_2NH_2$, and S-$(Halo)_5$;

$R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $(C_1-C_6)$alkyl-$S(O)_2NH_2$, and S-$(Halo)_5$;

$R^5$ is selected from the group consisting of H, F, Cl, Br, I, CN, $NH_2$, $NO_2$, $(C_1-C_6)$alkyl, $(C_2-C_6)$alkenyl, $(C_2-C_6)$alkynyl, $(C_1-C_6)$alkoxy, $(C_1-C_6)$haloalkyl, $(C_2-C_6)$haloalkenyl, and $(C_1-C_6)$haloalkoxy;

$R^6$ and $R^9$ are each selected from the group consisting of H, $CH_3$ and $CH_2CH_3$;

$R^7$ and $R^8$ are each selected from the group consisting of Cl and Br;

$R^{10}$ is selected from the group consisting of H, $(C_1-C_6)$alkyl, $(C_2-C_6)$alkenyl, and $(C_1-C_6)$haloalkyl;

$R^{12}$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, $(C_1-C_6)$haloalkyl, $(C_2-C_6)$haloalkenyl, and $(C_1-C_6)$haloalkoxy;

$R^{13}$ is selected from the group consisting of H, F, Cl, Br, I, CN, $NH_2$, $NO_2$, CHO, $(C_1-C_6)$alkyl, $(C_2-C_6)$alkenyl, $(C_1-C_6)$alkoxy, $(C_1-C_6)$haloalkyl, $(C_2-C_6)$haloalkenyl, and $(C_1-C_6)$haloalkoxy;

$R^{15}$ is selected from the group consisting of H, $(C_1-C_6)$alkyl, and $(C_2-C_6)$alkenyl;

$R^{16}$ is selected from the group consisting of $(C_1-C_8)$ alkyl, $(C_3-C_8)$cycloalkyl, $(C_1-C_8)$alkyl-O—$(C_1-C_8)$ alkyl, $(C_1-C_8)$alkyl$(C_3-C_8)$cycloalkyl, $(C_2-C_8)$alkenyl, $(C_2-C_8)$alkynyl, $(C_1-C_8)$haloalkyl, $(C_1-C_8)$ alkyl- S—$(C_1-C_8)$alkyl, $(C_1-C_8)$alkyl-S(O)—$(C_1-$ $C_8$)alkyl, ($C_1$-$C_8$)alkyl-S(O)$_2$—($C_1$-$C_8$)alkyl, ($C_1$-$C_8$)alkyl-O—($C_1$- $C_8$)haloalkyl, ($C_1$-$C_8$)alkyl-S—($C_1$-$C_8$)haloalkyl, ($C_1$-$C_8$)alkyl-S(O)—($C_1$-$C_8$) haloalkyl, ($C_1$-$C_8$)alkyl-S(O)$_2$—($C_1$-$C_8$)haloalkyl, ($C_1$-$C_8$)alkyl-S(O)$_2$—$NH_2$, and heterocycle, wherein each alkyl, alkenyl, alkynyl, alkyl-cycloalkyl, and haloalkyl in $R^{16}$, may be optionally substituted with one or more substituents selected from the group consisting of F, Cl, Br, I, CN, OH, $NH_2$, $NO_2$, ($C_1$-$C_8$) alkyl, ($C_2$-$C_8$)alkenyl, ($C_2$-$C_8$)alkynyl, ($C_1$-$C_8$)alkoxy, ($C_1$-$C_8$)haloalkyl, C(O)O($C_1$-$C_8$)alkyl, oxoimidazolidinyl, furanyl, and pyrazolyl, wherein each ($C_3$-$C_8$)cycloalkyl in $R^{16}$, may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, C(=O)O($C_1$-$C_4$)alkyl, (C=O)NH ($C_1$-$C_4$)alkyl, (C=O)NH($C_1$-$C_4$)haloalkyl, C(=O) ($C_3$-$C_6$)cyclopropyl, C(=O)($C_1$-$C_4$)haloalkyl, C(=O) ($C_1$-$C_4$)alkyl($C_1$-$C_4$)alkoxy, and ($C_1$-$C_4$)alkyl-morpholinyl, wherein the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide, wherein, each heterocycle in $R^{16}$ may be optionally substituted with one or more substituents selected from the group consisting of H, F, Cl, Br, I, CN, oxo, ($C_1$-$C_4$) alkyl, ($C_2$-$C_8$)alkenyl, ($C_2$-$C_8$)alkynyl, ($C_1$-$C_4$)haloalkyl, (C=O)NH($C_1$-$C_4$)alkyl, (C=O)NH($C_1$-$C_4$)haloalkyl, and C(=O)($C_1$-$C_4$)alkyl($C_1$-$C_4$)alkoxy;

$Q^1$ and $Q^2$ are each independently selected from the group consisting of O and S.

In an embodiment of the invention and/or embodiments thereof, the invention is directed to a compound of formula (V)

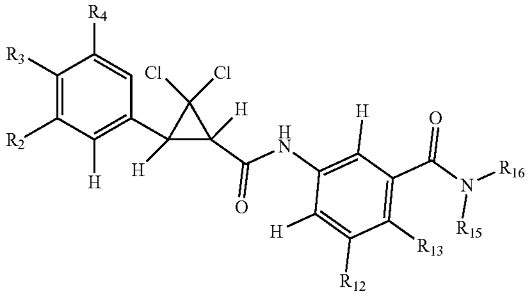

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, ($C_1$-$C_6$)alkyl, ($C_2$-$C_6$)alkenyl, ($C_1$-$C_6$)alkoxy, and ($C_1$-$C_6$)haloalkyl;

$R^3$ is selected from the group consisting of H, F, Cl, Br, I, CN, $NH_2$, $NO_2$, ($C_1$-$C_6$)alkyl, ($C_1$-$C_6$)alkoxy, ($C_1$-$C_6$)haloalkyl, and ($C_1$-$C_6$)haloalkoxy;

$R^4$ is selected from the group consisting of H, F, Cl, Br, I, CN, $NH_2$, ($C_1$-$C_6$)alkyl, ($C_1$-$C_6$)alkoxy, ($C_1$-$C_6$) haloalkyl, and ($C_1$-$C_6$)haloalkoxy;

$R^5$ is selected from the group consisting of H, F, Cl, Br, $NH_2$, ($C_1$-$C_6$)alkyl, ($C_1$-$C_6$)alkoxy, ($C_1$-$C_6$)haloalkyl, and ($C_1$-$C_6$)haloalkoxy;

$R^6$ and $R^9$ are each selected from the group consisting of H, and $CH_3$;

$R^7$ and $R^8$ are each selected from the group consisting of Cl and Br;

$R^{10}$ is selected from the group consisting of H, and $CH_3$; preferably $R^{10}$ is H;

$R^{12}$ is selected from the group consisting of H, F, Cl, Br, I, ($C_1$-$C_6$)alkyl, and ($C_1$-$C_6$)haloalkyl;

$R^{13}$ is selected from the group consisting of H, F, Cl, Br, $CH_3$, $OCH_3$, and $CF_3$;

$R^{15}$ is selected from the group consisting of H, and ($C_1$-$C_6$)alkyl;

$R^{16}$ is selected from the group consisting of ($C_1$-$C_8$) alkyl, ($C_3$-$C_8$)cycloalkyl, ($C_1$-$C_8$)alkyl($C_3$-$C_8$)cycloalkyl, ($C_2$-$C_8$)alkenyl, ($C_2$-$C_8$)alkynyl, ($C_1$-$C_8$) haloalkyl, ($C_1$-$C_8$)alkyl-S—($C_1$-$C_8$)alkyl, ($C_1$-$C_8$) alkyl-S(O)—($C_1$-$C_8$)alkyl, ($C_1$-$C_8$)alkyl-S(O)$_2$—($C_1$-$C_8$)alkyl, and ($C_1$-$C_8$)alkyl-O—($C_1$-$C_8$) haloalkyl, wherein each alkyl, cycloalkyl, alkenyl, alkynyl, and haloalkyl, may be optionally substituted with one or more substituents selected from the group consisting of F, Cl, Br, ($C_1$-$C_8$)alkyl, ($C_2$-$C_8$)alkenyl, ($C_2$-$C_8$)alkynyl, ($C_1$-$C_8$)alkoxy, C(O)O($C_1$-$C_8$)alkyl, and oxoimidazolidinyl, wherein in $R^{16}$ the ($C_3$-$C_8$)cycloalkyl, may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, (C=O)NH($C_1$-$C_4$)alkyl, and (C=O)NH($C_1$-$C_4$)haloalkyl;

$Q^1$ and $Q^2$ are O.

In an embodiment of the invention and/or embodiments thereof, the invention is directed to a compound of formula (V)

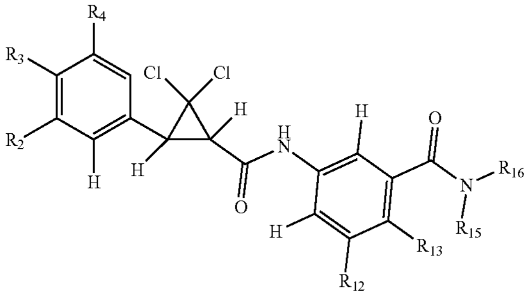

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, ($C_1$-$C_6$)alkyl, ($C_1$-$C_6$)alkoxy, and ($C_1$-$C_6$)haloalkyl;

$R^3$ is selected from the group consisting of H, F, Cl, Br, I, CN, $NH_2$, ($C_1$-$C_6$)alkyl, and ($C_1$-$C_6$)haloalkyl;

$R^4$ is selected from the group consisting of H, F, Cl, Br, I, ($C_1$-$C_6$)alkyl, and ($C_1$-$C_6$)haloalkyl;

$R^5$ is selected from the group consisting of H, F, Cl, Br, ($C_1$-$C_6$)alkyl, and ($C_1$-$C_6$)haloalkyl;

$R^6$ and $R^8$ are each H;

$R^7$ and $R^8$ are each Cl;

$R^{10}$ is H;

$R^{12}$ is selected from the group consisting of H, F, Cl, $CH_3$, and $CF_3$;

$R^{13}$ is selected from the group consisting of H, Cl, F, $CH_3$, and $OCH_3$;

$R^{15}$ is selected from the group consisting of H and $CH_3$;

$R^{16}$ is selected from the group consisting of ($C_1$-$C_8$)alkyl, ($C_3$-$C_8$)cycloalkyl, ($C_2$-$C_8$)alkenyl, ($C_2$-$C_8$)alkynyl, ($C_1$-$C_8$)haloalkyl, and ($C_1$-$C_8$)alkyl-O—($C_1$-$C_8$)haloalkyl, wherein each alkyl, alkenyl, alkynyl, and haloalkyl, may be optionally substituted with one or more substituents selected from the group consisting of F, Cl, Br, ($C_1$-$C_8$)alkyl, ($C_2$-$C_8$)alkenyl, ($C_2$-$C_8$)alkynyl, ($C_1$-$C_8$)alkoxy, C(O)O($C_1$-$C_8$)alkyl, and oxoimidazolidinyl, wherein the ($C_3$-$C_8$)cycloalkyl, may be optionally substituted with one or more substituents selected from the group consisting of H, F, Cl, CN, oxo, ($C_1$-$C_4$)alkyl, ($C_2$-$C_8$)alkenyl, ($C_2$-$C_8$)alkynyl, ($C_1$-$C_4$)haloalkyl, and (C═O)NH($C_1$-$C_4$)alkyl;

$Q^1$ and $Q^2$ are O.

In an embodiment of the invention and/or embodiments thereof, the invention is directed to a compound of formula (V)

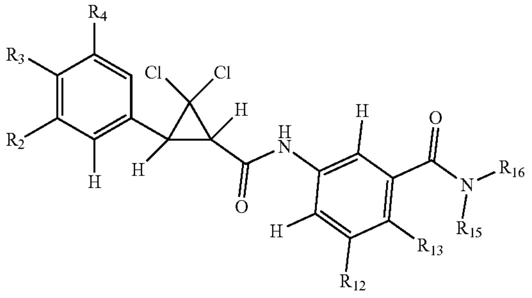

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, CN, $CH_3$, $CHF_2$ and $CF_3$, preferably $R^2$ is selected from the group consisting of H, F, and Cl, preferably $R^2$ is F or Cl;

$R^3$ is selected from the group consisting of H, F, Cl, Br, $CH_3$, $CHF_2$ and $CF_3$, preferably $R^3$ is selected from the group consisting of H, F, Cl, Br and $CHF_2$;

$R^4$ is selected from the group consisting of H, F, Cl, Br, $CH_3$, $CHF_2$ and $CF_3$, preferably $R^4$ is selected from the group consisting of H, F, and Cl, more preferably $R^4$ is F or Cl;

$R^5$ is selected from the group consisting of H, F, and Cl, preferably $R^5$ is H;

$R^6$ and $R^9$ are each H;

$R^7$ and $R^8$ are each Cl;

$R^{10}$ is H;

$R^{12}$ is selected from the group consisting of H, F, Cl, $CH_3$, and $CF_3$;

$R^{13}$ is Cl or F;

$R^{15}$ is H;

$R^{16}$ is selected from the group consisting of ($C_1$-$C_8$)alkyl, ($C_3$-$C_8$)cycloalkyl, ($C_2$-$C_8$)alkenyl, ($C_2$-$C_8$)alkynyl, and ($C_1$-$C_8$)haloalkyl, wherein each alkyl, cycloalkyl, alkenyl, alkynyl, and haloalkyl, may be optionally substituted with one or more substituents selected from the group consisting of F, Cl, Br, ($C_1$-$C_8$)alkyl, ($C_2$-$C_8$)alkenyl, ($C_2$-$C_8$)alkynyl, and ($C_1$-$C_8$)alkoxy, wherein the ($C_3$-$C_8$)cycloalkyl, may be optionally substituted with one or more substituents selected from the group consisting of H, F, Cl, CN, oxo, ($C_1$-$C_4$)alkyl, ($C_2$-$C_8$)alkenyl, and ($C_2$-$C_8$)alkynyl;

$Q^1$ and $Q^2$ are O.

In an embodiment of the invention and/or embodiments thereof, the invention is directed to a compound of formula (VI)

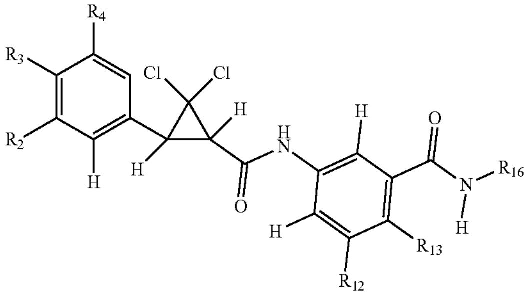

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, $S(O)_2$($C_1$-$C_6$)alkyl, S($C_1$-$C_6$)haloalkyl, S(O)($C_1$-$C_6$)haloalkyl, $S(O)_2$($C_1$-$C_6$)haloalkyl, ($C_1$-$C_6$)alkyl-$S(O)_2NH_2$, ($C_1$-$C_6$)haloalkyl-$S(O)_2NH_2$, and S-$(Halo)_5$;

$R^3$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, $S(O)_2$($C_1$-$C_6$)alkyl, S($C_1$-$C_6$)haloalkyl, S(O)($C_1$-$C_6$)haloalkyl, $S(O)_2$($C_1$-$C_6$)haloalkyl, ($C_1$-$C_6$)alkyl-$S(O)_2NH_2$, ($C_1$-$C_6$)haloalkyl-$S(O)_2NH_2$, and S-$(Halo)_5$;

$R^4$ is selected from the group consisting of H, F, Cl, Br, I, CN, $NH_2$, $NO_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, $S(O)_2$($C_1$-$C_6$)alkyl, S($C_1$-$C_6$)haloalkyl, S(O)($C_1$-$C_6$)haloalkyl, $S(O)_2$($C_1$-$C_6$)haloalkyl, ($C_1$-$C_6$)alkyl-$S(O)_2NH_2$, ($C_1$-$C_6$)haloalkyl-$S(O)_2NH_2$, and S-$(Halo)_5$;

$R^5$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^6$ is selected from the group consisting of H and $(C_1\text{-}C_6)$alkyl;

$R^7$ is selected from the group consisting of H, F, Cl, Br, and I;

$R^8$ is selected from the group consisting of F, Cl, Br, and I;

$R^9$ is selected from the group consisting of H and $(C_1\text{-}C_6)$alkyl;

$R^{10}$ is selected from the group consisting of H, $(C_1\text{-}C_6)$alkyl, $(C_2\text{-}C_6)$alkenyl, $(C_1\text{-}C_6)$haloalkyl, $(C_1\text{-}C_6)$alkyl$(C_1\text{-}C_6)$alkoxy, $C({=}O)(C_1\text{-}C_6)$alkyl, and $(C_1\text{-}C_6)$alkoxy$C({=}O)(C_1\text{-}C_6)$alkyl; $R^{12}$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^{13}$ is selected from the group consisting of H, F, Cl, Br, I, CN, $NH_2$, $NO_2$, CHO, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, $(C_1\text{-}C_6)$haloalkyl-$S(O)_2NH_2$, and triazolyl;

$R^{16}$ is selected from the group consisting of $(C_1\text{-}C_8)$alkyl, $(C_3\text{-}C_8)$cycloalkyl, $(C_1\text{-}C_8)$alkyl-O—$(C_1\text{-}C_8)$alkyl, $(C_1\text{-}C_8)$alkyl$(C_3\text{-}C_8)$cycloalkyl, $(C_1\text{-}C_8)$alkylphenyl, $(C_2\text{-}C_8)$alkenyl, $(C_2\text{-}C_8)$alkynyl, $(C_1\text{-}C_8)$haloalkyl, $(C_1\text{-}C_8)$alkyl-S—$(C_1\text{-}C_8)$alkyl, $(C_1\text{-}C_8)$alkyl-S(O)—$(C_1\text{-}C_8)$alkyl, $(C_1\text{-}C_8)$alkyl-$S(O)_2$—$(C_1\text{-}C_8)$alkyl, O- phenyl, O—$(C_2\text{-}C_8)$alkenyl, O—$(C_1\text{-}C_8)$alkyl$(C_3\text{-}C_8)$cycloalkyl, O—$(C_1\text{-}C_8)$alkylphenyl, $(C_1\text{-}C_8)$alkyl-O—$(C_1\text{-}C_8)$alkyl$(C_3\text{-}C_8)$cycloalkyl, $(C_1\text{-}C_8)$alkyl-O—$(C_1\text{-}C_8)$haloalkyl, $(C_1\text{-}C_8)$alkyl-$C({=}O)NH$—$(C_1\text{-}C_8)$haloalkyl, $(C_1\text{-}C_8)$alkyl-NHC(O)—$(C_1\text{-}C_8)$alkyl, $(C_1\text{-}C_8)$alkyl-S—$(C_1\text{-}C_8)$haloalkyl, $(C_1\text{-}C_8)$alkyl-S(O)—$(C_1\text{-}C_8)$haloalkyl, $(C_1\text{-}C_8)$alkyl-$S(O)_2$—$(C_1\text{-}C_8)$haloalkyl, $(C_1\text{-}C_8)$alkyl-$S(O)_2$—$NH_2$, and a heterocycle, wherein each alkyl, alkenyl, alkynyl, alkyl-cycloalkyl, haloalkyl, and phenyl, may be optionally substituted with one or more substituents selected from the group consisting of F, Cl, Br, I, CN, OH, $NH_2$, $NO_2$, $(C_1\text{-}C_8)$alkyl, $(C_2\text{-}C_8)$alkenyl, $(C_2\text{-}C_8)$alkynyl, $(C_1\text{-}C_8)$alkoxy, $(C_1\text{-}C_8)$haloalkyl, $N((C_1\text{-}C_8)alkyl)_2$, $C(O)O(C_1\text{-}C_8)$alkyl, benzothioenyl, oxoimidazolidinyl, furanyl, pyrazolyl, pyridinyl, thiazolyl, and triazolyl, and wherein the heterocycle is selected from the group consisting of, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, and wherein each $(C_3\text{-}C_8)$cycloalkyl and heterocycle may be optionally substituted with one or more substituents selected from the group consisting of H, F, Cl, Br, I, CN, $NH_2$, $NO_2$, oxo, $(C_1\text{-}C_4)$alkyl, $(C_2\text{-}C_8)$alkenyl, $(C_2\text{-}C_8)$alkynyl, $(C_1\text{-}C_4)$haloalkyl, $C({=}O)O(C_1\text{-}C_4)$alkyl, $(C{=}O)NH(C_1\text{-}C_4)$alkyl, $(C{=}O)NH(C_1\text{-}C_4)$haloalkyl, $C({=}O)(C_3\text{-}C_6)$cyclopropyl, $C({=}O)(C_1\text{-}C_4)$haloalkyl, $C({=}O)(C_1\text{-}C_4)$alkyl$(C_1\text{-}C_4)$alkoxy, and $(C_1\text{-}C_4)$alkyl-morpholinyl;

$Q^1$ and $Q^2$ are each independently selected from the group consisting of O and S.

In an embodiment of the invention and/or embodiments thereof, the invention is directed to a compound of formula (VI)

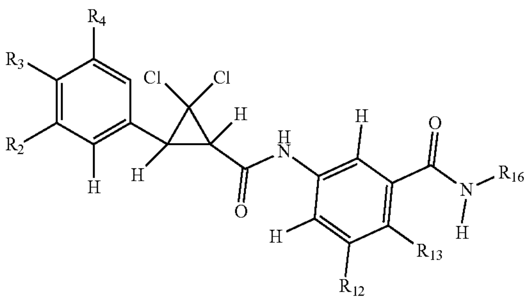

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_1\text{-}C_6)$haloalkoxy, $(C_1\text{-}C_6)$alkyl-$S(O)_2NH_2$, and S-$(Halo)_5$;

$R^3$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_1\text{-}C_6)$haloalkoxy, $(C_1\text{-}C_6)$alkyl-$S(O)_2NH_2$, and S-$(Halo)_5$;

$R^4$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $(C_1\text{-}C_6)$alkyl-$S(O)_2NH_2$, and S-$(Halo)_5$;

$R^5$ is selected from the group consisting of H, F, Cl, Br, I, CN, $NH_2$, $NO_2$, $(C_1\text{-}C_6)$alkyl, $(C_2\text{-}C_6)$alkenyl, $(C_2\text{-}C_6)$alkynyl, $(C_1\text{-}C_6)$alkoxy, $(C_1\text{-}C_6)$haloalkyl, $(C_2\text{-}C_6)$haloalkenyl, and $(C_1\text{-}C_6)$haloalkoxy;

$R^6$ and $R^9$ are each selected from the group consisting of H, $CH_3$ and $CH_2CH_3$;

$R^7$ and $R^8$ are each selected from the group consisting of Cl and Br;

$R^{10}$ is selected from the group consisting of H, $(C_1-C_6)$alkyl, $(C_2-C_6)$alkenyl, and $(C_1-C_6)$haloalkyl;

$R^{12}$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, $(C_1-C_6)$haloalkyl, $(C_2-C_6)$haloalkenyl, and $(C_1-C_6)$haloalkoxy;

$R^{13}$ is selected from the group consisting of H, F, Cl, Br, I, CN, $NH_2$, $NO_2$, CHO, $(C_1-C_6)$alkyl, $(C_2-C_6)$alkenyl, $(C_1-C_6)$alkoxy, $(C_1-C_6)$haloalkyl, $(C_2-C_6)$haloalkenyl, and $(C_1-C_6)$haloalkoxy;

$R^{16}$ is selected from the group consisting of $(C_1-C_8)$alkyl, $(C_3-C_8)$cycloalkyl, $(C_1-C_8)$alkyl-O—$(C_1-C_8)$alkyl, $(C_1-C_8)$alkyl$(C_3-C_8)$cycloalkyl, $(C_2-C_8)$alkenyl, $(C_2-C_8)$alkynyl, $(C_1-C_8)$haloalkyl, $(C_1-C_8)$alkyl- S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, $(C_1-C_8)$alkyl-O—$(C_1$- $C_8)$haloalkyl, $(C_1$—$C_8)$alkyl-S—$(C_1-C_8)$haloalkyl, $(C_1-C_8)$alkyl-S(O)—$(C_1-C_8)$haloalkyl, $(C_1-C_8)$alkyl-$S(O)_2$—$(C_1-C_8)$haloalkyl, $(C_1-C_8)$alkyl-$S(O)_2$—$NH_2$, and heterocycle, wherein each alkyl, alkenyl, alkynyl, alkyl-cycloalkyl, and haloalkyl in $R^{16}$, may be optionally substituted with one or more substituents selected from the group consisting of F, Cl, Br, I, CN, OH, $NH_2$, $NO_2$, $(C_1-C_8)$alkyl, $(C_2-C_8)$alkenyl, $(C_2-C_8)$alkynyl, $(C_1-C_8)$alkoxy, $(C_1-C_8)$haloalkyl, $C(O)O(C_1-C_8)$alkyl, oxoimidazolidinyl, furanyl, and pyrazolyl, wherein each $(C_3-C_8)$cycloalkyl in $R^{16}$, may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, $C(=O)O(C_1-C_4)$alkyl, $(C=O)NH(C_1-C_4)$alkyl, $(C=O)NH(C_1-C_4)$haloalkyl, $C(=O)(C_3-C_6)$cyclopropyl, $C(=O)(C_1-C_4)$haloalkyl, $C(=O)(C_1-C_4)$alkyl$(C_1-C_4)$alkoxy, and $(C_1-C_4)$alkyl-morpholinyl, wherein the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide, wherein, each heterocycle in $R^{16}$ may be optionally substituted with one or more substituents selected from the group consisting of H, F, Cl, Br, I, CN, oxo, $(C_1-C_4)$alkyl, $(C_2-C_8)$alkenyl, $(C_2-C_8)$alkynyl, $(C_1-C_4)$haloalkyl, $(C=O)NH(C_1-C_4)$alkyl, $(C=O)NH(C_1-C_4)$haloalkyl, and $C(=O)(C_1-C_4)$alkyl$(C_1-C_4)$alkoxy;

$Q^1$ and $Q^2$ are each independently selected from the group consisting of O and S.

In an embodiment of the invention and/or embodiments thereof, the invention is directed to a compound of formula (VI)

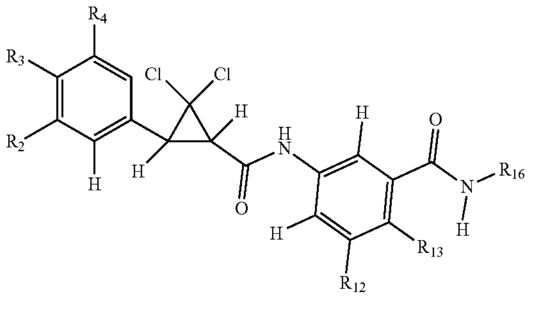

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1-C_6)$alkyl, $(C_2-C_6)$alkenyl, $(C_1-C_6)$alkoxy, and $(C_1-C_6)$haloalkyl;

$R^3$ is selected from the group consisting of H, F, Cl, Br, I, CN, $NH_2$, $NO_2$, $(C_1-C_6)$alkyl, $(C_1-C_6)$alkoxy, $(C_1-C_6)$haloalkyl, and $(C_1-C_6)$haloalkoxy;

$R^4$ is selected from the group consisting of H, F, Cl, Br, I, CN, $NH_2$, $(C_1-C_6)$alkyl, $(C_1-C_6)$alkoxy, $(C_1-C_6)$haloalkyl, and $(C_1-C_6)$haloalkoxy;

$R^5$ is selected from the group consisting of H, F, Cl, Br, $NH_2$, $(C_1-C_6)$alkyl, $(C_1-C_6)$alkoxy, $(C_1-C_6)$haloalkyl, and $(C_1-C_6)$haloalkoxy;

$R^6$ and $R^9$ are each selected from the group consisting of H, and $CH_3$;

$R^7$ and $R^8$ are each selected from the group consisting of Cl and Br;

$R^{10}$ is selected from the group consisting of H, and $CH_3$; preferably $R^{10}$ is H;

$R^{12}$ is selected from the group consisting of H, F, Cl, Br, I, $(C_1-C_6)$alkyl, and $(C_1-C_6)$haloalkyl;

$R^{13}$ is selected from the group consisting of H, F, Cl, Br, $CH_3$, $OCH_3$, and $CF_3$;

$R^{16}$ is selected from the group consisting of $(C_1-C_8)$alkyl, $(C_3-C_8)$cycloalkyl, $(C_1-C_8)$alkyl$(C_3-C_8)$cycloalkyl, $(C_2-C_8)$alkenyl, $(C_2-C_8)$alkynyl, $(C_1-C_8)$haloalkyl, $(C_1-C_8)$alkyl-S—$(C_1-C_8)$alkyl, $(C_1-C_8)$alkyl-S(O)—$(C_1-C_8)$alkyl, $(C_1-C_8)$alkyl-$S(O)_2$—$(C_1-C_8)$alkyl, and $(C_1-C_8)$alkyl-O—$(C_1-C_8)$haloalkyl, wherein each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$alkoxy, $C(O)O(C_1-C_8)$alkyl, and oxoimidazolidinyl, wherein in $R^{16}$ the $(C_3-C_8)$cycloalkyl, may be optionally substituted with one or more substituents selected from the group consisting of H, F, Cl, Br, I, CN, $NH_2$, $NO_2$, oxo, $(C_1-C_4)$alkyl, $(C_2-C_8)$alkenyl, $(C_2-C_8)$alkynyl, $(C_1-C_4)$haloalkyl, $(C=O)NH(C_1-C_4)$alkyl, and $(C=O)NH(C_1-C_4)$haloalkyl;

$Q^1$ and $Q^2$ are O.

In an embodiment of the invention and/or embodiments thereof, the invention is directed to a compound of formula (VI)

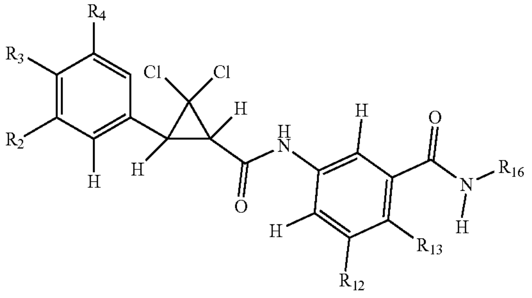

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $(C_1-C_6)$alkyl, $(C_1-C_6)$alkoxy, and $(C_1-C_6)$haloalkyl;

$R^3$ is selected from the group consisting of H, F, Cl, Br, I, CN, $NH_2$, $(C_1-C_6)$alkyl, and $(C_1-C_6)$haloalkyl;

$R^4$ is selected from the group consisting of H, F, Cl, Br, I, $(C_1-C_6)$alkyl, and $(C_1-C_6)$haloalkyl;

$R^5$ is selected from the group consisting of H, F, Cl, Br, $(C_1-C_6)$alkyl, and $(C_1-C_6)$haloalkyl;

$R^6$ and $R^9$ are each H;

$R^7$ and $R^8$ are each Cl;

$R^{10}$ is H;

$R^{12}$ is selected from the group consisting of H, F, Cl, $CH_3$, and $CF_3$;

$R^{13}$ is selected from the group consisting of H, Cl, F, $CH_3$, and $OCH_3$;

$R^{16}$ is selected from the group consisting of $(C_1-C_8)$alkyl, $(C_3-C_8)$cycloalkyl, $(C_2-C_8)$alkenyl, $(C_2-C_8)$alkynyl, $(C_1-C_8)$haloalkyl, and $(C_1-C_8)$alkyl-O—$(C_1-C_8)$haloalkyl, wherein each alkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$alkoxy, $C(O)O(C_1-C_8)$alkyl, and oxoimidazolidinyl, wherein the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, $(C_2-C_8)$alkynyl, $(C_1-C_4)$haloalkyl, and $(C{=}O)NH(C_1-C_4)$alkyl;

$Q^1$ and $Q^2$ are O.

In an embodiment of the invention and/or embodiments thereof, the invention is directed to a compound of formula (VI)

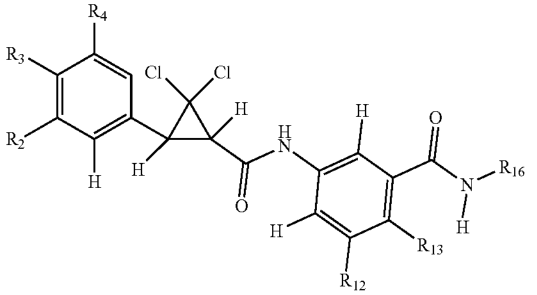

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, CN, $CH_3$, $CHF_2$ and $CF_3$, preferably $R^2$ is selected from the group consisting of H, F, and Cl, preferably $R^2$ is F or Cl;

$R^3$ is selected from the group consisting of H, F, Cl, Br, $CH_3$, $CHF_2$ and $CF_3$, preferably $R^3$ is selected from the group consisting of H, F, Cl, Br and $CHF_2$;

$R^4$ is selected from the group consisting of H, F, Cl, Br, $CH_3$, $CHF_2$ and $CF_3$, preferably $R^4$ is selected from the group consisting of H, F, and Cl, more preferably $R^4$ is F or Cl;

$R^5$ is selected from the group consisting of H, F, and Cl, preferably $R^5$ is H;

$R^6$ and $R^9$ are each H;

$R^7$ and $R^8$ are each Cl;

$R^{10}$ is H;

$R^{12}$ is selected from the group consisting of H, F, Cl, $CH_3$, and $CF_3$;

$R^{13}$ is Cl or F;

$R^{16}$ is selected from the group consisting of $(C_1-C_8)$alkyl, $(C_3-C_8)$cycloalkyl, $(C_2-C_8)$alkenyl, $(C_2-C_8)$alkynyl, and $(C_1-C_8)$haloalkyl, wherein each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, and $(C_1-C_8)$alkoxy, wherein the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, and $(C_2-C_8)$alkynyl;

$Q^1$ and $Q^2$ are O.

In an embodiment of the invention and/or embodiments thereof, the invention is directed to a compound of formula (VII)

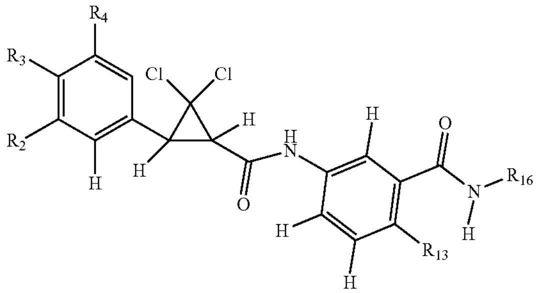

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, S(O)$_2$($C_1$-$C_6$)alkyl, S($C_1$-$C_6$)haloalkyl, S(O)($C_1$-$C_6$)haloalkyl, S(O)$_2$($C_1$-$C_6$)haloalkyl, ($C_1$-$C_6$)alkyl-S(O)$_2$NH$_2$, ($C_1$-$C_6$)haloalkyl-S(O)$_2$NH$_2$, and S-(Halo)$_5$;

$R^5$ is selected from the group consisting of H, F, Cl, Br, I, CN, NH$_2$, NO$_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, S(O)$_2$($C_1$-$C_6$)alkyl, S($C_1$-$C_6$)haloalkyl, S(O)($C_1$-$C_6$)haloalkyl, S(O)$_2$($C_1$-$C_6$)haloalkyl, ($C_1$-$C_6$)alkyl-S(O)$_2$NH$_2$, and ($C_1$-$C_6$)haloalkyl-S(O)$_2$NH$_2$;

$R^6$ is selected from the group consisting of H and ($C_1$-$C_6$)alkyl;

$R^7$ is selected from the group consisting of H, F, Cl, Br, and I;

$R^8$ is selected from the group consisting of F, Cl, Br, and I;

$R^9$ is selected from the group consisting of H and ($C_1$-$C_6$)alkyl;

$R^{10}$ is selected from the group consisting of H, ($C_1$-$C_6$)alkyl, ($C_2$-$C_6$)alkenyl, ($C_1$-$C_6$)haloalkyl, ($C_1$-$C_6$)alkyl($C_1$-$C_6$)alkoxy, C(=O)($C_1$-$C_6$)alkyl, and ($C_1$-$C_6$)alkoxyC(=O)($C_1$-$C_6$)alkyl;

$R^{13}$ is selected from the group consisting of H, F, Cl, Br, I, CN, NH$_2$, NO$_2$, CHO, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, S($C_1$-$C_6$)alkyl, S(O)($C_1$-$C_6$)alkyl, S(O)$_2$($C_1$-$C_6$)alkyl, S($C_1$-$C_6$)haloalkyl, S(O)($C_1$-$C_6$)haloalkyl, S(O)$_2$($C_1$-$C_6$)haloalkyl, ($C_1$-$C_6$)alkyl-S(O)$_2$NH$_2$, ($C_1$-$C_6$)haloalkyl-S(O)$_2$NH$_2$, and triazolyl;

$R^{16}$ is selected from the group consisting of ($C_1$-$C_8$)alkyl, ($C_3$-$C_8$)cycloalkyl, ($C_1$-$C_8$)alkyl-O—($C_1$-$C_8$)alkyl, ($C_1$-$C_8$)alkyl($C_3$-$C_8$)cycloalkyl, ($C_1$-$C_8$)alkylphenyl, ($C_2$-$C_8$)alkenyl, ($C_2$-$C_8$)alkynyl, ($C_1$-$C_8$)haloalkyl, ($C_1$-$C_8$)alkyl-S—($C_1$-$C_8$)alkyl, ($C_1$-$C_8$)alkyl-S(O)—($C_1$-$C_8$)alkyl, ($C_1$-$C_8$)alkyl-S(O)$_2$—($C_1$-$C_8$)alkyl, O- phenyl, O—($C_2$-$C_8$)alkenyl, O—($C_1$-$C_8$)alkyl($C_3$-$C_8$)cycloalkyl, O—($C_1$-$C_8$)alkylphenyl, ($C_1$-$C_8$)alkyl-O—($C_1$-$C_8$)alkyl($C_3$-$C_8$)cycloalkyl, ($C_1$-$C_8$)alkyl-O—($C_1$-$C_8$)haloalkyl, ($C_1$-$C_8$)alkyl-C(=O)NH—($C_1$-$C_8$)haloalkyl, ($C_1$-$C_8$)alkyl-NHC(O)—($C_1$-$C_8$)alkyl, ($C_1$-$C_8$)alkyl-S—($C_1$-$C_8$)haloalkyl, ($C_1$-$C_8$)alkyl-S(O)—($C_1$-$C_8$)haloalkyl, ($C_1$-$C_8$)alkyl-S(O)$_2$—($C_1$-$C_8$)haloalkyl, ($C_1$-$C_8$)alkyl-S(O)$_2$—NH$_2$, and a heterocycle, wherein each alkyl, alkenyl, alkynyl, alkyl-cycloalkyl, haloalkyl, and phenyl, may be optionally substituted with one or more substituents selected from the group consisting of F, Cl, Br, I, CN, OH, NH$_2$, NO$_2$, ($C_1$-$C_8$)alkyl, ($C_2$-$C_8$)alkenyl, ($C_2$-$C_8$)alkynyl, ($C_1$-$C_8$)alkoxy, ($C_1$-$C_8$)haloalkyl, N(($C_1$-$C_8$)alkyl)$_2$, C(O)O($C_1$-$C_8$)alkyl, benzothioenyl, oxoimidazolidinyl, furanyl, pyrazolyl, pyridinyl, thiazolyl, and triazolyl, and wherein the heterocycle is selected from the group consisting of, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, and wherein each ($C_3$-$C_8$)cycloalkyl and heterocycle may be optionally substituted with one or more substituents selected from the group consisting of H, F, Cl, Br, I, CN, NH$_2$, NO$_2$, oxo, ($C_1$-$C_4$)alkyl, ($C_2$-$C_8$)alkenyl, ($C_2$-$C_8$)alkynyl, ($C_1$-$C_4$)haloalkyl, C(=O)O($C_1$-$C_4$)alkyl, (C=O)NH($C_1$-$C_4$)alkyl, (C=O)NH($C_1$-$C_4$)haloalkyl, C(=O)($C_3$-$C_6$)cyclopropyl, C(=O)($C_1$-$C_4$)haloalkyl, C(=O)($C_1$-$C_4$)alkyl($C_1$-$C_4$)alkoxy, and ($C_1$-$C_4$)alkyl-morpholinyl;

$Q^1$ and $Q^2$ are each independently selected from the group consisting of O and S.

In an embodiment of the invention and/or embodiments thereof, the invention is directed to a compound of formula (VII)

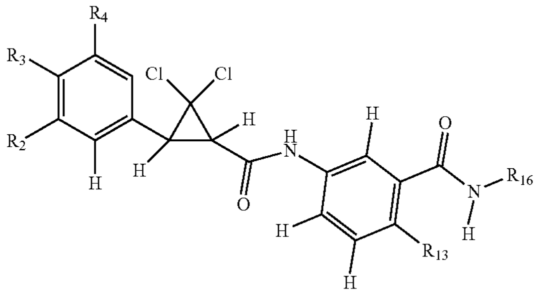

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, NH$_2$, NO$_2$, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_1$-$C_6$)haloalkoxy, ($C_1$-$C_6$)alkyl-S(O)$_2$NH$_2$, and S-(Halo)$_5$;

$R^3$ is selected from the group consisting of H, F, Cl, Br, I, CN, NH$_2$, NO$_2$, ($C_1$-$C_6$)alkyl, ($C_3$-$C_6$)cycloalkyl, ($C_2$-$C_6$)alkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_1$-$C_6$)haloalkoxy, ($C_1$-$C_6$)alkyl-S(O)$_2$NH$_2$, and S-(Halo)$_5$;

$R^4$ is selected from the group consisting of H, F, Cl, Br, I, CN, NH$_2$, NO$_2$, ($C_1$-$C_6$)alkyl, ($C_3$-$C_6$)cycloalkyl, ($C_2$-$C_6$)alkenyl, ($C_3$-$C_6$)cycloalkenyl, ($C_2$-$C_6$)alkynyl, ($C_1$-$C_6$)alkoxy, ($C_1$-$C_6$)haloalkyl, ($C_3$-$C_6$)halocycloalkyl, ($C_2$-$C_6$)haloalkenyl, ($C_3$-$C_6$)halocycloalkenyl, ($C_1$-$C_6$)haloalkoxy, ($C_1$-$C_6$)alkyl-S(O)$_2$NH$_2$, and S-(Halo)$_5$;

$R^5$ is selected from the group consisting of H, F, Cl, Br, I, CN, NH$_2$, NO$_2$, ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_2$-$C_6$)haloalkenyl, and ($C_1$-$C_6$)haloalkoxy;

$R^6$ and $R^9$ are each selected from the group consisting of H, CH$_3$ and CH$_2$CH$_3$;

$R^7$ and $R^8$ are each selected from the group consisting of Cl and Br;

$R^{10}$ is selected from the group consisting of H, ($C_1$-$C_6$)alkyl, ($C_2$-$C_6$)alkenyl, and ($C_1$-$C_6$)haloalkyl;

$R^{13}$ is selected from the group consisting of H, F, Cl, Br, I, CN, $NH_2$, $NO_2$, CHO, ($C_1$-$C_6$)alkyl, ($C_2$-$C_6$)alkenyl, ($C_1$-$C_6$)alkoxy, ($C_1$-$C_6$)haloalkyl, ($C_2$-$C_6$)haloalkenyl, and ($C_1$-$C_6$)haloalkoxy;

$R^{16}$ is selected from the group consisting of ($C_1$-$C_8$)alkyl, ($C_3$-$C_8$)cycloalkyl, ($C_1$-$C_8$)alkyl-O—($C_1$-$C_8$)alkyl, ($C_1$-$C_8$)alkyl($C_3$-$C_8$)cycloalkyl, ($C_2$-$C_8$)alkenyl, ($C_2$-$C_8$)alkynyl, ($C_1$-$C_8$)haloalkyl, ($C_1$-$C_8$)alkyl- S—($C_1$-$C_8$)alkyl, ($C_1$-$C_8$)alkyl-S(O)—($C_1$-$C_8$)alkyl, ($C_1$-$C_8$)alkyl-S(O)$_2$—($C_1$-$C_8$)alkyl, ($C_1$-$C_8$)alkyl-O—($C_1$- $C_8$)haloalkyl, ($C_1$-$C_8$)alkyl-S—($C_1$-$C_8$)haloalkyl, ($C_1$-$C_8$)alkyl-S(O)—($C_1$-$C_8$)haloalkyl, ($C_1$-$C_8$)alkyl-S(O)$_2$—($C_1$-$C_8$)haloalkyl, ($C_1$-$C_8$)alkyl-S(O)$_2$—$NH_2$, and heterocycle, wherein each alkyl, alkenyl, alkynyl, alkyl-cycloalkyl, and haloalkyl in $R^{16}$, may be optionally substituted with one or more substituents selected from the group consisting of F, Cl, Br, I, CN, OH, $NH_2$, $NO_2$, ($C_1$-$C_8$)alkyl, ($C_2$-$C_8$)alkenyl, ($C_2$-$C_8$)alkynyl, ($C_1$-$C_8$)alkoxy, ($C_1$-$C_8$)haloalkyl, C(O)O($C_1$-$C_8$)alkyl, oxoimidazolidinyl, furanyl, and pyrazolyl, wherein each ($C_3$-$C_8$)cycloalkyl in $R^{16}$, may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, C(═O)O($C_1$-$C_4$)alkyl, (C═O)NH($C_1$-$C_4$)alkyl, (C═O)NH($C_1$-$C_4$)haloalkyl, C(═O)($C_3$-$C_6$)cyclopropyl, C(═O)($C_1$-$C_4$)haloalkyl, C(═O)($C_1$-$C_4$)alkyl($C_1$-$C_4$)alkoxy, and ($C_1$-$C_4$)alkyl-morpholinyl, wherein the heterocycle in $R^{16}$ is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide, wherein, each heterocycle in $R^{16}$ may be optionally substituted with one or more substituents selected from the group consisting of H, F, Cl, Br, I, CN, oxo, ($C_1$-$C_4$)alkyl, ($C_2$-$C_8$)alkenyl, ($C_2$-$C_8$)alkynyl, ($C_1$-$C_4$)haloalkyl, (C═O)NH($C_1$-$C_4$)alkyl, (C═O)NH($C_1$-$C_4$)haloalkyl, and C(═O)($C_1$-$C_4$)alkyl($C_1$-$C_4$)alkoxy;

$Q^1$ and $Q^2$ are each independently selected from the group consisting of O and S.

In an embodiment of the invention and/or embodiments thereof, the invention is directed to a compound of formula (VII)

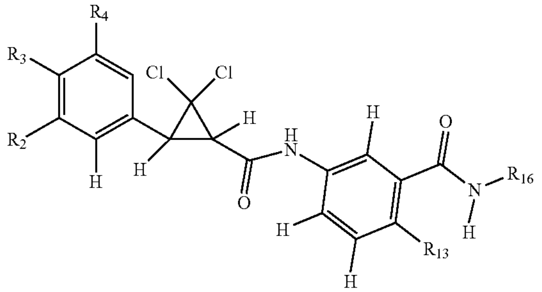

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, $NO_2$, ($C_1$-$C_6$)alkyl, ($C_2$-$C_6$)alkenyl, ($C_1$-$C_6$)alkoxy, and ($C_1$-$C_6$)haloalkyl;

$R^3$ is selected from the group consisting of H, F, Cl, Br, I, CN, $NH_2$, $NO_2$, ($C_1$-$C_6$)alkyl, ($C_1$-$C_6$)alkoxy, ($C_1$-$C_6$)haloalkyl, and ($C_1$-$C_6$)haloalkoxy;

$R^4$ is selected from the group consisting of H, F, Cl, Br, I, CN, $NH_2$, ($C_1$-$C_6$)alkyl, ($C_1$-$C_6$)alkoxy, ($C_1$-$C_6$)haloalkyl, and ($C_1$-$C_6$)haloalkoxy;

$R^5$ is selected from the group consisting of H, F, Cl, Br, $NH_2$, ($C_1$-$C_6$)alkyl, ($C_1$-$C_6$)alkoxy, ($C_1$-$C_6$)haloalkyl, and ($C_1$-$C_6$)haloalkoxy;

$R^6$ and $R^9$ are each selected from the group consisting of H, and $CH_3$;

$R^7$ and $R^8$ are each selected from the group consisting of Cl and Br;

$R^{10}$ is selected from the group consisting of H, and $CH_3$; preferably $R^{10}$ is H;

$R^{13}$ is selected from the group consisting of H, F, Cl, Br, $CH_3$, $OCH_3$, and $CF_3$;

$R^{16}$ is selected from the group consisting of ($C_1$-$C_8$)alkyl, ($C_3$-$C_8$)cycloalkyl, ($C_1$-$C_8$)alkyl($C_3$-$C_8$)cycloalkyl, ($C_2$-$C_8$)alkenyl, ($C_2$-$C_8$)alkynyl, ($C_1$-$C_8$)haloalkyl, ($C_1$-$C_8$)alkyl-S—($C_1$-$C_8$)alkyl, ($C_1$-$C_8$)alkyl-S(O)—($C_1$-$C_8$)alkyl, ($C_1$-$C_8$)alkyl-S(O)$_2$—($C_1$-$C_8$)alkyl, and ($C_1$-$C_8$)alkyl-O—($C_1$-$C_8$)haloalkyl, wherein each alkyl, cycloalkyl, alkenyl, alkynyl, and haloalkyl, may be optionally substituted with one or more substituents selected from the group consisting of F, Cl, Br, ($C_1$-$C_8$)alkyl, ($C_2$-$C_8$)alkenyl, ($C_2$-$C_8$)alkynyl, ($C_1$-$C_8$)alkoxy, C(O)O($C_1$-$C_8$)alkyl, and oxoimidazolidinyl, wherein in $R^{16}$ the ($C_3$-$C_8$)cycloalkyl, may be optionally substituted with one or more substituents selected from the group consisting of H, F, Cl, Br, I, CN, $NH_2$, $NO_2$, oxo, ($C_1$-$C_4$)alkyl, ($C_2$-$C_8$)alkenyl, ($C_2$-$C_8$)alkynyl, ($C_1$-$C_4$)haloalkyl, (C═O)NH($C_1$-$C_4$)alkyl, and (C═O)NH($C_1$-$C_4$)haloalkyl;

$Q^1$ and $Q^2$ are O.

In an embodiment of the invention and/or embodiments thereof, the invention is directed to a compound of formula (VII)

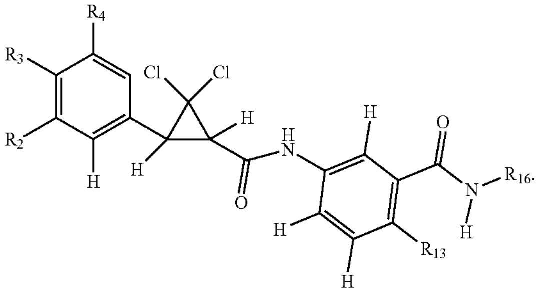

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, Br, I, CN, $NH_2$, ($C_1$-$C_6$)alkyl, ($C_1$-$C_6$)alkoxy, and ($C_1$-$C_6$)haloalkyl;

$R^3$ is selected from the group consisting of H, F, Cl, Br, I, CN, $NH_2$, $(C_1-C_6)$alkyl, and $(C_1-C_6)$haloalkyl;

$R^4$ is selected from the group consisting of H, F, Cl, Br, I, $(C_1-C_6)$alkyl, and $(C_1-C_6)$haloalkyl;

$R^5$ is selected from the group consisting of H, F, Cl, Br, $(C_1-C_6)$alkyl, and $(C_1-C_6)$haloalkyl;

$R^6$ and $R^9$ are each H;

$R^7$ and $R^8$ are each Cl;

$R^{10}$ is H;

$R^{13}$ is selected from the group consisting of H, Cl, F, $CH_3$, and $OCH_3$;

$R^{16}$ is selected from the group consisting of $(C_1-C_8)$alkyl, $(C_3-C_8)$cycloalkyl, $(C_2-C_8)$alkenyl, $(C_2-C_8)$alkynyl, $(C_1-C_8)$haloalkyl, and $(C_1-C_8)$alkyl-O—$(C_1-C_8)$haloalkyl, wherein each alkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, $(C_1-C_8)$alkoxy, $C(O)O(C_1-C_8)$alkyl, and oxoimidazolidinyl, wherein the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, $(C_2-C_8)$alkynyl, $(C_1-C_4)$haloalkyl, and $(C{=}O)NH(C_1-C_4)$alkyl;

$Q^1$ and $Q^2$ are O.

In an embodiment of the invention and/or embodiments thereof, the invention is directed to a compound of formula (VII)

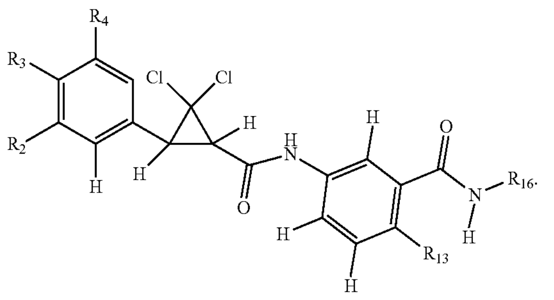

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, CN, $CH_3$, $CHF_2$ and $CF_3$, preferably $R^2$ is selected from the group consisting of H, F, and Cl, preferably $R^2$ is F or Cl;

$R^3$ is selected from the group consisting of H, F, Cl, Br, $CH_3$, $CHF_2$ and $CF_3$, preferably $R^3$ is selected from the group consisting of H, F, Cl, Br and $CHF_2$;

$R^4$ is selected from the group consisting of H, F, Cl, Br, $CH_3$, $CHF_2$ and $CF_3$, preferably $R^4$ is selected from the group consisting of H, F, and Cl, more preferably $R^4$ is F or Cl;

$R^5$ is selected from the group consisting of H, F, and Cl, preferably $R^5$ is H;

$R^6$ and $R^9$ are each H;

$R^7$ and $R^8$ are each Cl;

$R^{10}$ is H;

$R^{13}$ is Cl or F;

$R^{16}$ is selected from the group consisting of $(C_1-C_8)$alkyl, $(C_3-C_8)$cycloalkyl, $(C_2-C_8)$alkenyl, $(C_2-C_8)$alkynyl, and $(C_1-C_8)$haloalkyl, wherein each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, and $(C_1-C_8)$alkoxy, wherein the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, and $(C_2-C_8)$alkynyl;

$Q^1$ and $Q^2$ are O.

In an embodiment of the invention and/or embodiments thereof, the invention is directed to a compound of formula (VII)

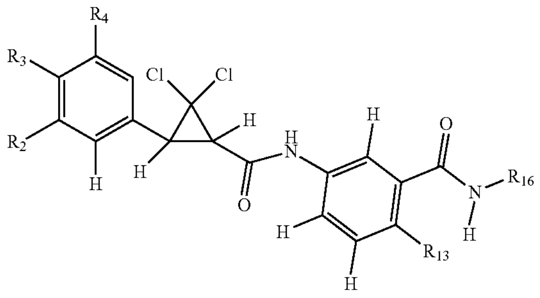

and N-oxides, veterinary acceptable acid addition salts, salt derivatives, solvates, ester derivatives, crystal polymorphs, isotopes, stereoisomers, and tautomers, and use thereof in a method to control a parasite infestation in fish wherein $R^2$ is selected from the group consisting of H, F, Cl, CN, $CH_3$, $CHF_2$ and $CF_3$, preferably $R^2$ is selected from the group consisting of H, F, and Cl, preferably $R^2$ is F or Cl;

$R^3$ is selected from the group consisting of H, F, Cl, Br, $CH_3$, $CHF_2$ and $CF_3$, preferably $R^3$ is selected from the group consisting of H, F, Cl, Br and $CHF_2$;

$R^4$ is selected from the group consisting of H, F, Cl, Br, $CH_3$, $CHF_2$ and $CF_3$, preferably $R^4$ is selected from the group consisting of H, F, and Cl, more preferably $R^4$ is F or Cl;

$R^5$ is selected from the group consisting of H, F, and Cl, preferably $R^5$ is H;

$R^6$ and $R^9$ are each H;

$R^7$ and $R^8$ are each Cl;

$R^{10}$ is H;

$R^{13}$ is Cl or F;

$R^{16}$ is selected from the group consisting of $(C_1-C_8)$alkyl, $(C_3-C_8)$cycloalkyl, $(C_2-C_8)$alkenyl, $(C_2-C_8)$alkynyl, and $(C_1-C_8)$haloalkyl, wherein each alkyl, cycloalkyl, alkenyl, alkynyl, and haloalkyl, may be optionally substituted with one or more substituents selected from the group consisting of F, Cl, Br, $(C_1-C_8)$alkyl, $(C_2-C_8)$alkenyl, $(C_2-C_8)$alkynyl, and $(C_1-C_8)$alkoxy, wherein the $(C_3-C_8)$cycloalkyl, may be optionally substituted with one or more substituents selected from the group consisting of H, F, Cl, CN, oxo, $(C_1-C_4)$alkyl, $(C_2-C_8)$alkenyl, and $(C_2-C_8)$alkynyl;

$Q^1$ and $Q^2$ are O.

Suitable compounds according to the invention and embodiments thereof are the compounds as indicated the table below:
1541
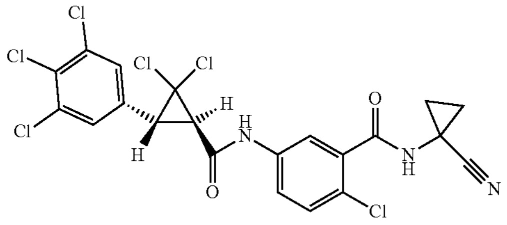
1584
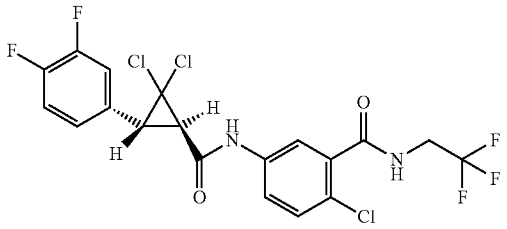
1585
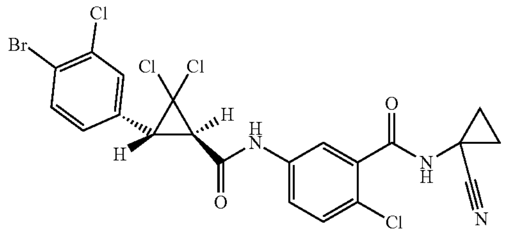
1587
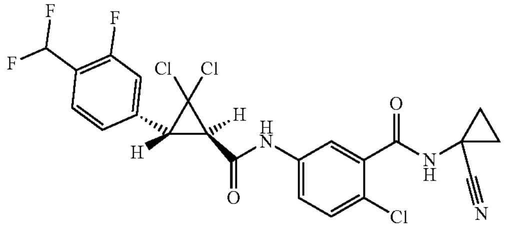
1590
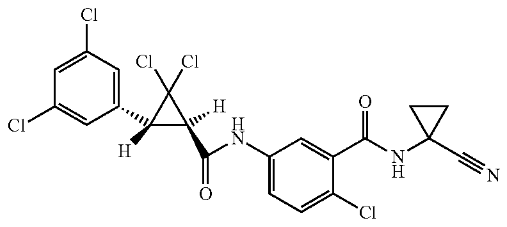
1592
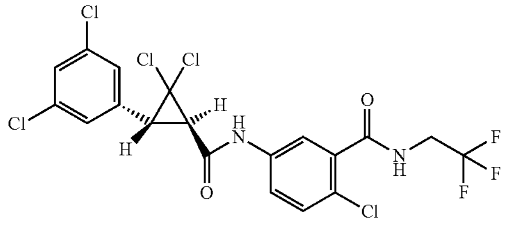
-continued
1593
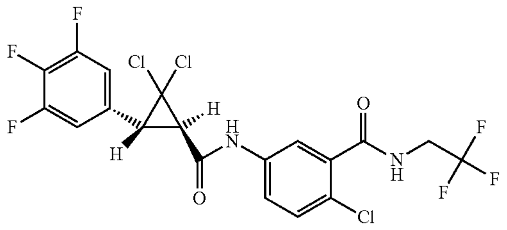
1594
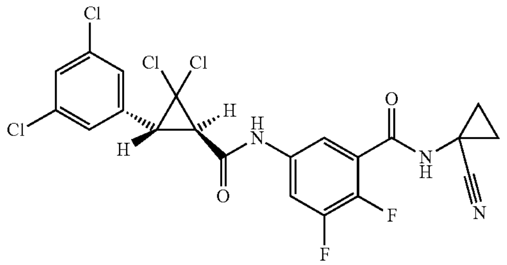
1601
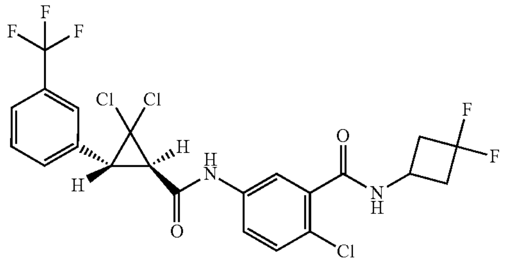 [SMILES: O=C(NC1CC(F)(F)C1)c1cc(NC(=O)[C@H]2[C@H](c3cccc(C(F)(F)F)c3)C2(Cl)Cl)ccc1Cl]
1605
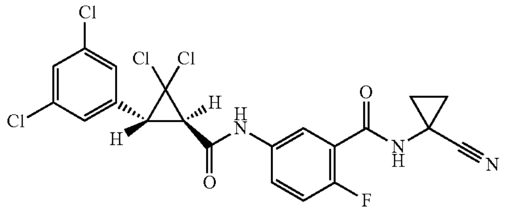 [SMILES: N#CC1(NC(=O)c2cc(NC(=O)[C@H]3[C@H](c4cc(Cl)cc(Cl)c4)C3(Cl)Cl)ccc2F)CC1]
1606
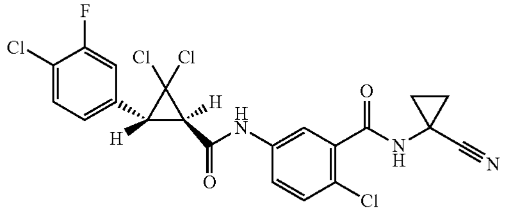 [SMILES: N#CC1(NC(=O)c2cc(NC(=O)[C@H]3[C@H](c4ccc(Cl)c(F)c4)C3(Cl)Cl)ccc2Cl)CC1]
1608
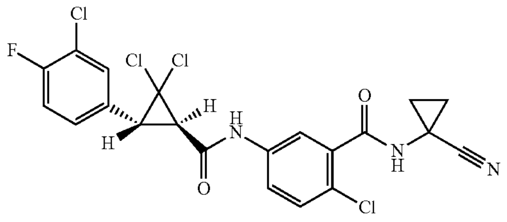 [SMILES: N#CC1(NC(=O)c2cc(NC(=O)[C@H]3[C@H](c4ccc(F)c(Cl)c4)C3(Cl)Cl)ccc2Cl)CC1]

-continued
1609
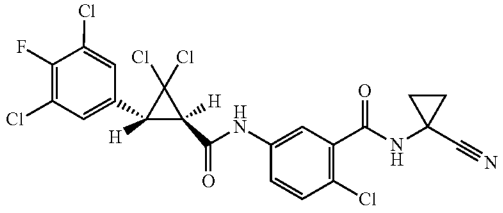 [SMILES: N#CC1(NC(=O)c2cc(NC(=O)[C@H]3[C@H](c4cc(Cl)c(F)c(Cl)c4)C3(Cl)Cl)ccc2Cl)CC1]
1617
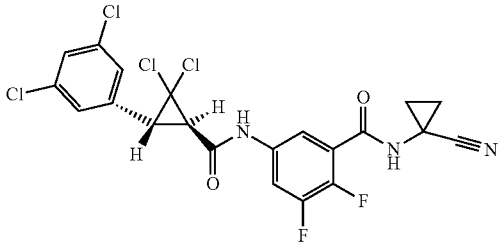
1618
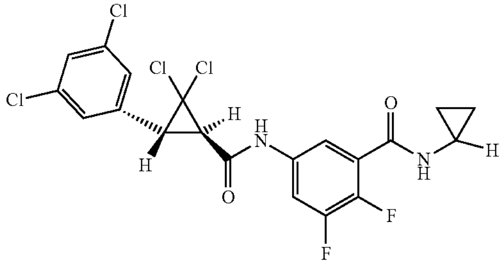
1619
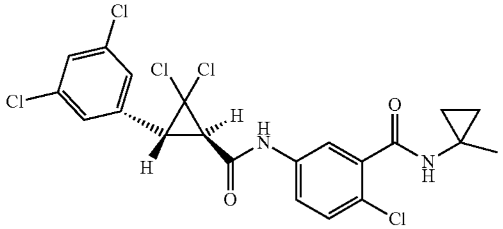
1620
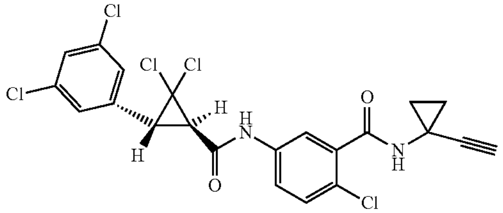
1621
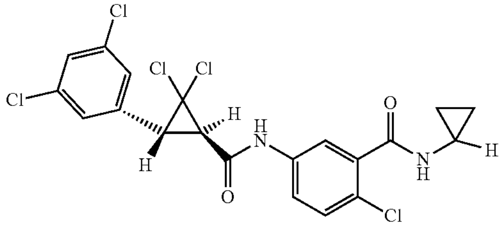
-continued
1622
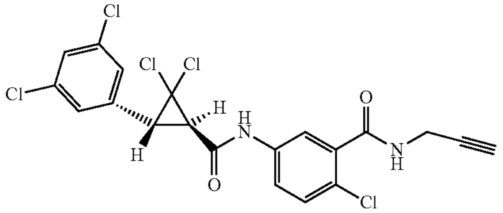
1623
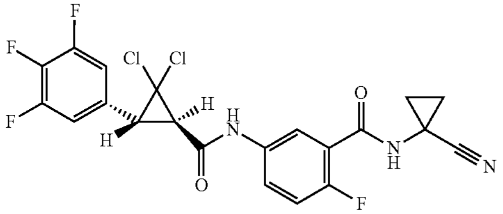
1624
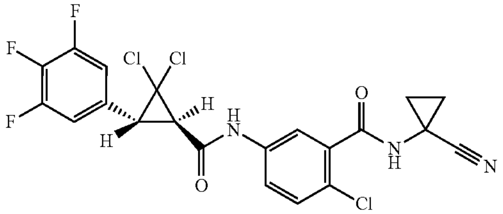 [SMILES: N#CC1(NC(=O)c2cc(NC(=O)[C@H]3[C@H](c4cc(F)c(F)c(F)c4)C3(Cl)Cl)ccc2Cl)CC1]
1625
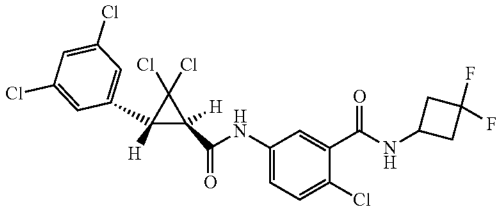
1626
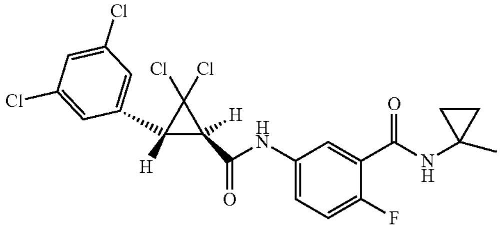
1628
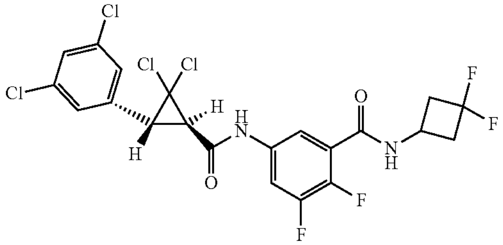
1630
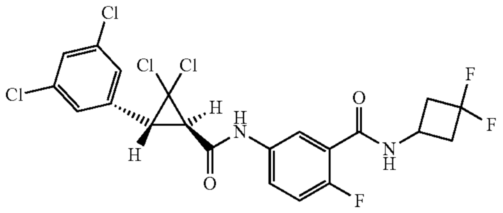

-continued
1632
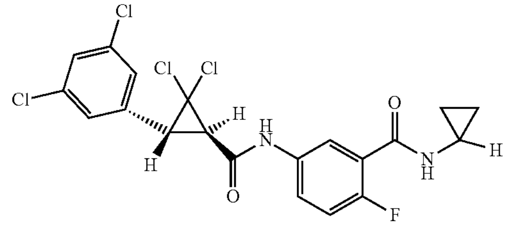
1633
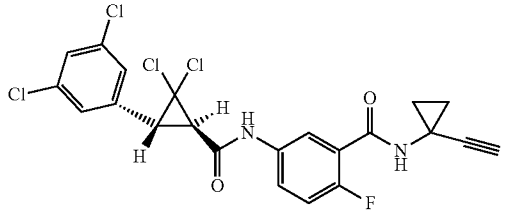
Suitable compounds with advantageous properties are listed below:
1536
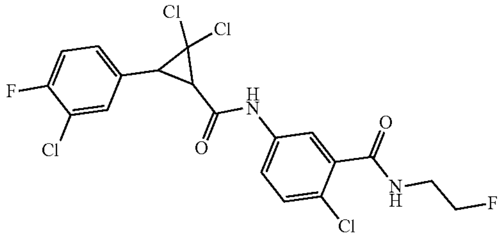 [SMILES: O=C(NCCF)c1cc(NC(=O)C2C(c3ccc(F)c(Cl)c3)C2(Cl)Cl)ccc1Cl]
1538
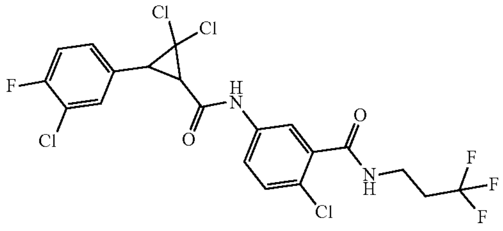 [SMILES: O=C(NCCC(F)(F)F)c1cc(NC(=O)C2C(c3ccc(F)c(Cl)c3)C2(Cl)Cl)ccc1Cl]
1551
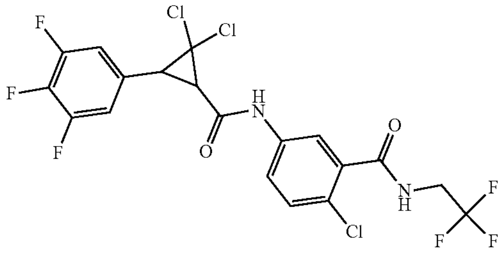 [SMILES: O=C(NCC(F)(F)F)c1cc(NC(=O)C2C(c3cc(F)c(F)c(F)c3)C2(Cl)Cl)ccc1Cl]
1558
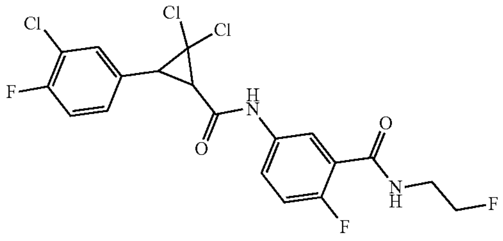 [SMILES: O=C(NCCF)c1cc(NC(=O)C2C(c3ccc(F)c(Cl)c3)C2(Cl)Cl)ccc1F]
-continued
1559
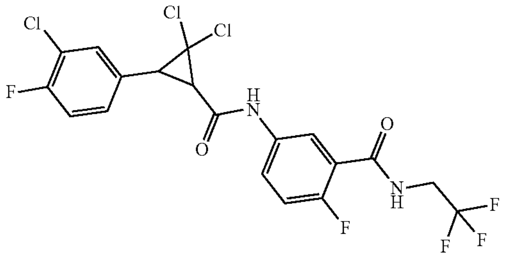 [SMILES: O=C(NCC(F)(F)F)c1cc(NC(=O)C2C(c3ccc(F)c(Cl)c3)C2(Cl)Cl)ccc1F]
1563
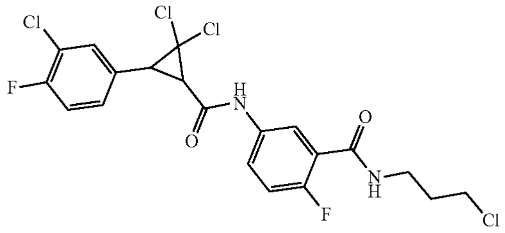 [SMILES: O=C(NCCCCl)c1cc(NC(=O)C2C(c3ccc(F)c(Cl)c3)C2(Cl)Cl)ccc1F]
1565
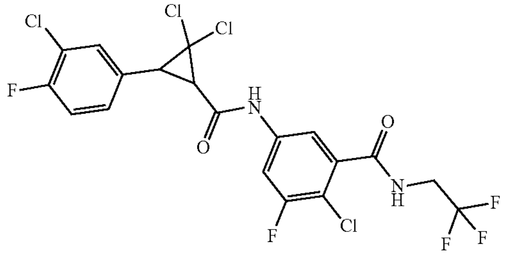 [SMILES: O=C(NCC(F)(F)F)c1cc(NC(=O)C2C(c3ccc(F)c(Cl)c3)C2(Cl)Cl)cc(F)c1Cl]
1593
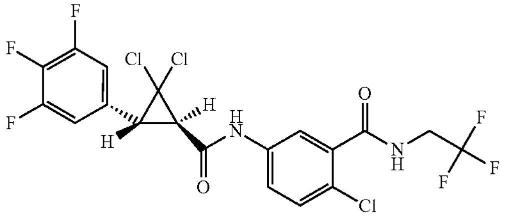
1605
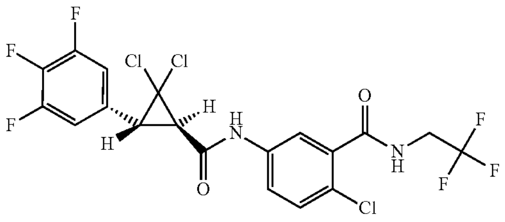
1608
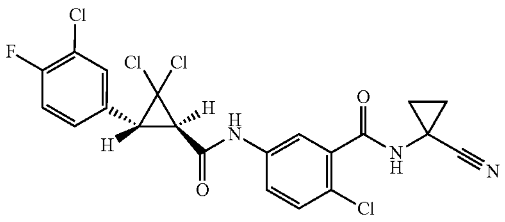 [SMILES: N#CC1(NC(=O)c2cc(NC(=O)[C@H]3[C@H](c4ccc(F)c(Cl)c4)C3(Cl)Cl)ccc2Cl)CC1]

-continued

1632

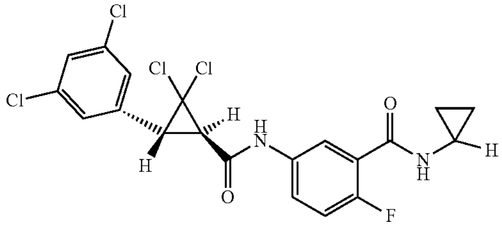

Salts, Solvates, N-Oxides and Prodrugs

A salt of the compounds of the Formula (I), or another compound may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e., to an animal) for a therapeutic benefit, the salt is pharmaceutically acceptable.

Salts may also be of advantage in the synthesis of the compounds according to this invention and/or embodiments thereof. For instance, certain intermediates may advantageously be used in form of their salts in the preparation process of the compounds according to this invention and/or embodiments thereof.

In general, an acid addition salt can be prepared by reacting a free base compound with an approximately stoichiometric amount of an inorganic or organic acid. Non-limiting Examples of often suitable inorganic acids for making (pharmaceutically acceptable) salts include hydrochloric, hydrobromic, hydroiodic, nitric, carbonic, sulfuric, and phosphoric acid. Non-limiting Examples of often suitable organic acids for making (pharmaceutically acceptable) salts generally include, for example, aliphatic, cycloaliphatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N, N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of Formula (I) may be formulated into stable complexes with a solvent, such that the complex remains intact after the non-complexed solvent is removed. These complexes are often referred to as "solvates." However, it is particularly desirable to form stable hydrates with water as the solvent.

A solvate of a compound of the Formula (I), or another compound may be formed by aggregation of said compound of the Formula (I) with solvent molecules such as water, alcohols, for example ethanol, aromatic solvents such as toluene, ethers, halogenated organic solvents such as dichloromethane, preferably in a definite proportion by weight.

Compounds of Formula (I) containing an acid functionality may be made into ester derivatives. These ester derivatives can then be applied in the same manner as the compounds disclosed in this document are applied.

Compounds of Formula (I) may be made as various crystal polymorphs. Polymorphism is important in the development of veterinary products since different crystal polymorphs or structures of the same molecule can have vastly different physical properties and biological performances.

An N-oxide of a compound of the Formula (I), or another compound may be formed by oxidation of an N-atom in an amine or N-heterocycle such as pyridine and pyrimidine by oxidation agents such as hydrogen peroxide, peracids or inorganic oxidation agents such as potassium peroxymonosulfate (oxone).

This invention also encompasses prodrug derivatives of the compounds of Formula (I). The term prodrug refers to compounds that are transformed in vivo to yield the parent compound of Formula (I). In vivo means that in the case of, for example, treatment of a parasitic infestation this transformation can occur in the host organism and/or the parasite. Various forms of prodrugs are well known in the art. For example, if the group of Formula (A) represents a pyridine, it is possible to form pyridinium salts such as, for example, acyloxyalkylpyridinium salts, which can offer advantages in terms of higher solubility for parenteral dosage forms, which are described in S. K. Davidsen et al., *J. of Med. Chem.* 37 4423-4429 (1994).

Compounds of Formula (I) may be made with different isotopes. Of particular importance are molecules having $^2H$ (also known as deuterium) or $^3H$ (also known as tritium) in place of 1H. Molecules of Formula One may be made with different radionuclides. Of particular importance are molecules having $^{14}C$ (also known as radiocarbon). Molecules of Formula (I) having deuterium, tritium, or $^{14}C$ may be used in biological studies allowing tracing in chemical and physiological processes and half-life studies, as well as MoA studies.

Isomers

The compounds of Formula (I) may exist in different geometric or optical isomeric or different tautomeric forms. One or more centers of chirality may be present in which case compounds of Formula (I) may be present as pure enantiomers, mixtures of enantiomers, pure diastereomers or mixtures of diastereomers. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. There may be double bonds present in the molecule, in which case compounds of Formula (I) may exist as single geometric isomers (cis or trans, E or Z) or mixtures of geometric isomers (cis and trans, E and Z). Centers of tautomerisation may be present. This disclosure covers all such isomers, tautomers, and mixtures thereof, in all proportions.

In some embodiments, such compounds may have two or more isomers, such as optical isomers or conformational isomers. For example, the compounds can have a (E) or (Z) configuration at the $—CXR^3═CR^1R^2$ double bond, such as in alkenyl or alkynyl substituents of $R^6$ or alkenyl or alkynyl substituents of ring structures of $R^{16}$. In some preferred embodiments, such compound has the (E) configuration, in other embodiments, the compound has the (Z) configuration. In a preferred embodiment the compounds have (E) configuration. For instance, the compounds of Formula (II) and the compounds of tables A, C and D below exhibit (E) configuration.

Unless otherwise stated, a compound structure that does not indicate a particular conformation is intended to encompass all the possible conformational isomers of the compound, as well as comprising fewer than all the possible conformational isomers. Compounds with two chiral centers have four isomers: the RR-, SS-, RS-, and SR-isomers. Such compounds may exist in a number of forms i.e., in the pure RR or SS or RS or SR isomeric forms, or as mixtures, hereinafter called "enantiomeric pairs" of either RR/SS or RS/SR.

The cyclopropyl amide compounds can also exist as racemic mixtures of all four isomers (RR+SS+RS+SR) or in the form of racemic mixtures of the enantiomeric pairs (RR/SS) or (RS/SR). The isomers (RR) and (SS) are mirror images of each other and are therefore enantiomers, which have the same chemical properties and melting points. (RS) and (SR) is similarly an enantiomeric pair. The mirror images of (RR) and (SS) are not, however, super imposable on (RS) and (SR). This relationship is called diastereomerism, and (RR) is a diastereomer to (RS).

Although structurally identical, isomers can have different effects in biological systems: one isomer may have specific therapeutic activity while another isomer may have no therapeutic activity or may have entirely different forms of biological activity.

In the compounds of the invention, the cyclopropane contains 2 chiral centers, one bonded to the phenyl and the other bonded to the carboxamide group.

It has now surprisingly been found that parameters, such as for example efficacy can be greatly improved by administering pure or substantially pure RR-isomer of the compounds according to the invention and embodiments as described herein, a pharmaceutically acceptable salt, thereof, while side effects can be substantially avoided. Thus, the applicant has found that by administering a therapeutically effective amount of the pure or substantially pure RR-isomer of the compounds according to the invention and embodiments as described herein, a pharmaceutically acceptable salt, thereof.

Terms like "pure RR-cyclopropyl amide compounds" "pure RR-isomer of cyclopropyl amide compounds" and the like, refer to cyclopropyl amide compounds having an optical purity of RR-cyclopropyl amide compounds of Formula (I), that is 98% by weight or better, which means the RR-isomer is present at a concentration of 98% by weight or more, while the total concentration (i.e. the sum) of the corresponding RS-, SR- and SS-isomers is 2% by weight or less, based on the total amount of the cyclopropyl amide compounds present.

The terms "substantially pure RR-cyclopropyl amide compounds" "substantially pure RR-isomer of cyclopropyl amide compounds" and the like, refer to an optical purity of RR-*cyclopropyl amide compounds that is 80% by weight or better which means a concentration of 80% weight or more of RR-cyclopropyl amide compounds and 20% by weight or less of the sum of the corresponding RS-, SR- and SS-isomers, based on the total amount of cyclopropyl amide compounds present. In a more preferred embodiment, a "substantially pure RR-cyclopropyl amide compounds contains 90% by weight or more of RR-cyclopropyl amide compounds and 10% or less of the sum of the RS and SR and SS-isomers of cyclopropyl amide compounds.

In a suitable embodiment the compounds of Formula (I), the carboxamido, and the phenyl, which are bonded to the cyclopropane, are in the R,R configuration. This embodiment may be used in combination with any of the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$.

In embodiment of the invention and/or embodiments thereof, the parasite infestation is a sea lice infestation.

In embodiment of the invention and/or embodiments thereof, the parasite is at least one of *Lepeophtheirus salmonis, Caligus celmensi, Caligus curtus, Caligus dussumieri, Caligus elongates, Caligus longicaudatus, Caligus rogercresseyi* or *Caligus stromii.*

In embodiment of the invention and/or embodiments thereof, the parasite infestation is with copepodites, pre-adult, or adult sea lice or a mixed infestation with various stages.

In embodiment of the invention and/or embodiments thereof, an existing parasite infestation of a fish population is treated.

In embodiment of the invention and/or embodiments thereof, the parasite is an adult sea lice.

In embodiment of the invention and/or embodiments thereof, the parasite is a juvenile sea lice.

In embodiment of the invention and/or embodiments thereof, the rate of infestation of the fish population in the aquaculture facility is between 0.5 and 3 parasites on average per fish, preferably wherein the parasite is an adult female sea louse.

In embodiment of the invention and/or embodiments thereof, the method comprises administering to fish an effective amount of a compound of Formula (I) as defined in any embodiment described herein to protects fish from infestation and/or re-infestation with parasites, preferably wherein the parasite is a sea lice in a pre-adult or adult stage.

In embodiment of the invention and/or embodiments thereof, the method comprises administering to fish an effective amount of a compound of Formula (I) as defined in any embodiment described herein, wherein the time between administrations is 2-8 weeks, preferably 3-6 weeks and more preferably about 4 weeks.

In embodiment of the invention and/or embodiments thereof, the parasite is resistant against macrocyclic lactone, organophosphates and or pyrethroid antiparasitic agents, preferably wherein the parasite is sea lice.

In embodiment of the invention and/or embodiments thereof, the method comprises administering to fish the compound of Formula (I) as defined in any embodiment described herein together with a physiologically active agent.

In embodiment of the invention and/or embodiments thereof, the method comprises administering to fish the compound of Formula (I) as defined in any embodiment described herein together with an antigen, optionally the compound and antigen are administered together with an adjuvant.

In embodiment of the invention and/or embodiments thereof, the method comprises administering to fish the compound of Formula (I) as defined in any embodiment described herein together with an additional antiparasitic agent.

In embodiment of the invention and/or embodiments thereof, the method comprises administering to fish the compound of Formula (i) as defined in any embodiment described herein by oral administration, or by topical administration, or by bath treatment or by intraperitoneal or intramuscular injection.

In embodiment of the invention and/or embodiments thereof, the method comprises administering to fish the compound of Formula (I) as defined in any embodiment herein by oral administration, wherein the oral administration comprises administering a medicated fish feed comprising the compound and fish feed.

In embodiment of the invention and/or embodiments thereof, the medicated fish feed is administered daily for a period of 3 to 7 days.

In embodiment of the invention and/or embodiments thereof, the method comprises administering the compound of Formula (I) as defined in any embodiment described herein to the fish by bath treatment, wherein the bath treatment comprises immersion of fish in water containing a therapeutically effective amount of a compound.

The present invention is also related to a composition comprising a compound of Formula (I) as defined in any embodiment described herein and a veterinarily acceptable formulation auxiliaries.

In embodiment of the invention and/or embodiments thereof, the composition comprises a solvent, and optionally, a solubilizer.

In embodiment of the invention and/or embodiments thereof, the composition is in the form of a stock solution to be used to form a medicated water comprising an effective amount of the compound.

In embodiment of the invention and/or embodiments thereof, the effective amount of the compound in the medicated water is about 2 ppb to about 500 ppb.

In embodiment of the invention and/or embodiments thereof, the method comprises administration of the compound to the fish by bath immersion of the fish.

In embodiment of the invention and/or embodiments thereof, the method comprises administering the composition to fish by oral administration via feed.

Furthermore, the invention is related to a premix comprising a compound of Formula (I) as defined in any embodiment described herein and/or a composition as described herein, wherein the premix further comprises nutrients.

In embodiment of the invention and/or embodiments thereof, the premix comprises nutrients in the form of pellets wherein the pellets are coated with a composition comprising a compound of Formula (I) as defined in any embodiment described herein or coated with a composition as described herein.

In embodiment of the invention and/or embodiments thereof, the premix comprises nutrients in the form of pellets which are mixed with a composition comprising a compound of Formula (I) as defined in any embodiment described herein or a composition as described herein.

In addition, the present invention is related to a medicated fish feed comprising the composition as described herein or a premix as described herein and fish feed.

The medicated fish feed as described herein is suitable for use in a method as described herein.

The invention is also related to a kit comprising the composition as described herein and instructions for administration of the composition to fish to control parasite infestation.

The invention is also related to a kit comprising the premix as described herein and instructions for preparation of medicated a fish feed and instructions for administration of the medicated fish feed to a fish to control parasite infestation.

The invention is also related to a kit comprising the stock solution as described herein and instructions for preparation of medicated water for a bath treatment and instructions for immersion of fish to control parasite infestation.

Definitions

The following definitions are relevant in connection with the embodiments of the present invention.

Definitions

"Parasite(s)," A parasite is an organism that lives on or in another organism (usually referred to as the host), causing harm to the host. as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms which feed through or upon the skin of its host. In the current invention the host animal is a fish.

"Fish" as used herein, unless otherwise indicated, refers to the taxonomic class Chondrichthyes (cartilaginous fishes, e.g., sharks and rays) and Osteichthyes (bony fishes) which live in water, have gills or mucus-covered skin for respiration, fins, and may have scales. This includes food fish, breeding fish and aquarium, pond fish, and farmed fish of all ages occurring in freshwater, sea water (e.g., marine) and brackish water.

Non-limiting examples of food fish include carp, eel, trout, whitefish, salmon, roach, rudd, chub, arctic char, sturgeon, plaice, halibut, turbot, flounder, striped bass, yellowtail, grouper, cod, sole, tuna, red sea bream, sea bass, grey mullet, pompano, gilthread seabream, tilapia, and catfish.

The invention relates more particularly, to marine fish, and more particularly to marine food fish, especially salmon.

Within the scope of this invention the term "salmon" will be understood as comprising all representatives of the family Salmonidae, especially, the following species: *Salmo salar* (Atlantic salmon); *Salmo trutta* (brown or sea trout); *Salmon gairdneri* (rainbow trout); and the Pacific salmon (*Oncorhynchus*): *O. gorbuscha; O. keta; O. nekra; O. kisutch, O. tshawytscha* and *O. mason*; also comprised are artificially propagated species such as *Salvelinus* spp. and *Salmo clarkia.*

Preferred hosts of the present invention are the Atlantic and Pacific salmon and the sea trout.

In another embodiment the host fish is a Mediterranean Sea bass and/or Sea bream. In another embodiment the host fish is freshwater fish such as carp and/or freshwater trout. In another embodiment the fish is tilapia.

Fish population means a group of individual fish that are kept in a confined area such as in sea water tanks, cages, or nets. The cages and nets are moored in sea inlets such that a daily tidal flow of water passes through them to ensure a sufficient supply of oxygen and clean water.

For tanks, there is a continual flow of sea water in and out of the tanks or at least scheduled flushing of fresh sea water to ensure sufficient water quality and oxygen to maintain fish health. In this artificial environment, the fish are fed and, if necessary, provided with medication until they mature sufficiently for marketing as edible fish or are selected for further breeding.

In one embodiment of the present invention, the compound of Formula (I), or a salt, enantiomer, or prodrug thereof, is administered to a fish population at the end of the freshwater stage or at the beginning of the sea water stage in the farming of the fish.

According to another embodiment the treatment is performed whilst the (salmon or sea trout) fish are kept in sea water.

Sea Lice

In accordance with this invention the compounds of Formula (I) are especially suited for use in the control of fish-parasitic crustaceans, such as e.g., sea lice. Therefore, in one embodiment the compounds of Formula (I) are used to control fish-parasitic crustaceans especially a sea lice infestation.

Sea louse is the common name given to a group of fish-parasitic crustaceans, being ectoparasite copepods, which affect fish in salt water. "Sea lice" as used herein, unless otherwise indicated, refers to parasitic crustaceans (copepods) which feed through or upon the mucus, skin and tissue of its host and are within the order Siphonostomatoida.

These include the amilies Caligidae and Lernanthropidae. Two representatives of the Caligidae family cause substantial losses in salmonid fish farming: *Lepeophtheirus* spp. and *Caligus* spp. (C). species within *Lepeophtheirus* spp. (L) include e.g., *Lepeophtheirus salmonis oncorhynchi, Lepeophtheirus salmonis Lernanthropus koyeri* and within *Caligus* spp. include e.g., *Caligus clemensi, Caligus* curtus, *Caligus dussumieri, Caligus elongatus, Caligus longicaudatus, Caligus rogercresseyi* and *Caligus stromii* and *Caligus minimus.*

*L. salmonis* is found only in the Northern hemisphere. *C. rogercresseyi* is the most important species of sea louse in Chile affecting the salmon industry.

One representative of the Lernanthropidae family is of concern mainly in Mediterranean fish farming: *Lernanthropus* spp. Species within *Lernanthropus* spp. include e.g., *Lernanthropus kroyeri, Lernanthropus callinomymicola, Lernanthropus indefinitus, Lernanthropus cynoscicola* and *Lernanthropus gisleri.*

In one embodiment the compound is used to control sea lice infestations, the sea lice are at least one of *Lepeophtheirus salmonis, Caligus clemensi, Caligus* curtus, *Caligus dussumieri, Caligus elongatus, Caligus longicaudatus, Caligus rogercresseyi* or *Caligus stromii, Caligus minimus* or *Lernanthropus kroyeri.*

In another embodiment the compound is used to control fish-parasitic crustacean infestations, the fish-parasitic crustaceans are at least one of *Lepeophtheirus kroyeri* and *Caligus minimus.*

It has been found that the compounds of Formula (I) can control various stages of fish-parasitic crustaceans, especially sea lice.

In one embodiment the compound of Formula (I) is used to control fish-parasitic crustaceans, especially sea lice infestation with copepodides, pre-adult, or adult sea lice or a mixed infestation with various stages.

Fish-parasitic crustaceans, such ascaligid sea lice have both free-swimming (planktonic) and parasitic life stages, all separated by moults.

Eggs hatch into nauplii I, which moult to a second naupliar stage; both naupliar stages are nonfeeding, depending on yolk reserves for energy, and adapted for swimming. The next life cycle stage, the copepodid stage, is the infectious stage and it searches for an appropriate host, likely by chemo- and mechanosensory clues.

Transmission of caligid sea lice occurs during the copepod planktonic stages (larvae). Copepodids once attached to a suitable host feed for a period of time prior to moulting to the chalimus I stage. Sea lice continue their development through up to four chalimus stage by molting. A characteristic feature of all chalimus stages is that they are physically attached to the host by a structure referred to as the frontal filament. Differences in the timing, method of production, and the physical structure of the frontal filament are seen between distinct species of sea lice.

With exception of a brief period during the moult, the preadult and adult stages are mobile on the fish, and in some cases, can move between host fish. Adult females, being larger, occupy relatively flat body surfaces on the posterior ventral and dorsal midlines and the head region.

The naupliar and copepodid stages until they locate a host are nonfeeding and live on endogenous food stores. Once attached to the host, the copepodid stage begins feeding and begins to develop into the first chalimus stage. Copepods and chalimus stages have a developed gastrointestinal tract and feed on host mucus and tissues within range of their attachment (sessile stages). Preadult and adult sea lice, especially gravid females, are aggressive feeders, in some cases feeding on blood in addition to tissue and mucus.

As used herein "juvenile sea lice" are the stages before the individual matures into pre-adult and adult stage and include copepodid, and chalimus parasitic phases of sea lice.

As used herein the term "sessile stages" means juvenile and "mobile" stages—pre-adult and adult stages.

In one embodiment an existing infestation of a fish population with mobile stages such as adult sea lice stages and/or preadult stages is treated. This is especially important because these parasite stages cause the most severe damage when feeding on fish.

Infestation of a fish means that at least one member of a parasite stages is visible on the surface of a fish. In special cases automatic sea lice counting methods can be employed to detect infestation and the extend of sea lice infestation by counting parasites.

In an alternative preferred embodiment, an existing infestation of a fish population with juvenile sea lice (sessile stages) is treated, as determined by sea lice counting methods. Such control of juvenile sea lice infestation is desirable because the control of juvenile stages provides a prolonged effect because it protects fish from development of preadult or adult stages of sea lice on the fish, especially from adult female sea lice.

In another embodiment an existing infestation of a fish population with juvenile sea lice (sessile stages) and adult stages (mobile stages) is treated.

In one embodiment a single administration of a compound of Formula (I) protects a fish population from re-infestation by parasites, especially sea lice for 4 weeks, so that the treatment interval is 4 weeks (i.e. the time between the administration is 4 weeks).

In one embodiment the time between administrations is 2-8 weeks, preferably 3-6 weeks and more preferably about 4 weeks. Re-infestation means that an individual was infested by a certain parasite and later another parasite infestation from the environment or contact with infested fish or equipment was established on the same animal.

In another embodiment the parasites are *Argulus* spp. *Argulus* (carp lice), *Lernaea*, and *Ergasilus*, belonging to the class Crustacea, are considered important ectoparasites on fishes. The parasitic copepods *Argulus* and *Lernaea* attach themselves to the body of the fish, with their body buried into the scale pockets and with paired egg sacs protruding free. *Argulus* spp. in particular attaches itself to the body of the fish by means of suckers and hooks but can also swim freely in water.

Control

As used herein, the term "controlling" refers to reducing the number of parasites, especially fish-parasitic crustaceans, especially sea lice, eliminating parasites, especially fish-parasitic crustaceans, especially sea lice and/or preventing further infestation, especially infestation by preadult and adult stages of fish-parasitic crustaceans, especially sea lice.

"Treatment" refers to prophylactic or responsive treatment, such as the control, elimination, protection against, and/or prevention of the fish parasite (such as sea lice) infestation or condition in a fish or fish population. The terms encompass reducing the mean number of parasites (such as sea lice) infesting each fish in a fish population, or preventing an increase in the mean number of parasites that are currently infesting each fish in a fish population; i.e. treating existing parasite infestation, or additionally or alternatively preventing the onset of an infestation with parasites (such as sea lice), or of symptoms associated with a parasitic infestation, including reducing the severity of a disorder or condition or symptoms associated with the infestation. The terms also encompass preventing the recurrence of a fish parasite infestation or of symptoms associated therewith as well as references to "control" (such as, for example, kill, repel, expel, incapacitate, deter, eliminate, alleviate, minimize, and eradicate).

In most countries, salmon producers are obliged to regularly report their sea lice levels and treatment data. Regional regulations require e.g., weekly samples of at least five fish per net pen from a minimum of six net pens when the water temperature is above 5° C. On all occasions, fish-level sea lice counts are reported for different parasite life stages; chalimus, preadult males and females together with adult males (PAAM), and adult females (AF; both gravid and non-gravid). In Norway, a fish population is treated when more than 0.5 adult female lice on average per fish in the aquaculture facility have been detected. An aquaculture facility is the entity that keeps salmon, sometimes called fish farming site. In Scotland it is a requirement that if there is an average of 3 adult female sea lice per fish found during a weekly count on any fish farming site, this must be reported.

A preferred embodiment the compound of Formula (I) is used to control sea lice infestation when the infestation rate of the fish population in the aquaculture facility is between 0.5 and 3 adult female sea lice on average per fish.

Effective Amount and Administration Route

As used herein, the term "effective amount" refers to the amount or dose of the compound of Formula (I), or a salt thereof, which, upon single or multiple dose administration to the fish or a fish population, provides the desired effect.

In determining the effective amount, a number of factors are considered, including, but not limited to the species of fish; the degree of parasite infestation; the response of the fish population; the mode of administration; the bioavailability characteristics of the preparation administered; the dose regimen selected; the use of concomitant medication; and other relevant circumstances.

"Therapeutically effective amount", as used herein, unless otherwise indicated, refers to an amount that (1) treat the particular parasitic infestation, (ii) attenuates, ameliorates, or eliminates one or more symptoms of the particular parasitic infestation, or (iii) prevents or delays the onset of one or more symptoms of the particular parasitic infestation described herein.

The compound of Formula (I), or a salt thereof, may be administered to the fish by any route which has the desired effect including, but not limited to oral administration, parenteral administration by intraperitoneal or intramuscular injection or topical administration, e.g., in the form of a bath.

Therefore, in one embodiment the compound is applied by oral administration to fish, by topical administration such as by bath treatment/wherein the bath treatment comprises immersion of fish in water containing a therapeutically effective amount of a compound. (medicated water) or injected into the fish by intraperitoneal or intramuscular injection.

In one embodiment fish are treated by oral administration, e.g., via their feed. Alternatively topical by bath treatment, for example in a "medicinal bath" wherein the fish are placed and where they are kept for a period of time (minutes to several hours) e.g., when being transferred from one breeding basin to another.

In particular cases treatment can also be carried out parenterally, for example by injection such as by intraperitoneal or intramuscular injection. It is also possible to treat the biotope of the fish temporarily or continuously, e.g., the net cages, entire ponds, aquaria, tanks, or basins in which the fish are kept.

One aspect of the invention is a composition comprising one or more compounds of Formula (I) and veterinarily acceptable formulation auxiliaries for use to control parasitic infestations in a fish population.

"Veterinary acceptable" as used herein, unless otherwise indicated, indicates that a component must be compatible chemically and/or toxicologically, with the other ingredients comprising a composition, composition, and/or the fish being treated therewith. The term "pharmaceutically" acceptable has the same meaning as that recited for "veterinary" acceptable.

The compositions include those suitable for the foregoing administration routes. The compositions can conveniently be presented in unit dosage form and can be prepared by any of the methods well known in the art of veterinary science. In general, the compositions are prepared by uniformly and intimately bringing into association the active ingredient with liquid carriers or finely divided solid carriers or both, and then, if necessary, shaping the product.

The compound is administered in compositions which are adjusted to the applications. Compositions for oral administration are, for example, powders, granulates, solutions, emulsifiable concentrates or suspension concentrates which are mixed homogeneously as feed additives with the feed, or powders, granulates, solutions, emulsifiable concentrates or suspension concentrates which are administered in the form of pills, the outer coat of which can consist e.g., of fish feed compositions which cover the active compound completely.

Compositions for bath application or for treating the biotope are powders, granulates, solutions, emulsions or suspensions, tablets, or the active compound itself.

The compositions are prepared in a manner known per se, typically by mixing, granulating and/or compacting the active compound with solid or liquid carriers, where appropriate with the addition of further adjuvants, such as emulsifiable or dispersing agents, solubilisers, colourants, antioxidants and/or preservatives.

In practice it is also possible to use, for example, those forms of application where the active compound is contained in a readily water-soluble matrix of a film, or in films from which it diffuses over the period of application.

The diluted compositions of this invention are prepared by contacting the compound of Formula (I) with liquid and/or solid composition assistants by stepwise mixing and/or grinding such that an optimal development of the antiparasitic activity of the composition is achieved which conforms with the application.

The bath application of the compositions of this invention to the parasites to be controlled can be carried out, for example, such that the compositions are placed in the cage in the form of solutions, emulsions, suspensions, powders, or tablets, where they are quickly dissolved and dispersed by the movement of the fish and the flow of the water.

Bath Treatment

Compounds of Formula (I) can be administered to fish by bath treatment, for example by placing the fish into a "medicinal bath" and keeping them there for a period of time (minutes to several hours), for example, when being transferred from one net pen or breeding basin to another.

Therefore, in one embodiment an effective amount of at least one the compound of Formula (I) is administered to fish by topical administration, preferably by immersion of fish in water containing a therapeutically effective amount of one or more compounds of Formula (I). For use as a bath treatment, compound of Formula (I) or a composition, comprising at least one compound of Formula (I), can be dissolved, or suspended in the water containing the fish and/or parasite, thereby forming medicated water.

Another aspect of the invention is a composition comprising at least one compound of Formula (I) for dilution for use as a bath immersion treatment for controlling a parasitic infestation on fish from sea lice.

In one embodiment such composition comprises one or more compounds of Formula (I) and veterinarily acceptable formulation auxiliaries in the form of a stock solution for dilution in a volume of water to form medicated water for use as a bath immersion treatment. Preferably the effective amount in the medicated water is about 2 ppb to about 500 ppb.

In one embodiment a stock solution is used, a concentrated solution of the compound(s) in a liquid carrier comprising a solvent and solubilizer, that can be diluted with large volumes of water.

In yet another aspect of the invention, the composition is a stock solution of compound of Formula (I) for dilution in a volume of water to be used as a bath immersion treatment for controlling a parasitic sea lice infestation on a fish.

In yet another aspect of the invention, the stock solution of compound of Formula (I) comprises a solvent, and optionally, a solubilizer.

The solvent can be a non-aqueous polar solvent such as methanol, ethanol, benzyl alcohol, isopropanol, acetone, methylene chloride, butyl diglycol, N-methyl-2-pyrrolidone, dimethylacetamide, dimethylformamide, dimethyl sulfoxide, polyoxyethylated ether, propylene glycol, ethylene glycol, and mixtures thereof. In yet another aspect of the invention, the non-aqueous polar solvent is selected from ethanol, benzyl alcohol, isopropanol, acetone, butyl diglycol, N-methyl-2-pyrrolidone, dimethylacetamide, dimethylformamide, dimethyl sulfoxide, and mixtures thereof. In yet another aspect of the invention, the non-aqueous polar solvent is selected from benzyl alcohol, butyl diglycol, N-methyl-2-pyrrolidone, dimethyl sulfoxide, and mixtures thereof.

The composition can further comprise a solubilizer such as a polyoxyethylene castor oil derivative, polysorbate, caprylic/capric glyceride, poloxamer, polyoxyethylene alkyl ether, polyoxylglyceride, sorbitan fatty acid ester, polyoxyethylated 12-hydroxystearic acid, propylene glycol esters, polyglycerol esters, polyvinylpyrrolidone, cyclodextrin, polyethylene glycols, glyceryl stearates, caprylic glycerides, glyceryl monooleate, capric glycerides, alcohol ethoxylates, and mixtures thereof.

The compound of Formula (I) can be used to prepare immersion baths with different concentrations of compound of Formula (I) to achieve the dosing concentration required. A stock solution can be diluted at least once before mixing into water or can be poured directly into the volume of water for the treatment of fish.

The concentration of the compound during application to the fish depends on the manner and duration of treatment and also on the age and condition of the fish being treated. A typical immersion time ranges from about 15 minutes to about 4 hours, preferably from about 15 minutes to 2 hours, and more preferably from about 30 minutes to about 1 hour.

Compound of Formula (I) can be used in a bath at a therapeutically effective amount or concentration of about 2 ppb to about 500 ppb; or from about 5 ppb to about 500 ppb; or from about 5 ppb to about 250 ppb; or from about 5 ppb to about 200 ppb; or from about 5 ppb to about 100 ppb; or about 5 ppb to about 90 ppb; or about 5 ppb to about 80 ppb; or about 5 ppb to about 60 ppb; or about 5 ppb to about 50 ppb; or about 5 ppb to about 40 ppb; or about 5 ppb to about 25 ppb in water, based on total water volume.

All effective concentrations are ppb as measured in a volume of water (fresh, salt, brackish) for treating fish against a copepod crustacean species, particularly, sea lice. The concentrations are achieved by adding a volume of the concentrated stock solution of compound of Formula (I), for example 50 mg/ml or 100 mg/ml, to the enclosure containing the fish. The skilled person can determine how much compound stock solution should be added from knowledge of the volume of the enclosure containing the fish and the concentration of the stock solution.

Medicated Feed, Premix

The active compound in these compositions is used in pure form, as a solid active compound e.g., in a specific particle size or, preferably, together with—at least—one of the adjuvants which are conventionally used in composition technology, such as extenders, typically solvents or solid carriers, or surface-active compounds (surfactants).

The compound may be added to the feed by customary methods, by simply mixing as a pure compound, such as a powder, or mixed with edible, nontoxic veterinarily acceptable excipients in the form of a veterinary composition and include as a premix, in the form of a solution or suspension, granules, pellets.

In one embodiment of the present invention, the compound of Formula (I), or a salt thereof, is administered in a medicated fish feed.

Another embodiment is therefore a composition that comprises one or more compounds of Formula (I) and veterinarily acceptable formulation auxiliaries for oral administration via feed.

A specific composition is a "premix" that facilitates mixing of the relatively low amount of active ingredient homogeneously in/on fish feed (in tons).

Therefore, one aspect of the current invention is a premix comprising nutrients, formulation auxiliaries and at least one compound of Formula (I).

In one embodiment the nutritional fish feed is in the form of pellets that are mixed or coated with a composition comprising one or more compounds of Formula (I) as defined in claim 1. Such composition can include the compounds of Formula (I) as a solution or in a particulate form.

Another aspect of the current invention is medicated fish feed comprising the composition or premix and nutritional fish feed. Such feed is prepared by commercial feed mills according to the instructions of a veterinarian or based on the label and shipped to the fish farm. Alternatively, such medicated feed is prepared at the fish farm.

In one embodiment the medicated fish feed is administered daily for a period of 3 to 14 days.

In one embodiment of the present invention, the compound of Formula (I), or a salt thereof, is orally administered at a daily dose of between 1 and 10 mg/kg of fish biomass, preferably at a daily dose of between 3 and 7 mg/kg of fish biomass and most preferably at a daily dose of about 5 mg/kg of fish biomass.

In one embodiment, the overall treatment period during which the compound of Formula (I), or a salt thereof, is administered is 3 to 14 days (about 2 weeks), in one embodiment 3 to 7 days, in another embodiment 5 to 14 days, in another embodiment 5 to 10 days (about 1 and a half weeks) and preferably 7 days. During the overall treatment period, the compound of Formula (I), or a salt thereof, may be administered, for example, daily or once every two days. Preferably, it is administered daily. In a preferred embodiment, administration is daily for a period of 7 days.

In a preferred embodiment, the compound of Formula (I), or a salt thereof, is orally administered at a daily dose of between 1 and 10 mg/kg of fish biomass for a period of 3 to 14 days (about 2 weeks). In another preferred embodiment, the compound of Formula (I), or a salt thereof, is orally administered at a daily dose of between 3 and 7 mg/kg of fish biomass for a period of 5 to 10 days. In a more preferred embodiment, the compound of Formula (I), or a salt thereof, is orally administered at a daily dose of about 5 mg/kg of fish biomass for a period of 7 days.

It will be understood that the amount of the compound that is administered to a fish to achieve the desired effect can be varied because of the favorable non-toxic properties of the compound. In one embodiment, the compound is administered orally at about 0.005 to 5000 mg/kg, in particular 0.01 to 500 mg/kg (i.e., mg compound per kg fish body weight per day). Moreover, the compound can be administered at relatively high doses, such as exceeding (i.e., greater than) 0.01 mg/kg, 0.1 mg/kg, 1 mg/kg, 10 mg/kg or even greater than 100 mg/kg. The duration of administration can be from a few hours or days up to several years.

Hence, the oral administration comprises administering a medicated fish feed comprising the compound of Formula (I) to a fish population. Fish feed is typically in the form of granules or pellets. Common ingredients of said fish feed granules or pellets include fishmeal, fish oil, vegetable proteins, saccharides, and polysaccharides (including mannans, glucans and alginates). In addition, excipients such as pigments, vitamins, minerals, and binders may also be included.

The compound of Formula (I), or a salt thereof, may be incorporated into the feed prior to pelleting or alternatively, the compound of Formula (I), or a salt thereof, may be coated onto the granules or pellets, either on its own or in the form of a pre-mix. The pre-mix may contain, in addition to the active compound, one or more veterinarily acceptable excipients such as starch, fumed silica, microcrystalline cellulose, lactose and a preservative.

The compound may be incorporated into the feed mixture prior to pelleting. However, it is preferred to coat the pellets or granules with compound of Formula (i). For example, commercially available fish pellets or granules are coated with compound of Formula (I) using a solution in a veterinarily acceptable solvent or alternatively suspended in a carrier or with a pre-mix containing the compound of Formula (I) and one or more veterinary acceptable excipients such as a starch, fumed silica (Aerosil®), microcrystalline cellulose, lactose, or the like. In addition, a typical preservative may be present.

The concentration of compound of Formula (I) in the pre-mix may be chosen within a broad range; for example, a compound of Formula (I) concentration of from 0.001 to 90% w/w, preferably from 1 to 50% w/w, and more preferably from 5 to 15% w/w, according to a further embodiment from 0.001 to 10% w/w, preferably from 0.05 to 5% w/w and in particular from 0.15 to 2.5% w/w, based in each case on the entire weight of the pre-mix, has proven as valuable.

The feed pellets may be coated with the pre-mix by a dry top-coating method. To this end the pre-mix is added to the pellets, and the resulting mixture is agitated/mixed to uniformly distribute the compound of Formula (I) onto the pellets. According to an alternative top-coating method with additional oil treatment, to the product of the above-described dry top-coating method is added fish or vegetable oil with continued mixing, until the pellets are thoroughly coated. According to still another embodiment, called vacuum coating method, the pre-mix is first dissolved/suspended in fish or vegetable oil, before being sprayed onto the pellets under vacuum. Preferred is a solution.

Following the addition of the active ingredient to the fish feed, the pellets or granules comprise, for example, from about 0.0005 to about 5% (w/w), preferably from about 0.001 to about 2.5% (w/w), and in particular from about 0.0025 to about 1.25% (w/w) compound of Formula (I), based on the entire weight of the fish feed.

In one embodiment of the present invention, the amount of the compound of Formula (i), or a salt thereof, present in the fish feed pre-mix composition is between about 5 and about 20% (w/w), preferably between about 10 and about 15% (w/w) and most preferably about 12.5% (w/w), based in each case on the entire weight of the pre-mix.

Combinations

The compounds and compositions can also be used in combination with one or more other physiologically active agents.

Therefore, in one embodiment the compound is co-administered with an additional physiologically active agent. Such combinations are selected based on the condition to be treated, cross-reactivities of ingredients, and pharmacological properties of the combination. For instance, multifunctional agents, such as polyvalent vaccines are preferable in fish treatment, thus the composition may be administered with antigens targeting bacterial or viral diseases. In one embodiment the compound of Formula (i) is co-administered with one or more antigen, optionally the compound and antigen are administered together with an adjuvant.

These compounds and compositions can be administered together with, or in the same course of, therapy with the compounds and compositions described herein. Co-administration means that the individual components of the combination can be administered either sequentially or simultaneously in separate or combined veterinary compositions.

While the administration of a compound of Formula (I) alone provides in general a control of sea lice infestations for extended periods of time, said control may in certain circumstances be further improved by the use of compound of Formula (I) in combination with another physiologically active agent.

Such physiologically active agent is either another antiparasitic, especially a sea louse controlling agent; an antibiotic, or a vaccine component including immune enhancing agents; or a feed ingredient containing immune modifying agents.

Such combination treatments might be required where the fish have already been infested with parasites, which have matured before the compound of Formula (I) treatment, or in case rapid clearance of the parasites is desired.

Therefore, in one embodiment the compound of Formula (I) is co-administered with at least one additional physiologically active agent.

Suitable antiparasitic agents are, for example, hydrogen peroxide; formaldehyde; an organophosphate such as trichlorfon, malathion, dichlorvos or azamethiphos; a macrocyclic lactone such as ivermectin, emamectin benzoate or moxidectin; a pyrethroid such as cypermethrin, or deltamethrin; a neonicotinoid such as imidacloprid, nitenpyram, thiamethoxam or thiacloprid; a spinosyn such as spinosad; an IGR such as epofenonane, triprene, methoprene or lufenuron or a carbamate such as phenoxycarb.

If compound of Formula (I) is used in combination with another compound being active in the control of sea lice, said combination partner is preferably an organophosphate, a pyrethroid such as cypermethrin or deltamethrin, a macrocyclic lactone such as emamectin benzoate; hydrogen peroxide; or a neonicotinoid such as imidacloprid or thiacloprid.

In another embodiment, the combination partner is one or more isoxazoline compounds known in the art. Isoxazoline active agents are highly effective against a variety of ectoparasites and combination with the compound of Formula (I) would expand the scope of efficacy against these parasites. Particularly useful isoxazoline active agents that can be combined with the compound include afoxolaner (including substantially pure active enantiomer), sarolaner, fluralaner (including substantially pure active enantiomer) and lotilaner.

These active agents are described in U.S. Pat. No. 7,964,204, US 2010/0254960 A1, US2011/0159107, US2012/0309620, US2012/0030841, US2010/0069247, WO 2007/125984, WO 2012/086462, U.S. Pat. Nos. 8,318,757, 8,466,115, 8,618,126, 8,822,466, 8,383,659, 8,853,186, 9,221,835, US 2011/0144349, U.S. Pat. No. 8,053,452; US 2010/0137612, U.S. Pat. No. 8,410,153, US 2011/152081, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, US 2015/0126523, WO 2010/003923, WO 2010/003877, WO 2010/072602, WO 2014/134236, WO 2017/147352, U.S. Pat. Nos. 7,897,630, and 7,951,828, all of which are incorporated herein by reference in their entirety.

Another combination partner is 2-chloro-N-(1-cyanocyclopropyl)-5-[1-[2-methyl-5-(1,1,2,2,2-pentafluoroethyl)-4-(trifluoromethyl)pyrazol-3-yl]pyrazol-4-yl]benzamide (CAS RN 1621436). This compound is known as tigolaner.

A suitable combination treatment with compound of Formula (I) and another sea louse-controlling agent may be performed, for example, by treating the fish, in particular salmon, initially with compound of Formula (I) according to the in-feed method and regime as mentioned above, and thereafter, for example 3 months, preferably 5 months, more preferably 6 months and in particular 9 months following the end of the compound of Formula (i) in-feed treatment performing a treatment with the additional sea louse controlling agent; said second treatment may be a topical administration such as e.g. a bath treatment, or an oral administration such as e.g. an in-feed treatment or preferably a treatment by injecting the additional sea louse controlling agent to the fish. According to a preferred embodiment of this combination treatment, the in-feed treatment with the compound of Formula (i) takes place at the end of the freshwater phase of salmon evolution or at the beginning of their sea water phase.

A further combination treatment comprises first of all treating the fish, in particular salmon, with the additional sea louse controlling agent and thereafter, for example 1 hour to 2 months thereafter, preferably 1 hour to 1 month thereafter or in particular 1 week to 1 month thereafter, performing a compound of Formula (I) in-feed treatment according to the present invention as described above. According to a preferred embodiment of this combination treatment, the treatment with the additional sea louse controlling agent is a bath treatment, an in-feed treatment or injectable treatment which takes place at the beginning of the sea water phase, for example 1 hour to 3 months, preferably 6 hours to 2 months.

According to a further embodiment of the invention, the in-feed treatment with compound of Formula (i) is combined with a vaccination of the fish against typical bacterial or viral infections. Typical bacterial diseases to be treated by vaccination are, for example, vibriosis, furunculosis, wound diseases, atypical *Aeromonas salmonicida*, piscirickettsiosis or ERM/yersiniosis. Examples of viral diseases to be treated are pancreas disease/PDV, infectious pancreatic necrosis/IPNV or infectious salmon anemia/ISAV. The vaccine is in general applied by a bath or in-feed treatment or preferably by injection. The vaccination may take place either shortly before, during or after the compound of Formula (i) in-feed treatment of the fish.

According to an aspect this combination treatment, the first treatment is the bath treatment with a compound of Formula (i) followed with an in-feed treatment with hexaflumuron or lufenuron, a compound of Formula (i), or emamectin that may provide lasting protection against sea lice. According to another aspect this combination treatment, the first treatment is an in-feed treatment with hexaflumuron or lufenuron, a compound of Formula (I), or emamectin that may provide lasting protection against sea lice followed by the bath treatment with compound of Formula (I).

In another embodiment a compound of Formula (I) is administered in combination with vitamins that improve the health of the animal.

Evidence for the resistance of sea lice to chemotherapeutants is abundant around the world.

It has been surprisingly found that the compounds of Formula (I) are effective to control sea lice populations, that have been identified as resistant against commercially available sea lice chemotherapeutics from the class of organophosphates, macrocyclic lactones, especially avermectins, and pyrethroids as shown in Examples.

"Resistance," as used herein, refers to reduced potency of a compound as compared to naive parasites, particularly sea lice. The first incidence of this phenomenon was reported in Norway, where tolerance to organophosphates, in particular, azamethiphos, increased to the point of having totally lost their effect by the mid-1990s. Later, treatment failures associated with pyrethroids were reported in Norway, Scotland, and Ireland. Subsequent analysis, based on bioassays, confirmed reduced sensitivity to deltamethrin and cypermethrin. A recent study based on bioassays confirmed the low sensitivity of *C. rogercresseyi* to pyrethroids). Therefore, it is particularly important to have new effective compounds available that can effectively control such resistant parasite populations.

Therefore, in one embodiment a sea lice infestation with parasites that show resistance against macrocyclic lactones, organophosphates and/or pyrethroids is controlled and sea lice have been found to be resistant against macrocyclic lactone, organophosphates and or pyrethroid antiparasitic agents.

In one embodiment such sea lice populations are resistant against one or more of emamectin, deltamethrin, or organophosphates.

Kits

Another aspect of the current invention is a kit comprising a compound of Formula (I) or a composition, as described above comprising such compound and instructions for administration of the composition to fish.

In one embodiment a kit comprises a premix, as described above and instructions for preparation of medicated fish feed and/or instructions for administration of the medicated fish feed to a fish population to control sea lice infestation as described in more detail above.

In another embodiment a kit comprises the stock solution as described above and instructions for preparation of medicated water for a bath treatment, and/or instructions for immersion of fish to control sea lice infestation as described in more detail above.

The following table shows compounds of the invention

Formula (II)

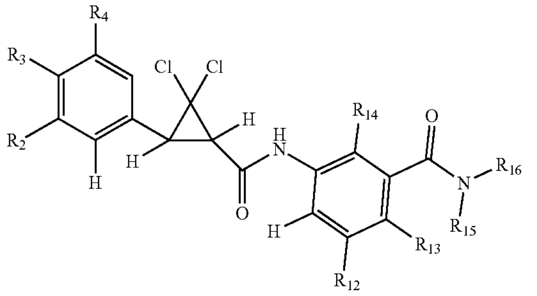

| # | stereo | R2 | R3 | R4 | R12 | R13 | R14 | R15 | $R^{16}$ |
|---|---|---|---|---|---|---|---|---|---|
| 1500 | Racemate | Cl | H | Cl | H | Cl | H | H | 2,2,2-trifluoroethyl |
| 1501 | Racemate | H | Cl | Cl | H | Cl | H | H | 1-cyanocyclopropyl |
| 1502 | Racemate | Cl | H | Cl | H | Cl | H | H | isobutyl |
| 1503 | Racemate | Cl | H | Cl | H | Cl | H | H | n-hexyl |
| 1504 | Racemate | Cl | H | Cl | H | Cl | H | H | n-pentyl |
| 1505 | Racemate | Cl | H | Cl | H | Cl | H | H | cyclopropylmethyl |
| 1506 | Racemate | Cl | H | Cl | H | Cl | H | H | 3-(2,2,2-trifluoroethoxy)propyl |
| 1507 | Racemate | Cl | H | Cl | H | Cl | H | H | n-butyl |
| 1508 | Racemate | H | H | $CF_3$ | H | Cl | H | H | 3,3-difluorocyclobutyl |
| 1509 | Racemate | Cl | H | Cl | H | Cl | H | H | ethyl |
| 1510 | Racemate | Cl | H | Cl | H | Cl | H | H | oxetan-3-yl |
| 1511 | Racemate | Cl | H | Cl | H | Cl | H | H | 2-methoxyethyl |
| 1512 | Racemate | Cl | H | Cl | H | Cl | H | H | 2-ethoxyethyl |
| 1513 | Racemate | Cl | H | $CH_3$ | H | Cl | H | H | 3,3-difluorocyclobutyl |
| 1514 | Racemate | $CH_3$ | Cl | Cl | H | Cl | H | H | 1-cyanocyclopropyl |
| 1515 | Racemate | Cl | H | Cl | H | Cl | H | H | 1-cyanocyclopropyl |
| 1516 | Racemate | Cl | H | Cl | H | Cl | H | H | 2-oxopyrrolidin-3-yl |
| 1517 | Racemate | Cl | H | Cl | H | Cl | H | H | [(1R)-1-methyl-2-(3,3,3-trifluoropropylsulfanyl)ethyl] |
| 1518 | Racemate | Cl | H | Cl | H | Cl | H | H | (1R)-1-methyl-2-(2,2,2-trifluoroethylsulfanyl)ethyl |

-continued

Formula (II)

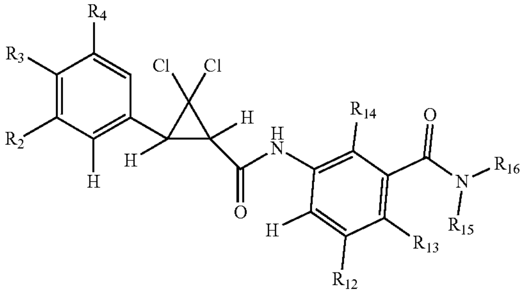

| # | stereo | R2 | R3 | R4 | R12 | R13 | R14 | R15 | $R^{16}$ |
|---|---|---|---|---|---|---|---|---|---|
| 1519 | Racemate | Cl | H | Cl | H | Cl | H | H | [(1R)-1-methyl-2-(3,3,3-trifluoropropylsulfonyl)ethyl] |
| 1520 | Racemate | Cl | H | Cl | H | Cl | H | H | (1R)-1-methyl-2-(2,2,2-trifluoroethylsulfonyl)ethyl |
| 1521 | Racemate | Cl | H | Cl | H | Cl | H | H | (1R)-1-methyl-2-(2,2,2-trifluoroethylsulfinyl)ethyl |
| 1522 | Racemate | Cl | H | Cl | H | Cl | H | H | 1-(2-methoxyacetyl)azetidin-3-yl |
| 1523 | Racemate | Cl | H | Cl | H | Cl | H | H | 1-methylcyclopropyl |
| 1524 | Racemate | Cl | H | Cl | H | Cl | H | H | 1-methoxycarbonyl-3-methylsulfanyl-propyl |
| 1525 | Racemate | Cl | H | Cl | H | Cl | H | H | 2-oxotetrahydrothiophen-3-yl |
| 1526 | Racemate | Cl | H | Cl | H | Cl | H | H | 2-oxotetrahydrofuran-3-yl |
| 1527 | Racemate | Cl | H | Cl | H | Cl | H | H | 2-(2-oxoimidazolidin-1-yl)ethyl |
| 1528 | Racemate | Cl | H | Cl | H | Cl | H | H | (4R)-2-ethyl-3-oxo-isoxazolidin-4-yl |
| 1529 | Racemate | Cl | H | Cl | H | Cl | H | H | 1-(2,2,2-trifluoroethylcarbamoyl)cyclopropyl |
| 1530 | Racemate | Cl | H | Cl | H | Cl | H | H | 1-(ethylcarbamoyl)cyclopropyl |
| 1531 | 1R,3R | Cl | H | Cl | H | Cl | H | H | 3,3-difluorocyclobutyl |
| 1532 | Racemate | CN | H | Cl | H | Cl | H | H | 1-cyanocyclopropyl |
| 1533 | Racemate | Cl | H | Cl | H | Cl | H | H | difluor-cyclobutyl |
| 1534 | Racemate | Cl | H | Cl | H | Cl | H | H | 2-fluoroethyl |
| 1535 | Racemate | Cl | H | Cl | H | Cl | H | H | 2,2,2-trifluoroethyl |
| 1536 | Racemate | Cl | F | H | H | Cl | H | H | 2-fluoroethyl |
| 1537 | Racemate | Cl | F | H | H | Cl | H | H | 2,2,2-trifluoroethyl |
| 1538 | Racemate | Cl | F | H | H | Cl | H | H | 3,3,3-trifluoropropyl |
| 1539 | Racemate | Cl | H | Cl | Cl | Cl | H | H | 2-fluoroethyl |
| 1540 | Racemate | Cl | H | Cl | Cl | Cl | H | H | n-propyl |
| 1541 | 1R,3R | Cl | Cl | Cl | H | Cl | H | H | 1-cyanocyclopropyl |
| 1542 | 1S,3S | Cl | Cl | Cl | H | Cl | H | H | 1-cyanocyclopropyl |
| 1543 | Racemate | Cl | H | Cl | H | Cl | H | H | 3-oxocyclobutyl |
| 1544 | Racemate | F | Br | F | H | Cl | H | H | 1-cyanocyclopropyl |
| 1545 | Racemate | $CHF_2$ | H | Cl | H | Cl | H | H | 1-cyanocyclopropyl |
| 1546 | Racemate | H | Cl | $CHF_2$ | H | Cl | H | H | 1-cyanocyclopropyl |
| 1547 | Racemate | $CHF_2$ | H | F | H | Cl | H | H | 1-cyanocyclopropyl |
| 1548 | Racemate | H | $CHF_2$ | Cl | H | Cl | H | H | 1-cyanocyclopropyl |
| 1549 | Racemate | H | H | $CHF_2$ | H | Cl | H | H | 1-cyanocyclopropyl |
| 1550 | Racemate | H | $CHF_2$ | H | H | Cl | H | H | 1-cyanocyclopropyl |
| 1551 | Racemate | F | F | F | H | Cl | H | H | 2,2,2-trifluoroethyl |
| 1552 | Racemate | Cl | H | Cl | Cl | Cl | H | H | 3,3,3-trifluoropropyl |
| 1553 | Racemate | Cl | H | Cl | Cl | Cl | H | H | ethyl |
| 1554 | Racemate | H | F | Cl | F | F | H | H | 2,2,2-trifluoroethyl |
| 1555 | Racemate | H | F | Cl | Cl | $CH_3$ | H | H | 2,2,3,3,3-pentafluoropropyl |
| 1556 | Racemate | H | F | Cl | $CH_3$ | F | H | H | 2,2,2-trifluoroethyl |
| 1557 | Racemate | H | F | Cl | $CH_3$ | Cl | H | H | 3-chloropropyl |
| 1558 | Racemate | H | F | Cl | H | F | F | H | 2-fluoroethyl |
| 1559 | Racemate | H | F | Cl | H | F | F | H | 2,2,2-trifluoroethyl |
| 1560 | Racemate | H | F | Cl | F | $CH_3$ | H | H | 2,2,3,3,3-pentafluoropropyl |
| 1561 | Racemate | H | F | Cl | Cl | $CH_3$ | H | H | 2,2,2-trifluoroethyl |
| 1562 | Racemate | H | F | Cl | $CF_3$ | Cl | H | H | 3,3,3-trifluoropropyl |
| 1563 | Racemate | H | F | Cl | H | F | F | H | 3-chloropropyl |
| 1564 | Racemate | Cl | F | H | H | Cl | Cl | H | 2,2,3,3,3-pentafluoropropyl |
| 1565 | Racemate | H | F | Cl | F | Cl | H | H | 2,2,2-trifluoroethyl |
| 1566 | Racemate | H | F | Cl | Cl | $CH_3$ | H | H | 3-chloropropyl |
| 1567 | Racemate | H | F | Cl | F | $CH_3$ | H | H | 2,2,2-trifluoroethyl |
| 1568 | Racemate | H | F | Cl | H | Cl | Cl | H | 2,2,2-trifluoroethyl |
| 1569 | Racemate | H | F | Cl | $CH_3$ | F | H | H | 3-chloropropyl |
| 1570 | Racemate | H | F | Cl | Cl | F | H | H | 2,2,2-trifluoroethyl |
| 1571 | Racemate | H | F | Cl | H | F | F | H | 2,2,3,3,3-pentafluoropropyl |
| 1572 | Racemate | H | F | Cl | F | Cl | H | H | 2,2,3,3,3-pentafluoropropyl |
| 1573 | Racemate | H | F | Cl | H | F | F | H | 3,3,3-trifluoropropyl |
| 1574 | Racemate | H | F | Cl | F | F | H | H | 3-chloropropyl |
| 1575 | Racemate | H | F | Cl | H | Cl | Cl | H | 2-fluoroethyl |

-continued

Formula (II)

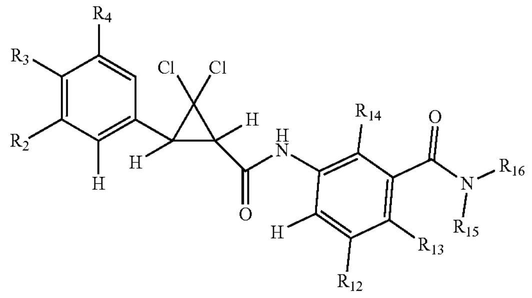

| # | stereo | R2 | R3 | R4 | R12 | R13 | R14 | R15 | $R^{16}$ |
|---|---|---|---|---|---|---|---|---|---|
| 1576 | Racemate | H | F | Cl | $CF_3$ | Cl | H | H | 2,2,3,3,3-pentafluoropropyl |
| 1577 | Racemate | H | F | Cl | F | $OCH_3$ | H | H | 2,2,3,3,3-pentafluoropropyl |
| 1578 | Racemate | H | F | Cl | $CF_3$ | Cl | H | H | 2,2,2-trifluoroethyl |
| 1579 | Racemate | H | F | Cl | $CH_3$ | F | H | H | 2,2,3,3,3-pentafluoropropyl |
| 1580 | Racemate | H | F | Cl | F | F | H | H | 2,2,3,3,3-pentafluoropropyl |
| 1581 | Racemate | H | F | Cl | Cl | F | H | H | 2,2,3,3,3-pentafluoropropyl |
| 1582 | Racemate | H | F | Cl | H | Cl | Cl | H | 3-chloropropyl |
| 1583 | Racemate | H | F | Cl | H | Cl | Cl | H | 3,3,3-trifluoropropyl |
| 1584 | 1R,3R | F | F | H | H | Cl | H | H | 2,2,2-trifluoroethyl |
| 1585 | 1R,3R | Cl | Br | H | H | Cl | H | H | 1-cyanocyclopropyl |
| 1586 | 1S,3S | Cl | Br | H | H | Cl | H | H | 1-cyanocyclopropyl |
| 1587 | 1R,3R | F | $CHF_2$ | H | H | Cl | H | H | 1-cyanocyclopropyl |
| 1588 | 1S,3S | Cl | $CHF_2$ | H | H | Cl | H | H | (1-cyanocyclopropyl) |
| 1589 | 1R,3R | Cl | F | H | F | F | H | H | 1-cyanocyclopropyl |
| 1590 | 1R,3R | Cl | H | Cl | H | Cl | H | H | 1-cyanocyclopropyl |
| 1591 | 1S,3S | F | F | H | H | Cl | H | H | 2,2,2-trifluoroethyl |
| 1592 | 1R,3R | Cl | H | Cl | H | Cl | H | H | 2,2,2-trifluoroethyl |
| 1593 | 1R,3R | F | F | F | H | Cl | H | H | 2,2,2-trifluoroethyl |
| 1594 | 1R,3R | Cl | H | Cl | F | F | H | H | 1-cyanocyclopropyl |
| 1595 | 1R,3R | Cl | Cl | Cl | H | Cl | H | H | 3-[(2-cyclopropylacetyl)amino]-2,4-difluoro-phenyl |
| 1596 | 1R,3R | H | Cl | Cl | H | Cl | H | H | 3-[(1-cyanocyclopropanecarbonyl)amino]-2,4-difluoro-phenyl |
| 1597 | 1R,3R | H | Cl | Cl | H | Cl | H | H | 3-[(2-cyclopropylacetyl)amino]-2,4-difluoro-phenyl |
| 1598 | 1R,3R | H | Cl | Cl | H | Cl | H | H | 2,4-difluoro-3-[(3-oxocyclobutanecarbonyl)amino]phenyl |
| 1599 | 1R,3R | H | Cl | Cl | H | Cl | H | H | 3-[(2,2-difluorocyclopropanecarbonyl)amino]-2,4-difluoro-phenyl |
| 1600 | 1S,3S | H | Cl | F | H | Cl | H | H | 1-cyanocyclopropyl |
| 1601 | 1R,3R | H | H | $CF_3$ | H | Cl | H | H | 3,3-difluorocyclobutyl |
| 1602 | Racemate | F | F | F | H | Cl | H | H | 2,2,2-trifluoro-1-methyl-ethyl |
| 1603 | 1R,3R | F | F | F | H | Cl | H | H | 2,2,2-trifluoro-1,1-dimethyl-ethyl |
| 1604 | 1R,3R | F | F | F | H | Cl | H | H | 1-(trifluoromethyl)cyclopropyl |
| 1605 | 1R,3R | Cl | H | Cl | H | F | H | H | 1-cyanocyclopropyl |
| 1606 | 1R,3R | H | Cl | F | H | Cl | H | H | 1-cyanocyclopropyl |
| 1607 | 1S,3S | Cl | F | Cl | H | Cl | H | H | 1-cyanocyclopropyl |
| 1608 | 1R,3R | H | F | Cl | H | Cl | H | H | 1-cyanocyclopropyl |
| 1609 | 1R,3R | Cl | F | Cl | H | Cl | H | H | 1-cyanocyclopropyl |
| 1610 | 1R,3R | Cl | H | Cl | H | CN | H | H | 1-cyanocyclopropyl |
| 1611 | 1S,3S | $CF_3$ | H | H | H | Cl | H | H | 3,3-difluorocyclobutyl |
| 1612 | 1R,3R | $CF_3$ | H | $CF_3$ | H | Cl | H | H | 1-cyanocyclopropyl |
| 1613 | 1R,3R | $CF_3$ | H | $CF_3$ | H | Cl | H | H | 2,2,2-trifluoroethyl |
| 1614 | 1R,3R | $CF_3$ | H | $CF_3$ | H | Cl | H | H | prop-2-ynyl |
| 1615 | 1R,3R | $CF_3$ | H | $CF_3$ | F | F | H | H | 1-cyanocyclopropyl |
| 1616 | 1R,3R | Cl | H | Cl | F | F | H | H | 1-methylcyclopropyl |
| 1617 | 1R,3R | Cl | H | Cl | F | F | H | H | 1-ethynylcyclopropyl |
| 1618 | 1R,3R | Cl | H | Cl | F | F | H | H | cyclopropyl |
| 1619 | 1R,3R | Cl | H | Cl | H | Cl | H | H | 1-methylcyclopropyl |
| 1620 | 1R,3R | Cl | H | Cl | H | Cl | H | H | 1-ethynylcyclopropyl |
| 1621 | 1R,3R | Cl | H | Cl | H | Cl | H | H | cyclopropyl |
| 1622 | 1R,3R | Cl | H | Cl | H | Cl | H | H | prop-2-ynyl |
| 1623 | 1R,3R | F | F | F | H | F | H | H | 1-cyanocyclopropyl |
| 1624 | 1R,3R | F | F | F | H | Cl | H | H | 1-cyanocyclopropyl |
| 1625 | 1R,3R | Cl | H | Cl | H | Cl | H | H | 3,3-difluorocyclobutyl |
| 1626 | 1R,3R | Cl | H | Cl | H | F | H | H | 1-methylcyclopropyl |
| 1627 | 1R,3R | Cl | H | Cl | H | F | H | H | 1-(trifluoromethyl)cyclopropyl |
| 1628 | 1R,3R | Cl | H | Cl | F | F | H | H | 3,3-difluorocyclobutyl |
| 1629 | 1R,3R | Cl | H | Cl | F | F | H | H | prop-2-ynyl |
| 1630 | 1R,3R | Cl | H | Cl | H | F | H | H | 3,3-difluorocyclobutyl |

-continued

Formula (II)

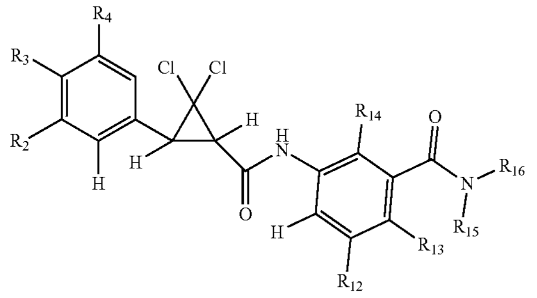

| # | stereo | R2 | R3 | R4 | R12 | R13 | R14 | R15 | $R^{16}$ |
|---|---|---|---|---|---|---|---|---|---|
| 1631 | 1R,3R | Cl | H | Cl | H | F | H | H | prop-2-ynyl |
| 1632 | 1R,3R | Cl | H | Cl | H | F | H | H | cyclopropyl |
| 1633 | 1R,3R | Cl | H | Cl | H | F | H | H | 1-ethynylcyclopropyl |

FIG. 1 shows the structures of the compounds

EXAMPLES

The compounds are synthesized according to WO2018071327, WO2016168058, WO2016168056 and the following compounds were made according to the following synthesis scheme:

Synthetic Scheme of 1633

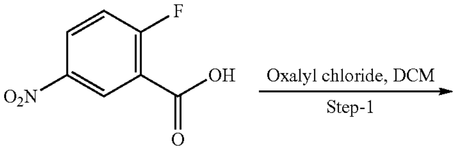

SM-1

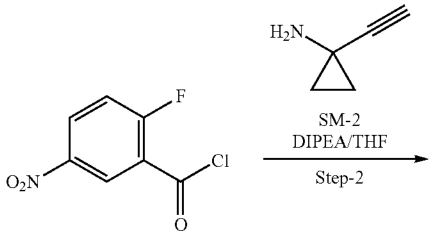

1

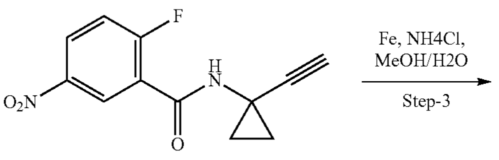

2

-continued

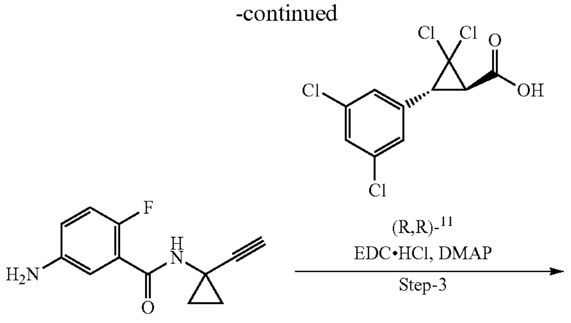

3

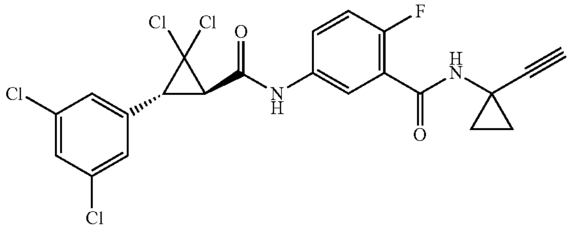

1633

Step-1

Synthesis of 2-fluoro-5-nitrobenzoyl chloride (1)

1

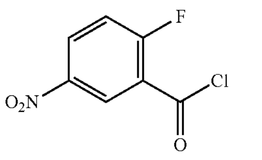

Experimental Procedure

To a stirred solution of 2-fluoro-5-nitrobenzoic acid (SM-1) (4 g, 21.62 mmol) in DCM (60 ml) was added oxalyl chloride (2.5 ml, 32.43 mmol) at 0° C. and stirred for 5 min.

To this catalytic amount of DMF (0.1 ml) was added and the reaction mixture was stirred at RT for 2 h. The progress of the reaction was monitored by TLC (50% Ethyl acetate in pet ether). After completion of reaction the reaction mixture was completely distilled off under vacuum to afford 2,fluoro-5-nitrobenzoyl chloride (1) (4.1 g, Crude) as light brown semi solid.

Step-2

Synthesis of N-(1-ethynylcyclopropyl)-2-fluoro-5-nitrobenzamide (2)

2

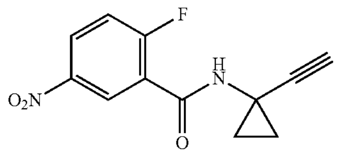

Experimental Procedure

The stirred solution of 1-ethynylcyclopropan-1-amine (SM-2) (1.4 g, 12.35 mmol) in THF (21 ml) was cooled to 0° C. and added DIPEA (5.3 ml, 30.88 mmol), stirred for 10 minutes. To this 2-fluoro-5-nitrobenzoyl chloride (1) (2.1 g, 10.29 mmol) in THF (20 ml) was added and reaction mixture stirred at RT for 6 h. The progress of the reaction was monitored by TLC (50% Ethyl acetate in pet ether (Rf=0.7). After completion of reaction H2O (20 ml) added to the reaction mixture and extracted in EtOAC (2×30 ml), dried over Na2SO4 and concentrated under reduced pressure to afford N-(1-ethynylcyclopropyl)-2-fluoro-5-nitrobenzamide (2) (2.8 g, crude) as brown solid. ESIMS m/z 249.19 ($[M+H]^+$).

Step-3

Synthesis of 5-amino-N-(1-ethynylcyclopropyl)-2-fluorobenzamide (3)

3

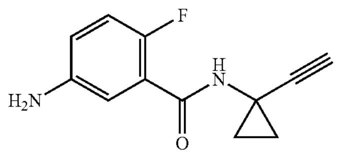

Experimental Procedure

The stirred solution of N-(1-ethynylcyclopropyl)-2-fluoro-5-nitrobenzamide (2) (6.0 g, 22.53 mmol) in MeOH/$H_2O$ (85 ml, 1:1 ratio), Fe (3.1 g, 56.45 mmol) and $NH_4Cl$ (6.0 g, 112.90 mmol) were added and RM stirred at 80° C. for 3 hours. The progress of the reaction was monitored by TLC (50% Ethyl acetate in pet ether (0.3 Rf). After completion of reaction, RM filtered through celite bed, washed with MeOH (50 ml) concentrated. H2O (40 ml) added and extracted in EtOAc (3×80 ml), dried over Na2SO4 and concentrated. Crude compound was purified through column chromatography (silica gel 100-200), Eluent gradient 30% Ethyl acetate in pet ether. Combined column fractions were concentrated and dried under reduced pressure to afford 5-amino-N-(1-ethynylcyclopropyl)-2-fluorobenzamide (3) (400 mg, 16%) as brown solid. ESIMS m/z 219.2 ($[M+H]^+$).

Step-4

Synthesis of 5-((1R,3R)-2,2-dichloro-3-(3,5-dichlorophenyl)cyclopropane-1-carboxamido)-N-(1-ethynylcyclopropyl)-2-fluorobenzamide (1633)

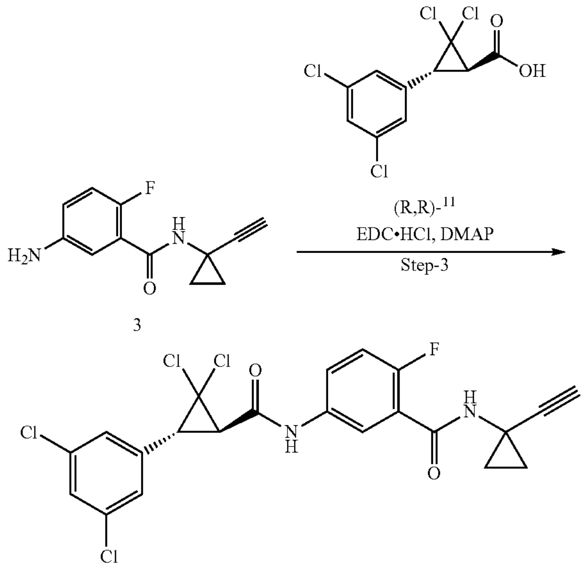

1633

Experimental Procedure

The stirred solution of (R,R)-11 (0.4 g, 1.33 mmol) in DCM (20 ml) was cooled to 0° C. and EDC·HCl (0.38 g, 1.99 mmol), DMAP (0.24 g, 1.99 mmol) were added and stirred for 10 min. To this mixture, 5-amino-2,3-difluoro-N-(prop-2-yn-1-yl)benzamide (3) (0.28 g, 1.33 mmol) was added and stirred at RT for 16 h. The progress of the reaction was monitored by TLC (50% Ethyl acetate in pet ether). After completion of reaction $H_2O$ (40 ml) added to the reaction mixture and extracted in DCM (2×50 ml), and the combined organic phases dried over $Na_2SO_4$ and concentrated. Crude compound was purified through column chromatography (silica gel 100-200). Eluent gradient 10% Ethyl acetate in pet ether to give -5-((1R,3R)-2,2-dichloro-3-(3,5-dichlorophenyl)cyclopropane-1-carboxamido)-N-(1-ethynylcyclopropyl)-2-fluorobenzamide (1633) (0.38 g, 40%) as pale yellow solid. $^1H$ NMR (400 MHz, DMSO-$d_6$) δ ppm 1.075 (s, 2H), 1.235-1.123 (m, 2H), 3.014 (s, 1H), 3.492-3.471 (d, J=8.4 Hz, 1H), 3.620-3.599 (d, J=8.4 Hz 1H), 7.300-7.254 (t, 1H), 7.547 (s, 2H), 7.622 (s, 1H), 7.749-7.731 (m, 1H), 7.862-7.848 (m, 1H) 8.954 (s, 1H), 10.770 (s, 1H): ESIMS m/z 499.02 ($[M+H]^+$).

Synthetic Scheme of 1620

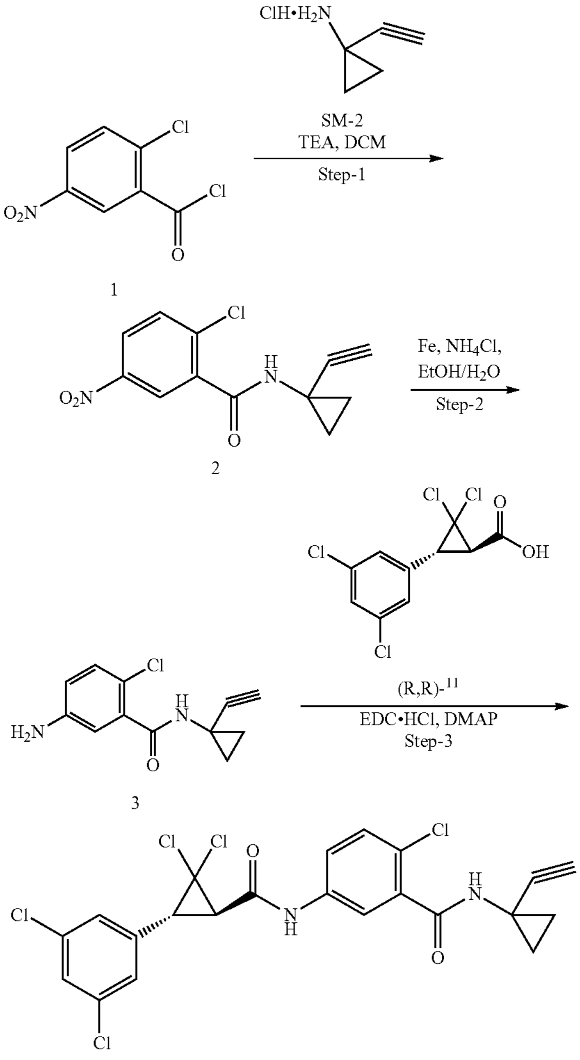

1620

Step-1

Synthesis of 2-chloro-N-(1-ethynylcyclopropyl)-5-nitrobenzamide (2)

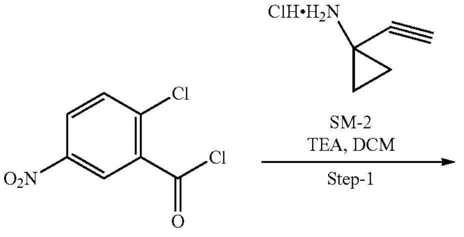

1

-continued

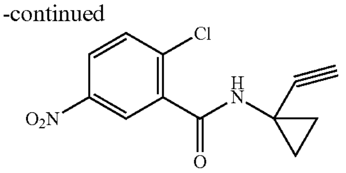

2

Experimental Procedure

The stirred solution of 1-ethynylcyclopropan-1-amine hydrochloride SM-2 (1.06 g, 9.09 mmol 0.82(d) in DCM (40 mL) was cooled to 0° C. and added TEA (3.83 ml, 27.27 mmol), stirred for 10 minutes. To this 2-chloro-5-nitrobenzoyl chloride (1) (2.0 g, 9.09 mmol) in DCM (10 mL) was added and the mixture was stirred at RT for 6 h. The progress of the reaction was monitored by TLC (50% Ethyl acetate in pet ether (0.7 Rf). After completion of reaction $H_2O$ (20 ml) added to the reaction mixture and extracted in DCM (2×30 ml), dried over $Na_2SO_4$ and concentrated under reduced pressure to afford 2-chloro-N-(1-ethynylcyclopropyl)-5-nitrobenzamide (2) (2.1 g, crude) as brown solid.

Step-2

Synthesis of 5-amino-2-chloro-N-(1-ethynylcyclopropyl)benzamide (3)

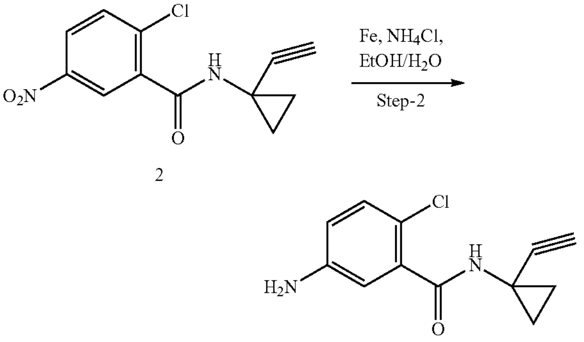

3

Experimental Procedure

The stirred solution of 2-chloro-N-(1-ethynylcyclopropyl)-5-nitrobenzamide (2) (2.1 g, 7.94 mmol) in EtOH/$H_2O$ (63 mL, 4:1 ratio), Fe (2.21 g, 39.71 mmol) and $NH_4Cl$ (2.12 g, 39.71 mmol) were added and RM stirred at 80° C. for 3 hours. The progress of the reaction was monitored by TLC (Ethyl acetate (0.4 Rf). After completion of reaction, RM filtered through celite bed, washed with 10% MeOH/DCM (50 mL). $H_2O$ (40 mL) added and extracted in 10% MeOH/DCM (3×80 mL), dried over $Na_2SO_4$ concentrated. Crude compound was purified through column chromatography (silica gel 100-200). Eluent gradient 15% Ethyl acetate in pet ether. Combined column fractions were concentrated and dried under reduced pressure to afford 5-amino-2-chloro-N-(1-ethynylcyclopropyl)benzamide (3) (0.8 g, 43%) as light brown solid.

Step-3

Synthesis of 2-chloro-5-((1R,3R)-2,2-dichloro-3-(3,5-dichlorophenyl)cyclopropane-1-carboxamido)-N-(1-ethynylcyclopropyl)benzamide (1620)

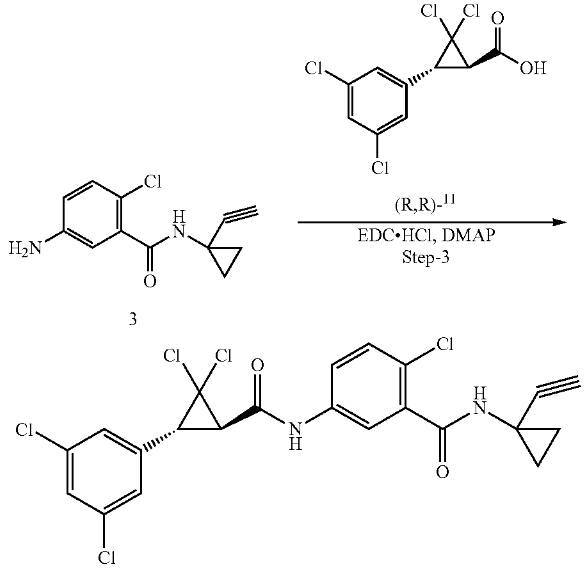

3

1620

Experimental Procedure

The stirred solution of (R,R)-11 (0.3 g, 1.00 mmol) in DCM (20 mL) was cooled to 0° C. and EDC·HCl (0.28 g, 1.5 mmol), DMAP (0.18 g, 1.5 mmol) were added and stirred for 10 min. To this 5-amino-2-chloro-N-(1-ethynylcyclopropyl)benzamide (3) (0.23 g, 1.00 mmol) was added and Rm stirred at RT for 6 h. The progress of the reaction was monitored by TLC (30% Ethyl acetate in pet ether (0.6 Rf). After completion of reaction $H_2O$ (40 mL) added to the reaction mixture and extracted in DCM (2×50 mL), dried over $Na_2SO_4$ and concentrated. Crude compound was purified through column chromatography (silica gel 100-200). Eluent gradient 27% Ethyl acetate in pet ether. Combined column fractions were concentrated and dried under reduced pressure to afford 2-chloro-5-((1R,3R)-2,2-dichloro-3-(3,5-dichlorophenyl)cyclopropane-1-carboxamido)-N-(1-ethynylcyclopropyl)benzamide (1620) (0.23 g, 45%) as off white solid. 1H NMR (400 MHz, DMSO-d6) δ ppm 1.06-1.03 (m, 2H), 1.23-1.15 (m, 2H), 3.031 (s, 1H), 3.50 (d, J=8.4 Hz, 1H), 3.621 (d, J=8.4 Hz, 1H), 7.47 (d, J=8.4 Hz, 1H), 7.54 (s, 2H), 7.62 (s, 1H), 7.71-7.66 (m, 2H), 9.07 (s, 1H), 10.84 (s, 1H): ESIMS m/z 515.10 ($[M+H]^+$).

Synthetic Scheme of 1617

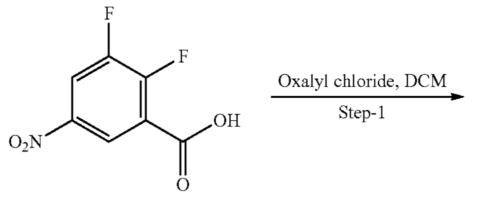

SM-1

-continued

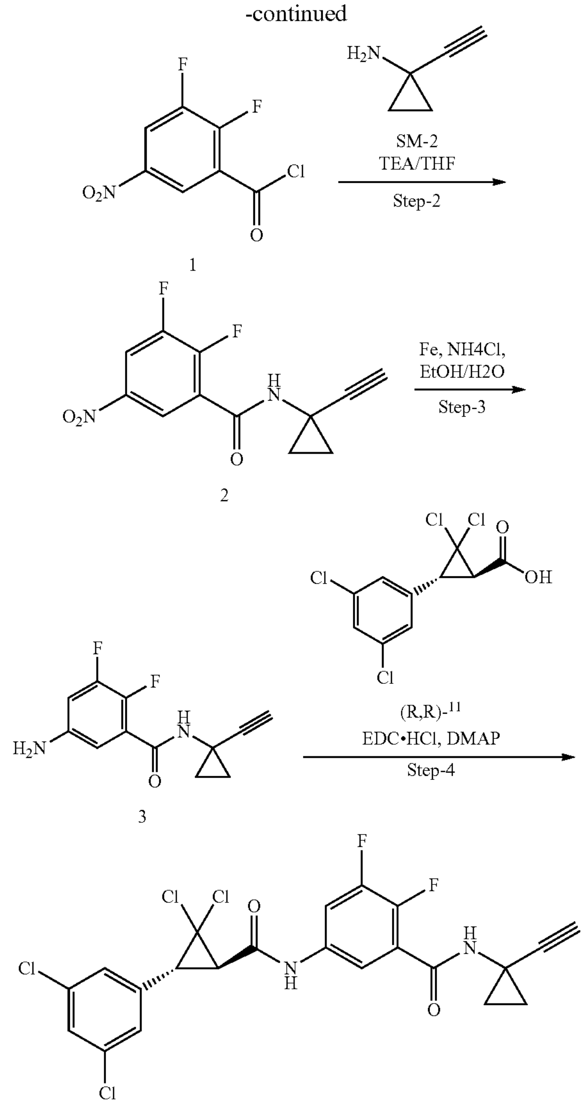

1

2

3

1617

Step-1

Synthesis of 2,3-difluoro-5-nitrobenzoyl chloride (1)

1

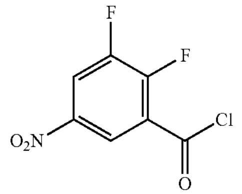

To a stirred solution of 2,3-difluoro-5-nitrobenzoic acid (SM-1) (5 g, 24.63 mmol) in DCM (50 mL) was added oxalyl chloride (2.67 ml, 29.55 mmol) at 0° C. and stirred for 5 min. To this, a catalytic amount of DMF (0.1 mL) was added and the reaction mixture was stirred at RT for 2 h. The progress of the reaction was monitored by TLC (30% Ethyl acetate in petrolether). After completion of reaction the volatiles were completely distilled off under vacuum to afford 2,3-difluoro-5-nitrobenzoyl chloride (1) (5.2 g, Crude) as light brown semi solid.

Step-2

Synthesis of N-(1-ethynylcyclopropyl)-2,3-difluoro-5-nitrobenzamide (2)

2

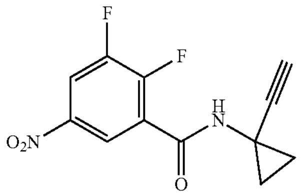

Experimental Procedure

A stirred solution of 1-ethynylcyclopropan-1-amine SM-2 (1.32 g, 11.28 mmol) in DCM (25 mL) was cooled to 0° C. Triethylamine (TEA) (4.7 mL, 33.85 mmol) was added, and the mixture was stirred for additional 10 minutes. A solution of 2,3-difluoro-5-nitrobenzoyl chloride (1) (2.5 g, 11.28 mmol) in DCM (10 mL) was added and the mixture was stirred for another 6 h at room temperature (RT). The progress of the reaction was monitored by TLC (50% ethyl acetate in petrolether; Rf=0.7). After completion of reaction, $H_2O$ (20 mL) was added to the reaction and the mixture was extracted with DCM (2x30 mL). The organic phase was dried over $Na_2SO_4$ and concentrated under reduced pressure to afford N-(1-ethynylcyclopropyl)-2,3-difluoro-5-nitrobenzamide (2) (2.87 g, crude) as a brown solid. ESIMS m/z 267.2 ([M+H]+).

Step-3

Synthesis of 5-amino-N-(1-ethynylcyclopropyl)-2,3-difluorobenzamide (3)

3

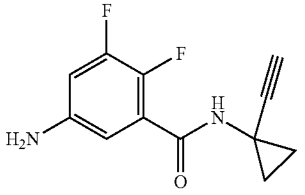

Experimental Procedure

A stirred solution of N-(1-ethynylcyclopropyl)-2,3-difluoro-5-nitrobenzamide (2) (2.87 g, 10.78 mmol) in EtOH/$H_2O$ (57 mL, 4:1 ratio) was brought to reaction with Fe (3.01 g, 53.94 mmol) and $NH_4Cl$ (2.88 g, 53.94 mmol) at 80° C. for 3 hours. The progress of the reaction was monitored by TLC (50% ethyl acetate in petrolether; Rf=0.2). After completion of the reaction, the mixture was filtered through a bed of celite, and washed with 10% MeOH/DCM (50 mL). The organic phase was diluted with $H_2O$ (40 mL), extracted with 10% MeOH/DCM (3x80 mL) and dried over $Na_2SO_4$. The crude compound was purified by column chromatography (silica gel 100-200; eluent gradient 18% ethyl acetate in petrolether) to afford 5-amino-N-(1-ethynylcyclopropyl)-2,3-difluorobenzamide (3) (1.7 g, 67%) as an off white solid. ESIMS m/z 237.2 ([M+H]+).

Step-4

Synthesis of 5-((1R,3R)-2,2-dichloro-3-(3,5-dichlorophenyl)cyclopropane-1-carboxamido)-N-(1-ethynylcyclopropyl)-2,3-difluorobenzamide (1617)

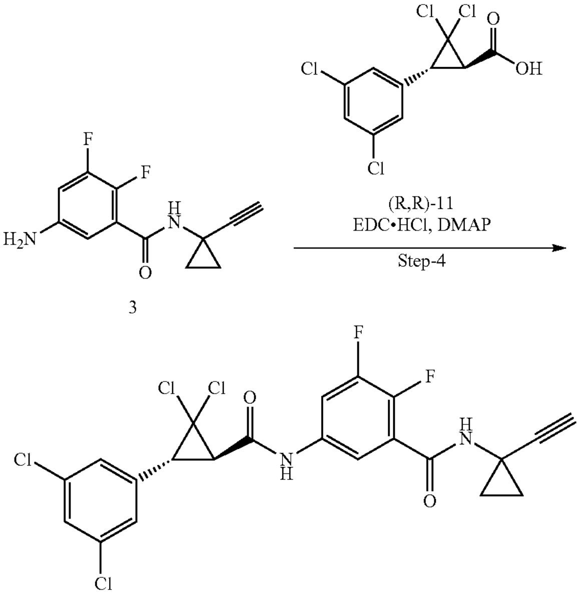

3

1617

Experimental Procedure

A stirred solution of (R,R)-11 (0.350 g, 1.16 mmol) in DCM (20 mL) was cooled to 0° C. EDC·HCl (0.33 g, 1.74 mmol) and DMAP (0.21 g, 1.74 mmol) were added and stirred for 10 min. To this mixture 5-amino-N-(1-ethynylcyclopropyl)-2,3-difluorobenzamide (3) (0.27 g, 1.16 mmol) was added and stirred at RT for 16 h. The progress of the reaction was monitored by TLC (30% ethyl acetate in petrolether; Rf=0.5). After completion, the reaction was diluted with $H_2O$ (40 mL). The organic phase was extracted with DCM (2x50 mL) and dried over $Na_2SO_4$. The crude compound was purified through column chromatography (silica gel 100-200; eluent gradient 15% ethyl acetate in petrolether) to afford 5-((1R,3R)-2,2-dichloro-3-(3,5-dichlorophenyl)cyclopropane-1-carboxamido)-N-(1-ethynylcyclopropyl)-2,3-difluorobenzamide (18D) (0.24 g, 40%) as an off white solid. 1H NMR (400 MHz, DMSO-d6) δ ppm 1.08 (br s, 2H), 1.18 (br s, 2H), 3.04 (s, 1H), 3.50 (d, J=8.4, 1H), 3.63 (d, J=8.4 Hz, 1H), 7.62-755 (m, 4H), 7.89-7.85 (m, 1H), 9.13 (s, 1H), 10.95 (s, 1H): ESIMS m/z 517.12 ([M+H]$^+$).

Chromatographic System:

Column: Xbridge BEH C18 Waters, 2.1×50 mm, 2.5μ

Oven: 40° C.

Eluents: Solvent A: water/$HCO_2H$ (0.05%); Solvent B: acetonitrile/$HCO_2H$ (0.05%)

Flow: 0.8 ml/min

Gradient:

| Time [min] | Solvent A [%] | Solvent B [%] |
|---|---|---|
| 0.0 | 98 | 2 |
| 1.2 | 0 | 100 |
| 1.7 | 0 | 100 |
| 2.2 | 98 | 2 |

Run time: 2.2 min+0.5 min equilibration time

| HPLC Rt | mass signal | MW | # |
|---|---|---|---|
| 1.219 | 561.8 | 562.1 | 1585 |
| 1.212 | 540.9 | 541.7 | 1601 |
| 1.228 | 535.8 | 535.6 | 1609 |

EXAMPLES

Example 1: Juvenile Sea Lice Contact Assay

Copepodids (juvenile sea lice stage of *Lepeophtheirus salmonis*) were exposed to seawater spiked with declining concentrations of a test compound (dissolved in a DMSO sea-water mixture). Sea lice inhibition (% of dead+damaged copepodids) was assessed after approximately 24 hours of continuous exposure. The vitality of used parasites was confirmed in a negative (solvent) control group.

Results: The following compounds showed ≥80% inhibition at a test concentration of 100 nM:

(* denotes 100% inhibition)

1514*, 1532*, 1544*, 1545*, 1546*, 1547*, 1549*, 1585*, 1587*, 1591*, 1606*, 1611*, 1616*, 1617*, 1625*, 1627, 1629*, 1631*.

The following compounds showed ≥80% inhibition at a test concentration of 10 nM:

(* denotes 100% inhibition)

1500, 1501, 1502*, 1508*, 1509*, 1510*, 1513*, 1515*, 1526*, 1531*, 1537*, 1539*, 1541*, 1552, 1553*, 1554, 1557*, 1561*, 1566*, 1570, 1573*, 1602*, 1603, 1604*, 1609*, 1612*, 1613*, 1615*, 1618*, 1619*, 1620*, 1621*, 1622, 1626, 1628*, 1630*.

The following compounds showed 80% inhibition at a test concentration of 1 nM:

(* denotes 100% inhibition)

1523, 1567*, 1574, 1589, 1590, 1601*, 1614, 1633.

The following compounds showed 80% inhibition at a test concentration of 0.1 nM:

(* denotes 100% inhibition)

1584*, 1592, 1594, 1623*, 1624*.

The following compounds showed 80% inhibition at a test concentration of 0.01 nM:

(* denotes 100% inhibition)

1536*, 1538*, 1551*, 1558*, 1559*, 1563*, 1565*, 1593*, 1605*, 1608*, 1632.

Example 2: Adult Sea Lice Contact Assay

Mobile stages of sea lice (i.e., pre-adults, adults of *Lepeophtheirus salmonis*) were exposed to seawater spiked with declining concentrations of a test compound (dissolved in a PEG sea-water mixture). Sea lice inhibition (% of dead+damaged sea lice) was assessed after approximately 1 and 24 hours of continuous exposure in comparison to a negative (solvent) control group.

Results: The following compounds had an $EC_{50}$≤25 nM and >10 nM:

1514, 1532, 1545, 1546, 1548, 1602, 1603, 1604, 1606, 1612.

The following compound had an $EC_{50}$≤10 nM and >1 nM:

1508, 1541, 1547, 1585, 1601, 1609, 1615, 1623, 1624, 1626, 1628.

The following compounds had an $EC_{50}$≤1 nM:

1584, 1587, 1589, 1590, 1592, 1593, 1594, 1605, 1608, 1613, 1614, 1617, 1618, 1619, 1620, 1621, 1622, 1625, 1630, 1632, 1633.

Example 3: Sea Lice Resistance Assay

A sea lice resistance assay was carried out using mobile sea lice stages (i.e., pre-adults, adults) of several *Lepeophtheirus salmonis*-isolates with known resistance profiles (i.e., fully susceptible or multiresistant (resistant to azametiphos (OP), emamectin benzoate (ML), deltamethrin (SP)). Sea lice were exposed to seawater spiked with declining concentrations of a test compound (dissolved in a PEG300/sea-water mixture). Sea lice inhibition (% of dead+damaged sea lice) was assessed after approximately 24 and 48 hours of continuous exposure in comparison to a negative (solvent) control group.

Results: Compound 1590 was equally effective against the sensitive isolate ($EC_{50}$ 4.12 ppb after 24 hours and 0.40 ppb after 48 hours) and the multi-resistant isolate ($EC_{50}$ 3.75 ppb after 24 hours and 0.58 ppb after 48 hours).

Salmon—In Vivo Efficacy Against Sea Lice

Example 4: Efficacy Trials Using Gavage Administration

Salmon (*Salmo salar*) were treated once orally by gavage at a dose of 5 mg/kg bodyweight per fish (Day 0). As formulation DMSO 5%/fish oil 95% was used. Salmon of the negative control group received only the excipients of the formulation.

The fish were infested with *Lepeophtheirus salmonis* copepodids twice before treatment (i.e., around day −28 and day −3) and once after treatment (i.e., day 17).

At day 7, fish were examined under sedation and (pre-) adult sea lice on each fish were counted and removed (assessment of therapeutic efficacy against (pre-)adult sea lice from day −28 infestation).

Around day 28 (end of animal phase), fish were euthanized, and lice on each fish were classified ((pre-)adult or juvenile stage) and counted. The number of (pre-) adult and juvenile parasite stages corresponding to the respective infestation time point were used for efficacy calculation, i.e., assessment of therapeutic efficacy against juvenile sea lice from day −3 infestation and assessment of prophylactic efficacy from day 17 re-infestation. Efficacy is expressed as a % reduction of sea lice in treated groups versus a control group, using the Abbott's formula.

Results: The following compounds had a therapeutic efficacy of 80% against (pre-)adult sea lice:

(* denotes 100% efficacy)

1541, 1584*, 1585*, 1587, 1590*, 1592*, 1593*, 1594*, 1601*, 1605*, 1606*, 1608*, 1609*, 1617*, 1618*,

1619*, 1620*, 1621*, 1622*, 1623*, 1624*, 1625*, 1626*, 1628*, 1630*, 1632*, 1633*.

The following compounds had a therapeutic efficacy of 80% against juvenile sea lice:

(* denotes 100% efficacy)

1541*, 1585*, 1590, 1592*, 1593, 1594*, 1601*, 1605*, 1606*, 1608*, 1609*, 1617*, 1618*, 1619, 1620, 1621, 1623, 1624, 1625*, 1626, 1628*, 1630*, 1632, 1633*.

The following compounds had a prophylactic efficacy of 80% at re-infestation on Day 17

(* denotes 100% efficacy):

1541*, 1590, 1594*, 1609*, 1617*, 1618*, 1624, 1625*, 1628*, 1630*, 1633.

Example 5: Efficacy Trials Using In-Feed Administration

Four study groups of fish (one group for assessment of therapeutic efficacy, one for assessment of prophylactic efficacy and their respective controls) were used. Commercial fish feed pellets were coated with formulated test compound. As formulation DMSO 5%/fish oil 95% was used. Salmon (*Salmo salar*) were treated orally with 1 mg/kg fish biomass via coated feed for 7 consecutive days. Salmon of the negative control groups received only feed coated with the excipients of the formulation.

Fish of the therapeutic groups were infested with *Lepeophtheirus salmonis* copepodids twice before treatment (around day −28 and day −3).

Around day 8, fish were examined under sedation and (pre) adult sea lice on each fish were counted and removed (assessment of therapeutic efficacy against (pre-)adult sea lice from around day −28 infestation).

Around day 25, fish were euthanized and (pre-) adult sea lice on each fish were counted (assessment of therapeutic efficacy against juvenile sea lice from around day −3 infestation.

Fish of the prophylactic groups were infested at several time points after treatment in 2-week intervals. The fish were assessed for (pre-)adult sea lice approximately 3 weeks after each re-infestation. At each assessment, all (pre-)adult sea lice were removed from the fish. The number of sea lice on fish corresponding to the respective re-infestation time point were used for prophylactic efficacy calculation. Efficacy is expressed as a % reduction of sea lice in treated groups versus a control group using the Abbott's formula.

Results: For compounds 1541, 1590, and 1594 100% therapeutic efficacy against (pre-)adult and juvenile sea lice was achieved.

Against re-infestation after treatment, prophylactic efficacies were 100% (D14) and 100% (D28) for compounds 1541 and 1594.

Against re-infestation after treatment, prophylactic efficacies were 100% (D14) and 79.2% (D28) for compound 1590.

The invention claimed is:

1. A method to control parasite infestations in fish comprising administering to a fish a compound of the following formula Formula (I)

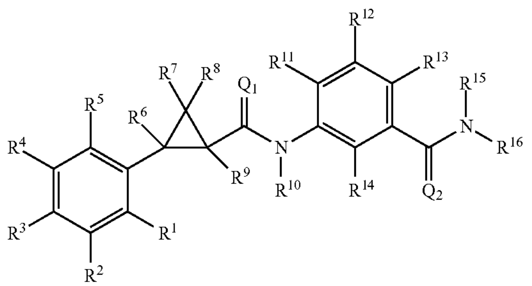

and N-oxides, veterinary acceptable acid addition salts, solvates, isotopes, stereoisomers, and tautomers, wherein $R^1$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, and $(C_1-C_6)$haloalkyl-$S(O)_2NH_2$;

$R^2$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^3$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^4$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$haloalkyl, $S(O)(C_1-C_6)$haloalkyl, $S(O)_2(C_1-C_6)$haloalkyl, $(C_1-C_6)$alkyl-$S(O)_2NH_2$, $(C_1-C_6)$haloalkyl-$S(O)_2NH_2$, and S-$(Halo)_5$;

$R^5$ is selected from the group consisting of H, F, Cl, Br, I, CN, $NH_2$, $NO_2$, $(C_1-C_6)$alkyl, $(C_3-C_6)$cycloalkyl, $(C_2-C_6)$alkenyl, $(C_3-C_6)$cycloalkenyl, $(C_2-C_6)$alkynyl, $(C_1-C_6)$alkoxy, $(C_1-C_6)$haloalkyl, $(C_3-C_6)$halocycloalkyl, $(C_2-C_6)$haloalkenyl, $(C_3-C_6)$halocycloalkenyl, $(C_1-C_6)$haloalkoxy, $S(C_1-C_6)$alkyl, $S(O)(C_1-C_6)$alkyl, $S(O)_2(C_1-C_6)$alkyl, $S(C_1-C_6)$ haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^6$ is selected from the group consisting of H and $(C_1\text{-}C_6)$alkyl;

$R^7$ is selected from the group consisting of H, F, Cl, Br, and I;

$R^8$ is selected from the group consisting of F, Cl, Br, and I;

$R^9$ is selected from the group consisting of H and $(C_1\text{-}C_6)$alkyl;

$R^{10}$ is selected from the group consisting of H, $(C_1\text{-}C_6)$alkyl, $(C_2\text{-}C_6)$alkenyl, $(C_1\text{-}C_6)$haloalkyl, $(C_1\text{-}C_6)$alkyl$(C_1\text{-}C_6)$alkoxy, $C(=O)(C_1\text{-}C_6)$alkyl, and $(C_1\text{-}C_6)$alkoxy$C(=O)(C_1\text{-}C_6)$alkyl;

$R^{11}$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^{12}$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^{13}$ is selected from the group consisting of H, F, Cl, Br, I, CN, $NH_2$, $NO_2$, CHO, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, $(C_1\text{-}C_6)$haloalkyl-$S(O)_2NH_2$, and triazolyl;

$R^{14}$ is selected from the group consisting of H, F, Cl, Br, I, CN, $NH_2$, $NO_2$, $(C_1\text{-}C_6)$alkyl, $(C_3\text{-}C_6)$cycloalkyl, $(C_2\text{-}C_6)$alkenyl, $(C_3\text{-}C_6)$cycloalkenyl, $(C_2\text{-}C_6)$alkynyl, $(C_1\text{-}C_6)$alkoxy, $(C_1\text{-}C_6)$haloalkyl, $(C_3\text{-}C_6)$halocycloalkyl, $(C_2\text{-}C_6)$haloalkenyl, $(C_3\text{-}C_6)$halocycloalkenyl, $(C_1\text{-}C_6)$haloalkoxy, $S(C_1\text{-}C_6)$alkyl, $S(O)(C_1\text{-}C_6)$alkyl, $S(O)_2(C_1\text{-}C_6)$alkyl, $S(C_1\text{-}C_6)$haloalkyl, $S(O)(C_1\text{-}C_6)$haloalkyl, $S(O)_2(C_1\text{-}C_6)$haloalkyl, $(C_1\text{-}C_6)$alkyl-$S(O)_2NH_2$, and $(C_1\text{-}C_6)$haloalkyl-$S(O)_2NH_2$;

$R^{15}$ is selected from the group consisting of H, $(C_1\text{-}C_6)$alkyl, $(C_2\text{-}C_6)$alkenyl, $(C_2\text{-}C_6)$alkynyl, $(C_1\text{-}C_6)$haloalkyl, $(C_1\text{-}C_6)$alkyl$(C_1\text{-}C_6)$alkoxy, $C(=O)(C_1\text{-}C_6)$alkyl, and $(C_1\text{-}C_6)$alkoxy$C(=O)(C\text{-}C_6)$alkyl;

$R^{16}$ is selected from the group consisting of $(C_1\text{-}C_8)$alkyl, $(C_3\text{-}C_8)$cycloalkyl, $(C_1\text{-}C_8)$alkyl-O—$(C_1\text{-}C_8)$alkyl, $(C_1\text{-}C_8)$alkyl$(C_3\text{-}C_8)$cycloalkyl, $(C_1\text{-}C_8)$alkylphenyl, $(C_2\text{-}C_8)$alkenyl, $(C_2\text{-}C_8)$alkynyl, $(C_1\text{-}C_8)$haloalkyl, $(C_1\text{-}C_8)$alkyl-S—$(C_1\text{-}C_8)$alkyl, $(C_1\text{-}C_8)$alkyl-S(O)—$(C_1\text{-}C_8)$alkyl, $(C_1\text{-}C_8)$alkyl-$S(O)_2$—$(C_1\text{-}C_8)$alkyl, O-phenyl, O—$(C_2\text{-}C_8)$alkenyl, O—$(C_1\text{-}C_8)$alkyl$(C_3\text{-}C_8)$cycloalkyl, O—$(C_1\text{-}C_8)$alkylphenyl, $(C_1\text{-}C_8)$alkyl-O—$(C_1\text{-}C_8)$alkyl$(C_3\text{-}C_8)$cycloalkyl, $(C_1\text{-}C_8)$alkyl-O—$(C_1\text{-}C_8)$haloalkyl, $(C_1\text{-}C_8)$alkyl-C(=O)NH—$(C_1\text{-}C_8)$haloalkyl, $(C_1\text{-}C_8)$alkyl-NHC(O)—$(C_1\text{-}C_8)$alkyl, $(C_1\text{-}C_8)$alkyl-S—$(C_1\text{-}C_8)$haloalkyl, $(C_1\text{-}C_8)$alkyl-S(O)—$(C_1\text{-}C_8)$haloalkyl, $(C_1\text{-}C_8)$alkyl-$S(O)_2$—$(C_1\text{-}C_8)$haloalkyl, $(C_1\text{-}C_8)$alkyl-$S(O)_2$—$NH_2$, and a heterocycle, wherein each alkyl, alkenyl, alkynyl, alkyl-cycloalkyl, haloalkyl, and phenyl, may be optionally substituted with one or more substituents selected from the group consisting of F, Cl, Br, I, CN, OH, $NH_2$, $NO_2$, $(C_1\text{-}C_8)$alkyl, $(C_2\text{-}C_8)$alkenyl, $(C_2\text{-}C_8)$alkynyl, $(C_1\text{-}C_8)$alkoxy, $(C_1\text{-}C_8)$haloalkyl, $N((C_1\text{-}C_8)alkyl)_2$, $C(O)O(C_1\text{-}C_8)$alkyl, benzothioenyl, oxoimidazolidinyl, furanyl, pyrazolyl, pyridinyl, thiazolyl, and triazolyl, and wherein the heterocycle is selected from the group consisting of, azetidinyl, 2,5-dioxoimidazolidinyl, 2,4-dioxo-1,3-diazaspiro[4.4]nonanylisoxazolidinonyl, imidazolidinonyl, isoxazolidinonyl, morpholinyl, oxazolidinonyl, oxetanyl, piperazinyl, piperidinyl, pyranyl, pyrrolidinyl, pyrrolidinonyl, tetrahydrofuranyl, tetrahydropyranyl, tetrahydrothiophenyl, tetrahydrothiophenyl-oxide, tetrahydrothiophenyl-dioxide, thietanyl, thietanyl-oxide, thietanyl-dioxide, and thioxothiazolidinonyl, and wherein each $(C_3\text{-}C_8)$cycloalkyl and heterocycle may be optionally substituted with one or more substituents selected from the group consisting of H, F, Cl, Br, I, CN, $NH_2$, $NO_2$, oxo, $(C_1\text{-}C_4)$alkyl, $(C_2\text{-}C_8)$alkenyl, $(C_2\text{-}C_8)$alkynyl, $(C_1\text{-}C_4)$haloalkyl, $C(=O)O(C_1\text{-}C_4)$alkyl, $(C=O)NH(C_1\text{-}C_4)$alkyl, $(C=O)NH(C_1\text{-}C_4)$haloalkyl, $C(=O)(C_3\text{-}C_6)$cyclopropyl, $C(=O)(C_1\text{-}C_4)$haloalkyl, $C(=O)(C_1\text{-}C_4)$alkyl$(C_1\text{-}C_4)$alkoxy, and $(C_1\text{-}C_4)$alkyl-morpholinyl$R^{15}$ and $R^{16}$ together can optionally form a 2- to 5-membered saturated or unsaturated, hydrocarbyl link, which may contain one or more heteroatoms selected from the group consisting of nitrogen, sulfur, and oxygen, wherein said hydrocarbyl link may be optionally substituted with one or more substituents selected from the group consisting of F, Cl, Br, I, CN, $NH_2$, and $NO_2$;

$Q^1$ and $Q^2$ are each independently selected from the group consisting of O and S.

2. A method to control parasite infestations in fish according to claim 1, wherein $R^{16}$ is selected from the group consisting of $(C_1\text{-}C_8)$alkyl, $(C_3\text{-}C_8)$cycloalkyl, $(C_1\text{-}C_8)$alkyl-O—$(C_1\text{-}C_8)$alkyl, $(C_1\text{-}C_8)$alkyl$(C_3\text{-}C_8)$cycloalkyl, $(C_2\text{-}C_8)$alkenyl, $(C_2\text{-}C_8)$alkynyl, $(C_1\text{-}C_8)$haloalkyl, $(C_1\text{-}C_8)$alkyl-S—$(C_1\text{-}C_8)$alkyl, $(C_1\text{-}C_8)$alkyl-S(O)—$(C_1\text{-}C_8)$alkyl, $(C_1\text{-}C_8)$alkyl-$S(O)_2$-$(C_1\text{-}C_8)$alkyl, $(C_1\text{-}C_8)$alkyl-O—$(C_1\text{-}C_8)$haloalkyl, $(C_1\text{-}C_8)$alkyl-S—$(C_1\text{-}C_8)$haloalkyl, $(C_1\text{-}C_8)$alkyl-S(O)—$(C_1\text{-}C_8)$haloalkyl, $(C_1\text{-}C_8)$alkyl-$S(O)_2$—$(C_1\text{-}C_8)$haloalkyl, $(C_1\text{-}C_8)$alkyl-$S(O)_2$—$NH_2$, and heterocycle, wherein each alkyl, alkenyl, alkynyl, alkyl-cycloalkyl, and haloalkyl in $R^{16}$, may be optionally substituted with one or more substituents selected from the group consisting of F, Cl, Br, I, CN, OH, $NH_2$, $NO_2$, $(C_1\text{-}C_8)$alkyl, $(C_2\text{-}C_8)$alkenyl, $(C_2\text{-}C_8)$alkynyl, $(C_1\text{-}C_8)$alkoxy, $(C_1\text{-}C_8)$haloalkyl, $C(O)O(C_1\text{-}C_8)$alkyl, oxoimidazolidinyl, furanyl, and pyrazolyl, wherein each $(C_3\text{-}C_8)$cycloalkyl, may be optionally substituted with one or more substituents selected from the group consisting of H, F, Cl, Br, I, CN, $NH_2$, $NO_2$, oxo, $(C_1\text{-}C_4)$alkyl, $(C_2\text{-}C_8)$alkenyl, $(C_2\text{-}C_8)$alkynyl, $(C_1\text{-}C_4)$haloalkyl, $C(=O)O(C_1\text{-}C_4)$alkyl, $(C=O)NH(C_1\text{-}C_4)$ alkyl, (C-O)NH$(C_1$-$C_4)$haloalkyl, C(═O)$(C_3$-$C_6)$cyclopropyl, C(═O)$(C_1$-$C_4)$haloalkyl, C(═O)$(C_1$-$C_4)$alkyl$(C_1$-$C_4)$alkoxy, and $(C_1$-$C_4)$alkyl-morpholinyl, wherein the heterocylce is selected from the group consisting of azetidinyl, imidazolidinonyl, isoxazolidinonyl, oxetanyl, pyrrolidinyl, pyrrolidinonyl, tetrahydrofuranyl, tetrahydrothiophenyl, and tetrahydrothiophenyl-oxide, wherein, each heterocycle in $R^{16}$ may be optionally substituted with one or more substituents selected from the group consisting of H, F, Cl, Br, I, CN, oxo, $(C_1$-$C_4)$alkyl, $(C_2$-$C_8)$alkenyl, $(C_2$-$C_8)$alkynyl, $(C_1$-$C_4)$haloalkyl, (C═O)NH$(C_1$-$C_4)$alkyl, (C═O)NH$(C_1$-$C_4)$haloalkyl, and C(═O)$(C_1$-$C_4)$alkyl$(C_1$-$C_4)$alkoxy.

3. A method to control parasite infestations in fish claim 1, wherein $R^{16}$ is selected from the group consisting of $(C_1$-$C_8)$alkyl, $(C_3$-$C_8)$cycloalkyl, $(C_1$-$C_8)$alkyl$(C_3$-$C_8)$cycloalkyl, $(C_2$-$C_8)$alkenyl, $(C_2$-$C_8)$alkynyl, $(C_1$-$C_5)$haloalkyl, $(C_1$-$C_8)$alkyl-S—$(C_1$-$C_8)$alkyl, $(C_1$-$C_8)$alkyl-S(O)—$(C_1$-$C_5)$alkyl, $(C_1$-$C_5)$alkyl-$S(O)_2$—$(C_1$-$C_8)$alkyl, and (C-$C_8)$alkyl-O—$(C_1$-$C_8)$haloalkyl, wherein each alkyl, cycloalkyl, alkenyl, alkynyl, and haloalkyl, may be optionally substituted with one or more substituents selected from the group consisting of F, Cl, Br, $(C_1$-$C_8)$alkyl, $(C_2$-$C_8)$alkenyl, $(C_2$-$C_8)$alkynyl, $(C_1$-$C_8)$alkoxy, C(O)O$(C_1$-$C_8)$alkyl, and oxoimidazolidinyl, wherein in the $(C_3$-$C_8)$cycloalkyl, may be optionally substituted with one or more substituents selected from the group consisting of H, F, Cl, Br, I, CN, $NH_2$, $NO_2$, oxo, $(C_1$-$C_4)$alkyl, $(C_2$-$C_8)$alkenyl, $(C_2$-$C_5)$alkynyl, $(C_1$-$C_4)$haloalkyl, (C-O)NH$(C_1$-$C_4)$alkyl, and (C═O)NH$(C_1$-$C_4)$haloalkyl.

4. A method to control parasite infestations in fish according to claim 1, wherein $Q^1$ and $Q^2$ are O.

5. A method to control parasite infestations in fish according to claim 1, wherein:

$R^5$ is H;

$R^6$ is H;

$R^7$ is selected from the group consisting of $C_1$ and Br;

$R^8$ is selected from the group consisting of $C_1$ and Br;

$R^9$, $R^{10}$, and $R^{11}$ is H.

6. A method to control parasite infestations in fish according to claim 1, wherein $R^{13}$ is selected from the group consisting of H, F, Cl, $CH_3$ and $CF_3$.

7. A method to control parasite infestations in fish according to claim 1, wherein $R^{12}$ is selected from the group consisting H, F, Cl, Br, $CH_3$.

8. A method to control parasite infestations in fish according to claim 1, wherein $R^{14}$ is H or F.

9. A method to control parasite infestations in fish according to claim 1, wherein $R^{15}$ is selected from the group consisting of H and $CH_3$.

10. A method to control parasite infestations in fish according to claim 1, wherein the parasite infestation is a sea lice infestation.

11. A method to control parasite infestations in fish according to claim 1, wherein the parasite is at least one of *Lepeophtheirus salmonis, Caligus celmensi, Caligus curtus, Caligus dussumieri, Caligus elongates, Caligus longicaudatus, Caligus rogercresseyi* or *Caligus stromii.*

12. A method to control parasite infestations in fish according to claim 1, wherein the parasite infestation is with copepodites, pre-adult, or adult sea lice or a mixed infestation with various stages.

13. A method to control parasite infestations in fish according to claim 1, wherein the rate of infestation of the fish is between 0.5 and 3 parasites on average per fish in a fish facility.

14. A method to control parasite infestations in fish according to claim 1, wherein the method comprises administering to fish the compound of Formula (I) as defined in claim 1 by oral administration, or by topical administration such as by bath treatment or by intraperitoneal or intramuscular injection.

15. A method to control parasite infestations in fish, wherein the method comprises administering to fish the compound of Formula (I) as defined in claim 1 by oral administration, wherein the oral administration comprises administering a medicated fish feed comprising a therapeutically effective amount the compound and fish feed.

16. A method to control parasite infestations in fish according to claims, wherein the method comprises administering the compound of Formula (I) as defined in claim 1, by bath treatment, wherein the bath treatment comprises immersion of fish in water with a therapeutically effective amount of a compound.

17. A method to control parasite infestations in fish according to claim 1, wherein the fish is a salmonide.

18. A method to control parasite infestations in fish according to claim 1, wherein the compound is a compound of the following formula Formula (II)

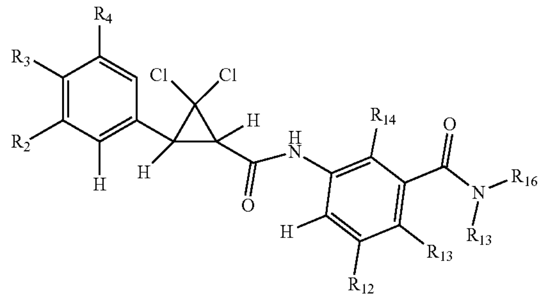

and N-oxides, veterinary acceptable acid addition salts, solvates, isotopes, stereoisomers, and tautomers, wherein the compound is selected from the group consisting of

| # | R2 | R3 | R4 | R12 | R13 | R14 | R15 | $R^{16}$ |
|---|---|---|---|---|---|---|---|---|
| 1541 | Cl | Cl | Cl | H | Cl | H | H | 1-cyanocyclopropyl |
| 1584 | F | F | H | H | Cl | H | H | 2,2,2-trifluoroethyl |
| 1585 | Cl | Br | H | H | Cl | H | H | 1-cyanocyclopropyl |
| 1587 | F | $CHF_2$ | H | H | Cl | H | H | 1-cyanocyclopropyl |
| 1590 | Cl | H | Cl | H | Cl | H | H | 1-cyanocyclopropyl |
| 1592 | Cl | H | Cl | H | Cl | H | H | 2,2,2-trifluoroethyl |
| 1593 | F | F | F | H | Cl | H | H | 2,2.2-trifluoroethyl |
| 1594 | Cl | H | Cl | F | F | H | H | 1-cyanocyclopropyl |
| 1601 | H | H | $CF_3$ | H | Cl | H | H | 3,3-difluorocyclobutyl |
| 1605 | Cl | H | Cl | H | F | H | H | 1-cyanocyclopropyl |
| 1606 | H | Cl | F | H | Cl | H | H | 1-cyanocyclopropyl |
| 1608 | H | F | Cl | H | Cl | H | H | 1-cyanocyclopropyl |
| 1609 | Cl | F | Cl | H | Cl | H | H | 1-cyanocyclopropyl |
| 1617 | Cl | H | Cl | F | F | H | H | 1-ethynylcyclopropyl |
| 1618 | Cl | H | Cl | F | F | H | H | cyclopropyl |
| 1619 | Cl | H | Cl | H | Cl | H | H | 1-methylcyclopropyl |

-continued

| # | R2 | R3 | R4 | R12 | R13 | R14 | R15 | $R^{16}$ |
|---|---|---|---|---|---|---|---|---|
| 1620 | Cl | H | Cl | H | Cl | H | H | 1-ethynylcyclopropyl |
| 1621 | Cl | H | Cl | H | Cl | H | H | cyclopropyl |
| 1622 | Cl | H | Cl | H | Cl | H | H | prop-2-ynyl |
| 1623 | F | F | F | H | F | H | H | 1-cyanocyclopropyl |
| 1624 | F | F | F | H | Cl | H | H | 1-cyanocyclopropyl |
| 1625 | Cl | H | Cl | H | Cl | H | H | 3,3-difluorocyclobutyl |
| 1626 | Cl | H | Cl | H | F | H | H | 1-methylcyclopropyl |
| 1628 | Cl | H | Cl | F | F | H | H | 3,3-difluorocyclobutyl |
| 1630 | Cl | H | Cl | H | F | H | H | 3,3-difluorocyclobutyl |
| 1632 | Cl | H | Cl | H | F | H | H | cyclopropyl |
| 1633 | Cl | H | Cl | H | F | H | H | 1-ethynylcyclo-propyl. |

19. A premix comprising a compound of Formula (I) as defined in claim 1, wherein the premix further comprises nutrients.

20. The premix according to claim 19, wherein the premix comprises nutrients in the form of pellets wherein the pellets are coated with a composition comprising a compound of Formula (I).

21. A medicated fish feed comprising the premix as defined in claim 19 and fish feed.

* * * * *